(12) United States Patent
Tajima et al.

(10) Patent No.: US 8,168,142 B2
(45) Date of Patent: May 1, 2012

(54) CASSETTE FOR STACKING SPECIMEN, SPOTTING DEVICE, AND SPECIMEN STACKING DEVICE

(75) Inventors: Hideji Tajima, Chiba (JP); Tsutomu Asano, Chiba (JP); Junko Asahina, Chiba (JP); Mamiko Yoshida, Chiba (JP)

(73) Assignee: Universal Bio Research Co., Ltd., Chiba (JP)

( * ) Notice: Subject to any disclaimer, the term of this patent is extended or adjusted under 35 U.S.C. 154(b) by 637 days.

(21) Appl. No.: 11/568,112

(22) PCT Filed: Apr. 20, 2005

(86) PCT No.: PCT/JP2005/007508
§ 371 (c)(1),
(2), (4) Date: Jul. 2, 2009

(87) PCT Pub. No.: WO2005/103724
PCT Pub. Date: Mar. 11, 2005

(65) Prior Publication Data
US 2010/0018331 A1    Jan. 28, 2010

(30) Foreign Application Priority Data

Apr. 20, 2004 (JP) .................... 2004-124873

(51) Int. Cl.
*A61J 1/06*    (2006.01)
*G01N 37/00*    (2006.01)
(52) U.S. Cl. ................... 422/554; 73/864.91
(58) Field of Classification Search ............. 422/554; 73/864.91
See application file for complete search history.

(56) References Cited

U.S. PATENT DOCUMENTS

2001/0038808 A1* 11/2001 Tajima ................ 422/56
(Continued)

FOREIGN PATENT DOCUMENTS

JP    2001-136968    5/2001
(Continued)

OTHER PUBLICATIONS

International Preliminary Report on Patentability issued by The International Bureau of WIPO, mailed Oct. 25, 2006, in connection with PCT/JP2005/007508.
(Continued)

*Primary Examiner* — Lore Jarrett
(74) *Attorney, Agent, or Firm* — Haynes and Boone, LLP

(57) ABSTRACT

It is an object of this invention to provide a sample integration cassette, a spotting device and a sample integration device which enhance a sample integration density and reduce the size of a sample assembly and a probe. The sample integration cassette has the sample assembly and the sample support carrier so arranged therein that the sample support can be fed from the sample support carrier onto the sample assembly at a predetermined angle to the sample assembly at all times. The cassette is formed so as to be connectable with a drive unit that applies a drive force to the sample assembly and the sample support carrier interlockingly and synchronously. The spotting device has a delivery member mounting table which is vertically moved over the sample support carrier to apply samples to the sample support from the delivery member. The sample integration device rotatably supports the sample support carrier and includes a rotary drive unit for rotating the sample support carrier and the sample assembly and a biasing means connected to the rotary drive unit to pull the cassette in one direction. The sample assembly rotating device includes a rotating shaft to which the sample assembly is fitted at one end, a drive means to drive the rotating shaft, and a power supply for the drive means.

8 Claims, 44 Drawing Sheets

U.S. PATENT DOCUMENTS

2002/0188224 A1 * 12/2002 Roe et al. .................. 600/584

FOREIGN PATENT DOCUMENTS

| | | |
|---|---|---|
| JP | 2001-515735 | 9/2001 |
| JP | 2002-286727 | 10/2002 |
| JP | 2002-540380 | 11/2002 |
| JP | 2003-14746 | 1/2003 |
| JP | 2003-294743 | 10/2003 |
| WO | WO/99/03341 | 1/1999 |
| WO | WO 01/61361 A1 | 8/2001 |
| WO | WO 01/69249 A1 | 9/2001 |
| WO | WO/02/45842 A1 | 6/2002 |
| WO | WO 02/063300 A1 | 8/2002 |
| WO | WO 03/083111 A1 | 10/2003 |

OTHER PUBLICATIONS

Written Opinion issued by the ISA/JP, mailed Oct. 25, 2006, in connection with PCT/JP2005/007508.

International Search Report issued by the ISA/JP, mailed Aug. 30, 2005, in connection with PCT/JP2005/007508.

* cited by examiner

US 8,168,142 B2

CASSETTE FOR STACKING SPECIMEN, SPOTTING DEVICE, AND SPECIMEN STACKING DEVICE

CROSS REFERENCE

This application is a United States national phase application of co-pending international patent application number PCT/JP2005/007508, filed Apr. 20, 2005, which claims priority to Japanese patent application number 2004-124873, filed Apr. 20, 2004 which priority is claimed.

TECHNICAL FIELD

The present invention relates to a sample integration cassette, a spotting device and a sample integration device, all used to adjust a sample assembly comprising a spirally wound, threadlike sample support to which samples containing various kinds of biological substances are attached at equal intervals.

BACKGROUND ART

The inventors of this invention have previously conducted research into the method and device for determining biological substances, such as base sequences of genes, and developed various kinds of devices for an accommodation-reaction-measurement process. Because of its effectiveness in reducing the amount of use of samples containing detection biological substances and the amount of labeled object biological substances, an accommodation-reaction-measurement method using a probe comprising a combination of a pipettelike container and a sample assembly is finding a widening range of applications. The probe used in the accommodation-reaction-measurement method includes, for example, one that has accommodated in a light-transmitting narrow tube a rodlike base member, to the surface of which a large number of samples are attached at equal intervals in a longitudinal direction of the base member, or one that has a sample assembly accommodated in a pipettelike container, the sample assembly comprising a threadlike sample support, to the surface of which a large number of samples are attached at equal intervals in a longitudinal direction of the support, and a rodlike core around which the sample support is spirally wound. (Patent document 1, 2 and 3).

In the accommodation-reaction-measurement method using the probe, the lower end of the probe is inserted into a container accommodating liquids suspending a labeled biological substance to draw the liquid into the probe until the liquid soaks an entire sample support winding portion (or simply referred to as a core) of the sample assembly, thereby bonding the detection biological substance adhering to the sample support to a binding material in the labeled biological substance.

After this, the labeled biological substance suspending liquid drawn in from the lower end of the probe is discharged. Then a cleansing liquid is drawn into and discharged from the pipette to clean the interior of the pipette and wash out a residue of the labeled biological substance suspending liquid.

After cleaning, a measuring liquid is drawn into the pipette which is then set in an accommodation-reaction-measurement device. The pipette is radiated with an ultraviolet light from outside the probe to cause a fluorescent material to emit light at a position where the detection biological substance binds with the binding material in the labeled biological substance. The illuminating positions on the entire core are measured by a light receiving portion and, from each of the detected illuminating positions, the binding material in the labeled biological substance is determined. Based on a combination of all the detected binding materials, a target substance is determined.

For example, with a sample assembly 2 accommodated in the pipette 1 as shown in FIG. 45, a core 2a of the sample assembly 2 is situated at the lower end of a large-diameter portion of the pipette 1 so that it can easily contact the liquid drawn in from a small-diameter portion 1b. For this purpose, a cap 2b at the front end of the core 2a is formed to engage a throttled portion at a boundary between the large-diameter portion and the small-diameter portion 1b of the pipette 1. And a cylindrical handle 2c, over which a front end of a jig (not shown) is sleeved to push the sample assembly 2 down to the throttled portion, is formed smaller in diameter than the core 2a so that it protrudes coaxially from the base of the sample assembly 2.

Such a sample assembly 2 is made by using a spotting device 4 shown in FIG. 46, i.e., by attaching sample containing liquids to a large number of locations at one time on a threadlike sample support wound on a platelike sample support carrier 3 (sample support is not shown because it is too fine to recognize) and then by spirally winding the sample support attached with the samples around the core 2a.

The spotting device 4 used, as shown in FIG. 46, has an almost square delivery portion 5 assembled onto a movable portion 4c secured at the top of guide posts 4b, . . . , 4b by a plurality of springs 4a, . . . , 4a. Installed immediately below the delivery portion 5 are a cassette 6 comprising the sample assembly 2 and the platelike sample support carrier 3 wound with the sample support and a microplatelike vessel 7 mounted on the cassette 6 and having a large number of wells 7a, . . . , 7a.

In this spotting device 4, sample suspending liquids to be applied to the sample support are accommodated in the wells 7a, . . . , 7a of the vessel 7 in advance, which is placed on the cassette 6 located at a predetermined position. The movable portion 4c mounted with the delivery portion 5 is pushed down against the spring force to insert dip ends protruding from the underside of the delivery portion 5 (not shown, referred to as pins) into the wells 7a, . . . , 7a to bring them into contact with the liquids. After it is confirmed that each pin of the delivery portion 5 has been dipped in the associated liquid, the movable portion 4c is lifted by the spring force to the original position.

With the delivery portion 5 lifted, the vessel 7 is taken out from the top of the cassette 6 and then the movable portion 4c is pushed down again against the spring force to lower the pins protruding from the underside of the delivery portion 5 onto the sample support carrier 3 assembled on the cassette 6. These pins come into contact with the sample support wound around the sample support carrier 3, transferring the liquids adhering to the lower ends of the pins onto the sample support side.

Then, the movable portion 4c is lifted by the spring force to the initial position. Now, the sample support wound on one side of the sample support carrier 3 is attached with samples and can be taken out.

When samples are applied to the sample support situated on the opposite side of the sample support carrier 3, the process involves arranging the sample assembly 2 at the same position but with its front and back reversed and repeating the above procedure.

After the samples have been applied to and fixed in the sample support wound on the sample support carrier 3, the sample support is taken up from the sample support carrier 3 and wound around the core 2a to form the sample assembly 2. This state represents the sample assembly 2 before being put into the pipette 1.

This sample assembly 2 is taken out of the cassette 6 and put into the pipette 1 from its front end side, thus forming a probe used in an accommodation-reaction-measurement process to determine an object biological substance (patent document 4).

Patent document 1: WO02/045842 A1
Patent document 2: WO99/003341
Patent document 3: SO02/063300 A1
Patent document 4: Patent application No. 2003-177228

In the conventional devices, various sample suspending liquids for spotting are accommodated in microplates of global standard—a 48-hole microplate (6 rows×8 columns), a 96-hole microplate (8 rows×12 columns at 9-mm pitch), a 384-hole microplate (16 rows×24 columns at 4.5-mm pitch) and a 1536-hole microplate (32 rows×48 columns at 2.25-mm pitch).

Since the size of the vessel 7 is fixed, the interval at which the samples are arrayed on the sample support by inserting the pins into the wells 7a, . . . , 7a to dip them in the sample suspending liquids is determined by the number of pins. And the length of the sample support and the size of the sample assembly 2 also increase with these dimensions. Because the size of the sample assembly 2 and the size of the pipette 1 accommodating the sample assembly 2 are determined by the number of holes in the microplate, the probe cannot be reduced in size freely.

Further, since the size of the vessel 7 is fixed, the sample array positions cannot be increased nor is it possible to enhance the density of the sample arrangement.

Further, since the size of the sample assembly 2 and the pipette 1 cannot be changed, the amount of liquid to soak the core 2a of the sample assembly 2, for example, also increases and cannot be reduced. If the same concentrations are used, a greater amount of sample is required in each liquid.

Since the size of the measuring device also increases with the size of the sample assembly 2 and the pipette 1, the cost of measurement increases.

Further, when spirally winding the sample support around the core 2a of the sample assembly 2, it must be wound uniformly on the core 2a. It is however difficult to wind it as uniformly as desired because of slack and slipping of the sample support during winding.

Because of these, the accommodation-reaction-measurement method has a drawback of increased cost in terms of the manufacturing equipment, measuring device and other materials for the sample assembly 2.

DISCLOSURE OF THE INVENTION

Task to be Achieved by the Invention

The present invention has been accomplished with a view to overcoming the above problems experienced with the conventional technology. A concrete technical task set forth to solve the problems is to provide a sample integration cassette, a spotting device and a sample integration device which are capable of uniformly winding a sample support around the core, increasing a sample integration density and reducing the size of the sample assembly and the probe, which in turn results in a reduced size of the measuring device and cost associated with the accommodation-reaction-measuring process.

Means to Achieve the Task

The following describes means for effectively achieving the above tasks which cover all necessary items to determine the sample integration cassette, the spotting device and the sample integration device.

According to a first task achieving means, the present invention provides a sample integration cassette including: a sample support carrier having a sample support wound thereon; a sample assembly to which the sample support is fed from the sample support carrier and wound around the sample assembly, wherein the sample assembly and the sample support carrier are arranged so that the sample support can be fed from the sample support carrier to the sample assembly at a constant angle at all times; and a drive unit connectable to the sample assembly and the sample support carrier to give a drive force interlockingly and synchronously to the sample assembly and the sample support carrier.

According to a second task achieving means, this invention provides a sample integration cassette according to the above means, wherein the sample assembly integrally has a core and a head; wherein the core is formed with a spiral groove at a predetermined pitch and has the sample support wound in the spiral groove; wherein the head is connected to a front end of the core such that it is movable toward and away from the front end of the core to hold a front end portion of the sample support.

According to a third task achieving means, this invention provides a sample integration cassette according to the above means, wherein the sample assembly is formed with an O-ring groove at a rear end of the core so that a rear end portion of the sample support can be held by an O-ring fitted in the O-ring groove.

According to a fourth task achieving means, this invention provides a sample integration cassette according to the above means, comprising: a central body portion to axially accommodate the sample assembly such that it is rotatable about its axis; and a pair of side support portions to rotatably support the sample support carrier such that the spiral groove formed in the sample assembly for winding the sample support is almost parallel to the sample support wound on the sample support carrier; wherein the pair of side support portions and the central body portion having the side support portions at both ends thereof combine to form a gatelike structure to wind the sample support onto the sample assembly from the sample support carrier.

According to a fifth task achieving means, this invention provides a sample integration cassette according to the above means, wherein the central body portion has formed in a side surface of a sample assembly accommodation portion thereof an opening that allows the sample assembly to be connected with a drive shaft; wherein the side support portion has formed in a side surface of a carrier shaft support portion thereof an opening that allows the sample support carrier to be connected with a drive shaft that rotates in synchronism with the rotation of the sample assembly, so that the sample assembly and the sample support carrier can be interlocked with each other.

According to a sixth task achieving means, this invention provides a spotting device comprising: a base on which to mount a sample support carrier; a stand erected on the base; a guide rail integrally provided on the stand; a movable table vertically movable along the guide rail; and a delivery member mounting table provided to the movable table and having a mounting portion in which the delivery member is removably mounted; wherein the delivery member mounted in the mounting portion is lowered onto the sample support carrier to apply samples to a sample support wound on the sample support carrier in a predetermined row and column matrix at one time.

According to a seventh task achieving means, this invention provides a spotting device according to the above means, wherein a coil spring type biasing means is installed between the stand and the movable table to apply an upwardly pushing force to the movable table at all times, so that when the delivery member is not lowered, the movable table is kept at an upper end of the stand by the spring biasing force.

According to an eighth task achieving means, this invention provides a sample integration device comprising: a cassette mount on which to mount a sample integration cassette incorporating a sample assembly and a sample support carrier in a predetermined direction, the cassette mount being adapted to support the sample support carrier rotatable about its axis, the cassette mount being formed so as to be movable in an axial direction of the sample support carrier; a base to support the cassette mount in a parallelly displaceable mauler; a drive unit arranged at one side end of the base to drive and rotate the sample assembly and the sample support carrier on the cassette mount interlockingly; a rotating shaft of the drive unit to rotate the sample assembly on the cassette mount, the rotating shaft being adapted to move axially; a guide shaft connected to an end of the rotating shaft and adapted to move axially; and a biasing means connected to the guide shaft to apply a pulling bias force to the guide shaft at all times.

According to a ninth task achieving means, this invention provides a sample integration device according to the above means, wherein the biasing means is a coiled spring type biasing means.

According to a tenth task achieving means, this invention provides a sample integration device according to the above means, wherein the drive unit is provided with a handle for manual drive.

According to the first task achieving means of this invention associated with the sample integration cassette, since the relative position between the sample assembly and the sample support carrier is so set that the sample support is wound at a predetermined angle at all times, the sample support can be wound around the sample assembly uniformly and at a predetermined angle by interlockingly operating the sample assembly and the sample support carrier, thus improving a yield of the sample assembly and making the accommodation-reaction-measurement process more precise and easier.

According to the second task achieving means of this invention associated with the above sample integration cassette, the sample assembly can firmly hold the front end of the sample support from the beginning of the winding operation and can be wound with the sample support at high density without a slack. This can increase the sample integration density, contributing to a size reduction of the sample assembly and therefore the probe, which in turn leads to an overall size reduction of the measuring device and a reduced cost of the accommodation-reaction-measurement process.

According to the third task achieving means of this invention associated with the above sample integration cassette, the sample assembly can firmly hold the rear end of the sample support, minimize the required length of the sample support, eliminating its waste, and maintain a firmly wound state of the sample support by the secure holding of the front and rear ends of the sample support. This in turn increases the winding density of the sample support on the core surface, preventing a possible slack of the sample support during the accommodation-reaction-measurement process, facilitating the measurement and enhancing the measuring accuracy.

According to the fourth task achieving means of this invention associated with the above sample integration cassette, the relative position between the sample assembly and the sample support carrier can be maintained easily and the sample support can be wound around the sample assembly uniformly and at a predetermined angle, which in turn facilitates the spotting operation on the sample assembly and the sample integration into the sample assembly. As a result, the handling of the sample support becomes easy improving the work efficiency and reducing the manufacturing cost.

According to the fifth task achieving means of this invention associated with the above sample integration cassette, the sample assembly and the sample support carrier can be made to rotate in synchronism with each other during the sample assembling operation to give an appropriate tension to the sample support as it is wound on the sample assembly, thus allowing the sample support to be wound uniformly and at a predetermined angle.

According to the sixth task achieving means of this invention associated with the spotting device, simply lowering the delivery member mounted in the mounting portion of the movable table toward the sample support carrier can easily apply the samples to the sample support wound on the sample support carrier in a predetermined row and column matrix, thus enhancing the work efficiency.

According to the seventh task achieving means of this invention associated with the spotting device, the downward force needs only to be applied when lowering the delivery member toward the sample support carrier and the delivery member can be returned to its original position by the spring bias force, thus enhancing the work efficiency and lowering the cost.

According to the eighth task achieving means of this invention associated with the sample integration device, the sample assembly and the sample support carrier can be rotated synchronously and the sample assembly can be moved in the axial direction as the winding position changes. With this arrangement, the sample support can be given an appropriate tension during the winding operation, allowing it to be wound on the core of the sample assembly at high density.

According to the ninth task achieving means of this invention associated with the sample integration device, when the sample assembly no longer needs to be moved axially during the winding operation, it can be returned to its original position by the spring bias force, improving the work efficiency with a simple construction.

According to the tenth task achieving means of this invention associated with the sample integration device, the sample support can be wound manually, allowing the operator to choose an appropriate winding speed and deal flexibly with the situation during the work.

BEST MODE FOR IMPLEMENTING THE INVENTION

Now, embodiments of this invention will be described in detail. It is noted that the following detailed descriptions of embodiments are intended for better understanding of the present invention and in no way limits the scope of this invention unless otherwise specifically noted.

First Embodiment

Figure 1:
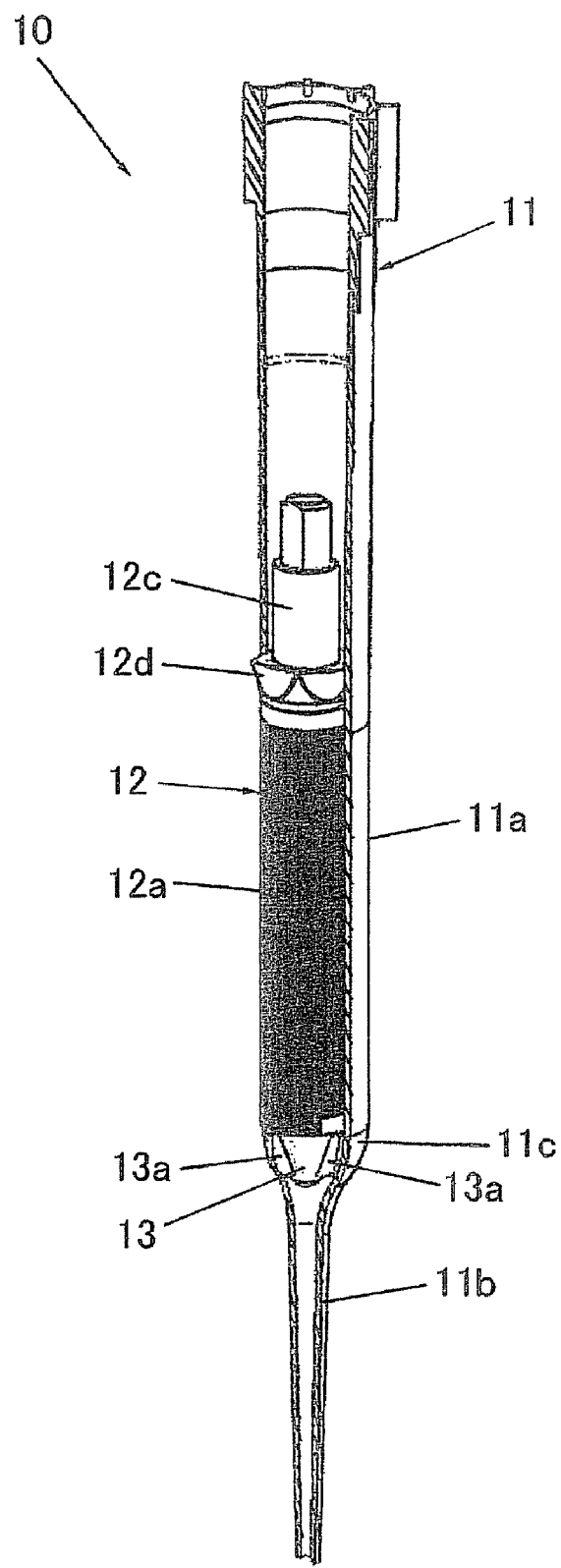
FIG. 1 is a partly cutaway perspective view showing a sample assembly with a spirally wound sample support accommodated in a pipette according to a first embodiment of this invention.
Figure 2:
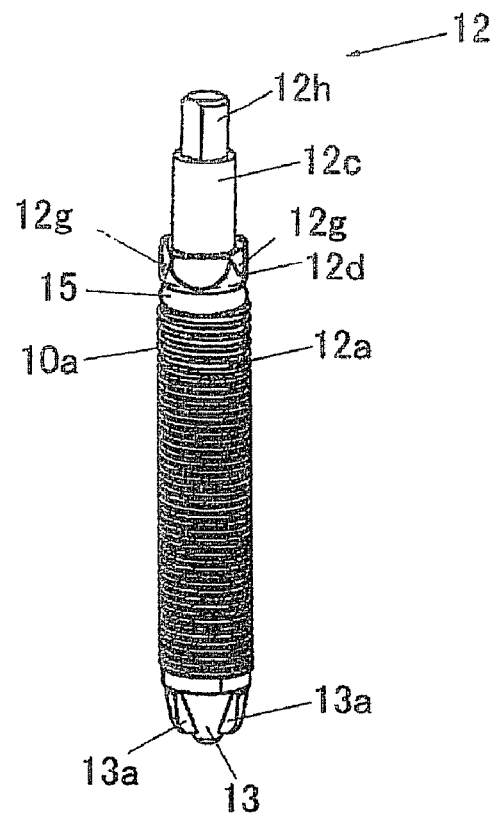
FIG. 2 is a perspective view showing the sample assembly having the sample support spirally wound on it.
Figure 3:
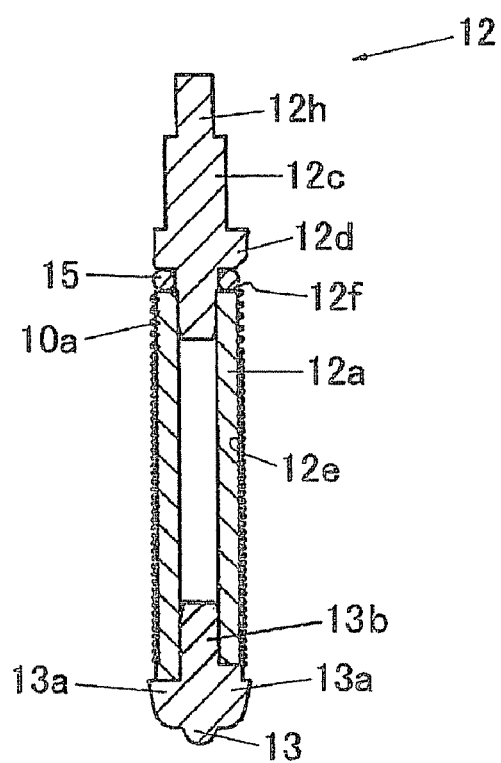
FIG. 3 is a vertical cross-sectional view showing the sample assembly having the sample support spirally wound on it.

As shown in FIG. 1 through FIG. 3, a probe 10 comprises a pipette 11 and a sample assembly 12 having a threadlike sample support 10a spirally wound around its circumferential surface. The pipette 11 is basically the same as the conventional one except that it is smaller in diameter and overall size than the conventional one.

The sample assembly 12, as shown in FIG. 2 to FIG. 5, is smaller in diameter and overall size than the conventional one and has an axially movable head 13 at the front end of the body. The body of the sample assembly 12 is formed cylindrical and has a core 12a and a handle 12c with its end fitted into the base end side of the core 12a. The core 12a is engraved in its outer circumferential surface with a spiral groove 12e along which the sample support 10a is wound.

The handle 12c comprises a front end side shaft portion fitted into the core 12a, a front end side stepped portion that, together with the rear end of the core 12a, forms an O-ring groove 12f, a flange portion 12d with raised parts 12g and whose transverse cross section is formed almost polygonal so that its engagement with an inner surface of a large-diameter portion 11a of the pipette 11 centers and positions the handle 12c in its place, a circular column portion situated at the central part of the handle, and a connecting portion 12h formed at the rear end of the handle for connection with other shaft member (e.g., shaft member 14 described later). The handle 12c, as described above, is a shaft member with its outer diameter changed in multiple steps.

A planar portion between the raised parts 12g of the flange portion 12d functions as a passage through which gas and liquid drawn in can flow easily.

The connecting portion 12h has its circumference partly cut away to form planar portions for rotary slip prevention and make its transverse cross section rectangular so that another shaft member with a hole of the similar cross section can fit over the connecting portion 12h, with their corresponding planar portions of the connecting portion 12h and of the hole of the shaft member engaged, and thereby transmit a rotating force without a relative slip.

The head 13 is formed conical with its diameter decreasing toward the front end which is rounded. The head 13 has a shaft member at the rear end that fits into the core 12a. On its outer conical surface the head 13 has arranged at equal intervals along its circumference a plurality of ribs 13a, . . . , 13a (four in the figure) so shaped that their outer contour matches a curved shape of a diameter shrinking portion 11c formed between the large-diameter portion 11a and the small-diameter portion 11b of the pipette 11. The head 13 formed as described above allows the sample suspending liquid drawn into the pipette 11 to pass between the ribs 13a, . . . , 13a and easily reach the core 12a of the sample assembly 12.

Further, the head 13, when moved toward the core 12a of the sample assembly 12, can hold the front end of the sample support 10a between it and the core 12a.

Figure 4:
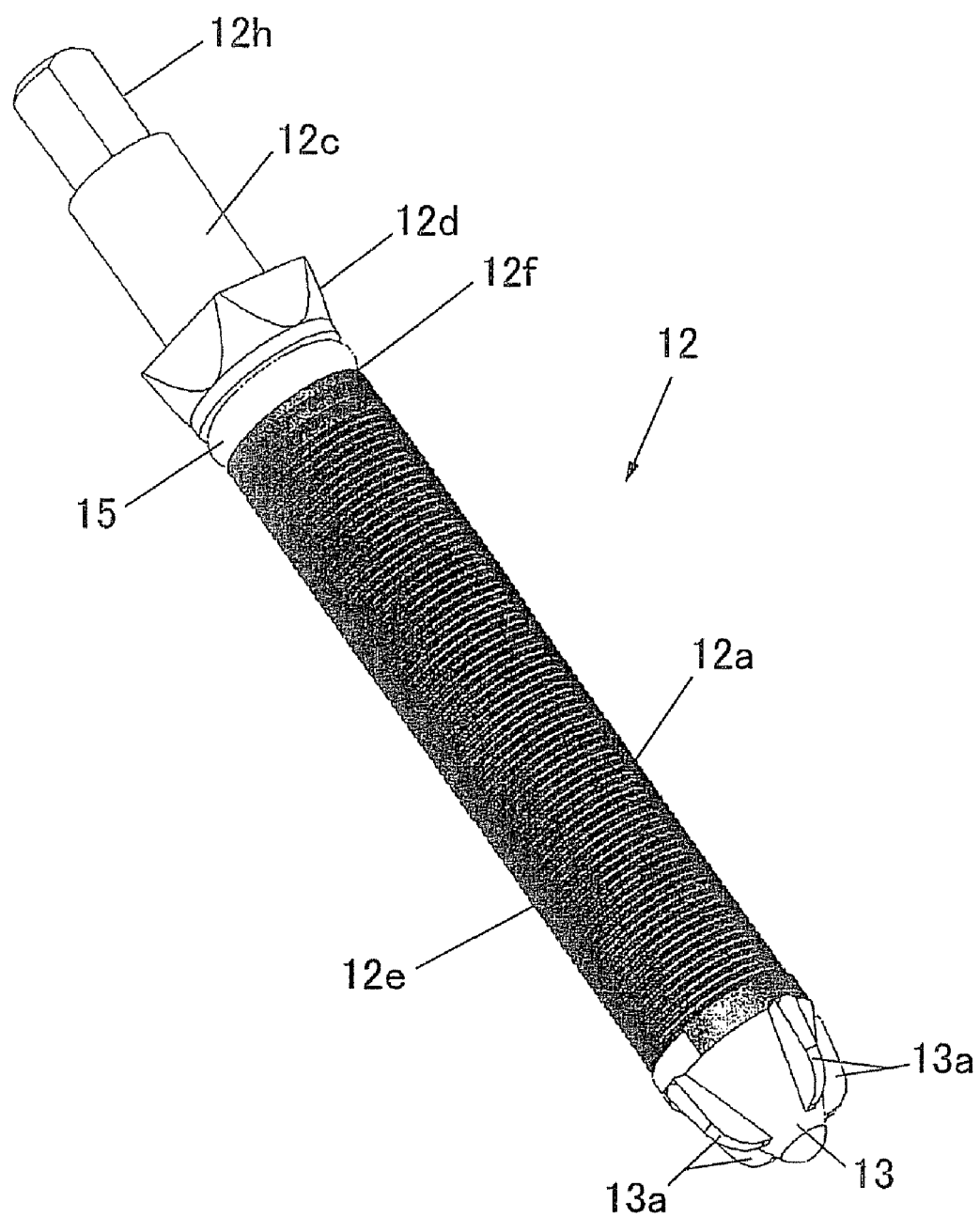
FIG. 4 is an enlarged perspective view of the sample assembly.
Figure 5:
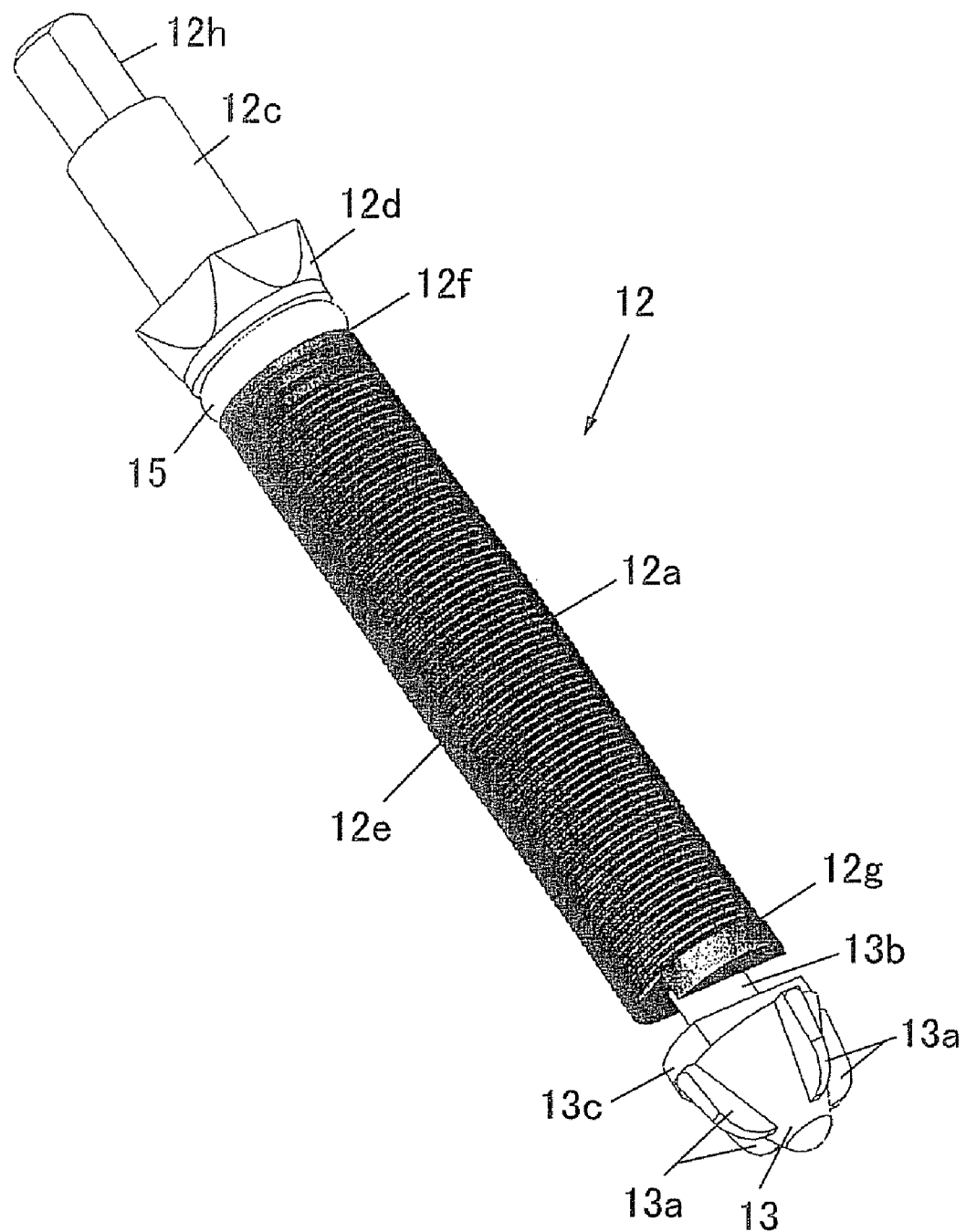
FIG. 5 is an enlarged perspective view showing a core and a head of the sample assembly separated from each other.

The core 12a of the sample assembly 12, as shown in FIG. 4 and FIG. 5, is engraved in its outer circumferential surface with a spiral groove 12e whose size is so set that the sample support 10a is buried one-third of its diameter with the remaining two-thirds protruding outside from the outer surface of the core. The groove 12e is formed in such a manner that its inclination angle is as small as possible and the interval between the adjoining grooves 12e is set as narrow as possible while keeping those parts of the sample support 10a protruding outside the outer surface of the core from contacting each other. The front end of the groove 12e is connected between the front end face of the core 12a and the rear end face of the head 13 to allow the front end of the sample support 10a to enter easily into the groove 12e from the clamped portion. The rear end of the groove 12e is connected to the O-ring groove 12f provided at the rear end of the core 12a so that the sample support 10a, when it enters the O-ring groove 12f, is held strongly against the wall surface of the core side of the O-ring groove 12f to maintain its tension, thereby preventing the wound sample support 10a from slacking. Since the sample support 10a is securely held at the front and rear ends of the core 12a, the wound sample support 10a can be maintained in a uniformly wound state under nearly the same condition over the entire length of the core 12a.

The head 13 capable of holding the front end of the sample support 10a, as shown in FIG. 3 to FIG. 5, is connected, axially movable, to the core 12a through the central shaft member 13b that coaxially fits into the core 12a. At the front end of the core 12a, a protrusion 12g crescent-shaped in transverse cross section protrudes axially forward. At the rear end of the head 13 a protrusion 13c crescent-shaped in cross section protrudes axially rearward and, when combined with the protrusion 12g, forms a circular column.

With the front end of the core 12a and the rear end of the head 13 formed as described above, when the head 13 is moved toward the core 12a, the protrusions 12g, 13c combine to form a circular cylinder defining the outer shape of the core 12a. As a result, the core 12a and the combination of the protrusions 12g, 13c form one cylindrical member of a uniform diameter, with the head 13 attached to the front end of the cylindrical member.

Then, as shown in FIG. 5, by moving the head 13 to separate the rear end face of the head 13 from the front end face of the core 12a, the front end of the sample support 10a can be placed in a gap between the separated front and rear end faces. As shown in FIG. 4, the head 13 is then moved to engage its rear end face with the front end face of the core 12a to firmly hold the front end of the sample support 10a between the two members so that it cannot be pulled out.

With the front end of the sample support 10a firmly clamped between the front end face of the core 12a and the rear end face of the head 13, the sample support 10a can easily be wound on the core 12a.

The sample support 10a is an object material to which sample suspending liquids are applied for sample fixing, and which is formed of a threadlike, flexible material so that it can be wound or unwound. The sample support is long enough to cover the samples corresponding to all elements of the matrix and its thickness is preferably in a range of between about 10 μm and several millimeters.

To ensure that the samples suspended in the liquids to be applied are effectively arrayed, the sample support itself needs to be formed of a material having pores, roughened surface or foams, or to be surface-treated as by covering and impregnation. These properties are preferably chosen according to the samples to be applied. For example, possible materials for the sample support include nylon treated with HCl and formic acid, cellulose, nitrocellulose, glass fibers, chitosan, epoxy resin, monofilament support, and silk and cotton threads entangled with fibers.

It is preferred that the sample support 10a have biologically activated molecules fixed therein in multiple layers. Such functional groups may include —NH2, —COOH and those aminated by nucleophilic reagents.

It is also preferred that samples applied to the sample support 10a be fixed by a drying method, UV cross ring, PVA crosslinking method, UV crosslinking resin, etc. depending on the property of the samples.

The sample support 10a is wound on the sample support carrier 3 and applied with predetermined sample suspending liquids to fix the samples in the support. After this, it is unwound from the sample support carrier 3 and wound around the sample assembly 12.

Among the samples used, there are biological substances, such as nucleic acid, polynucleotides, oligonucleotides, proteins, saccharides, immunosubstances, biopolymers such as hormones, and biomonomers. The samples also include beads to which biological substances adhere.

Figure 6:
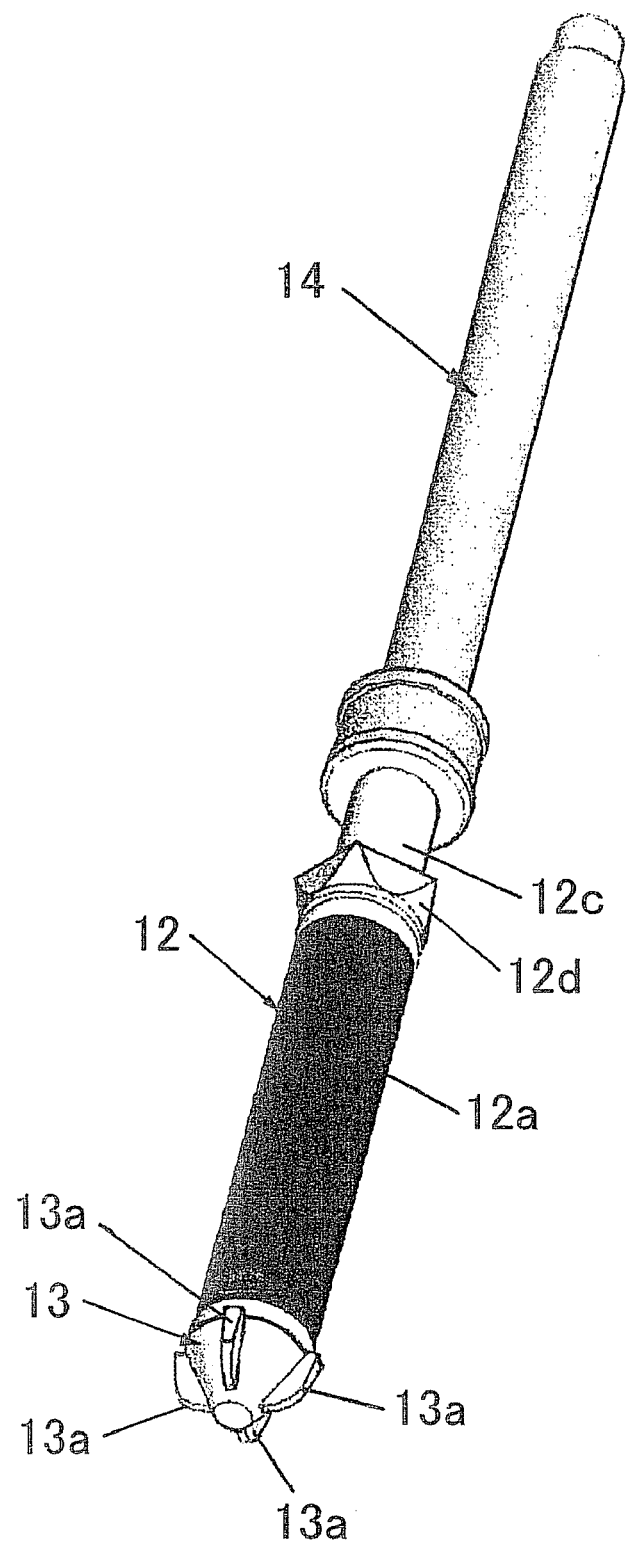
FIG. 6 is a perspective view showing a shaft member fitted to the sample assembly.

The sample assembly 12 in a state before being put in the pipette 111 is not used as is. As shown in FIG. 6, the shaft member 14 to be mounted on the cassette is coaxially connected to the sample assembly 12 by fitting a hole (not shown) in the front end of the shaft member 14 over the connecting portion 12h of the handle 12c at the base of the sample assembly 12.

In the following figures, since the sample support 10a is too fine to be clearly recognized because of its relative size with respect to the components or devices, it is not shown in the drawings.

Figure 7:
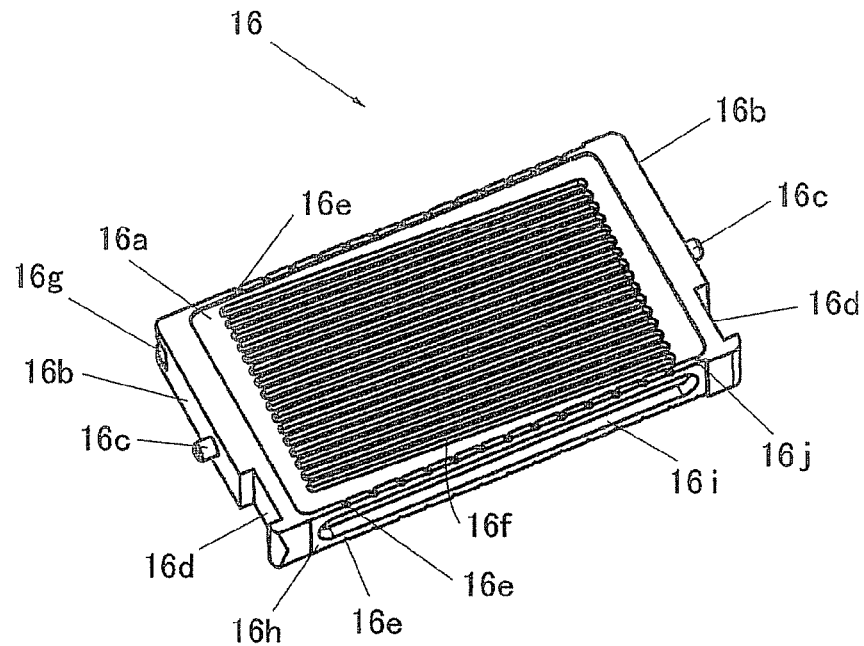
FIG. 7 is a perspective view showing a sample support carrier on which the sample support is wound according to the first embodiment of this invention.

The sample support carrier 16 used to apply and fix samples to the sample support 10a has, as shown in FIG. 7, shaft members 16c, 16c protruding from a central part of end faces 16b, 16b on both short sides. These end faces 16b, 16b are formed with rectangular notches 16d, 16d at peripheral parts on one side of the shaft members 16c, 16c. On its upper and lower surfaces, the sample support carrier 16 has V-shaped grooves 16e, . . . , 16e engraved at equal intervals along the edges on both long sides thereof and staggered by half-pitch between the two long sides.

In the upper and lower surfaces of a plate 16a, a plurality of narrow slots 16f, . . . , 16f (16 slots in the figure) piercing from each surface into a hollow portion are parallelly formed at an angle to the center line of the shaft members 16c, 16c. The width of each slot 16f, . . . , 16f is so set that a tension applied longitudinally to the sample support 10a—that is wound around the plate in the slot width direction—by the pressing force of a delivery member 17 described later during liquid application is enough to adhere the liquids to the sample support. The inclination angle of the slots 16f, . . . , 16f is preferably set almost perpendicular to or at a preset angle to the inclination angle of the groove 12e of the sample assembly 12. The inclination angle of the slots 16f, . . . , 16f may also be represented by an angle to the peripheral edges of the longer sides formed with the V grooves 16e, . . . , 16e. In that case, the inclination angle of the slots 16f, . . . , 16f should be such that the sample support wound on the V grooves 16e, . . . , 16e formed in the peripheral edges on both longer sides crosses the slots 16f, . . . , 16f at right angles.

The size of the sample support carrier 16 is determined by setting the size of the plate 16a, the positions of the slots 16f, . . . , 16f and the positions of the V grooves 16e, . . . , 16e according to the positions of arrayed protruding members 17b of the delivery member 17 described later and to the size of the array.

At a corner on that side of each end face 16b, 16b opposite the side where the notches 16d, 16d are formed, the sample support carrier 16 is engraved with a groove 16g that engages a rotation prevention means.

Further, in at least one of end faces 16h connecting almost at right angles to the end faces 16b, 16b which is closer to the notches 16d, 16d, the sample support carrier 16 is formed with a narrow slot 16i piercing from the end face 16h into the hollow portion. The slot 16i provides a spotting position where a liquid suspending a reagent as a marker is applied to the sample support 10a that is wound on the sample support carrier 16 to cross the slot 16i through the V grooves 16e, . . . , 16e.

At a corner of the sample support carrier 16 is formed a slit 16j in which to hold the front end of the sample support 10a.

To wind the sample support 10a around the sample support carrier 16, the front end of the sample support 10a is knotted. With the knot caught in the slit 16j, the sample support 10a is passed through one V groove 16e, then the next V groove and so on in a predetermined winding order.

Those portions of the sample support carrier 16 that are wound with the sample support 10a are formed with engineering plastics, such as polycarbonate, polyvinyl acetate, polyethylene and polypropylene, or glass fiber reinforced plastics.

Figure 8:
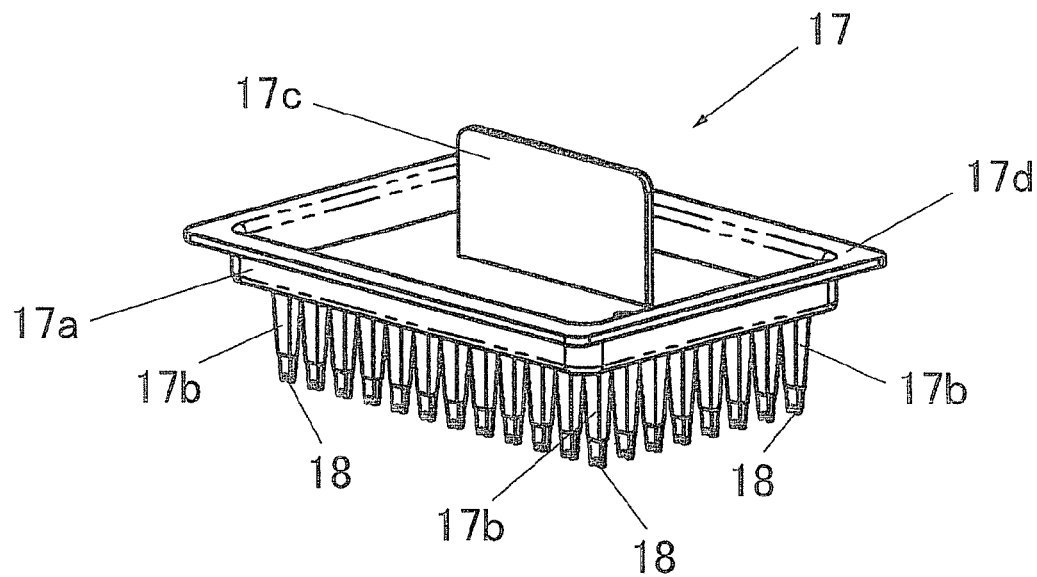
FIG. 8 is a perspective view showing a delivery member according to the first embodiment of this invention.
Figure 9:
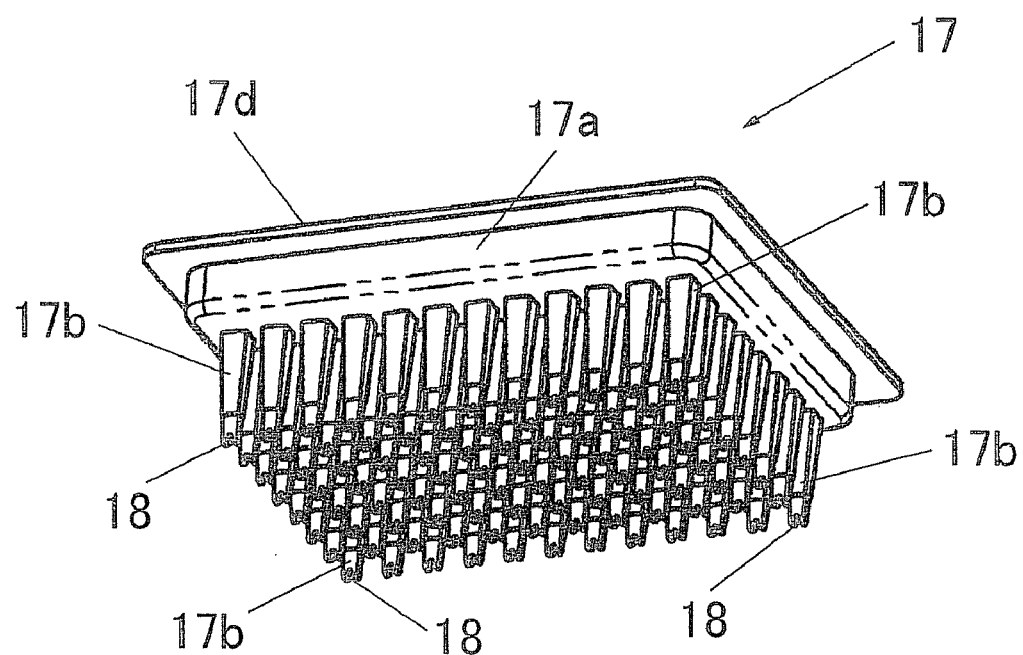
FIG. 9 is a perspective view showing the delivery member as seen from below.
Figure 10:
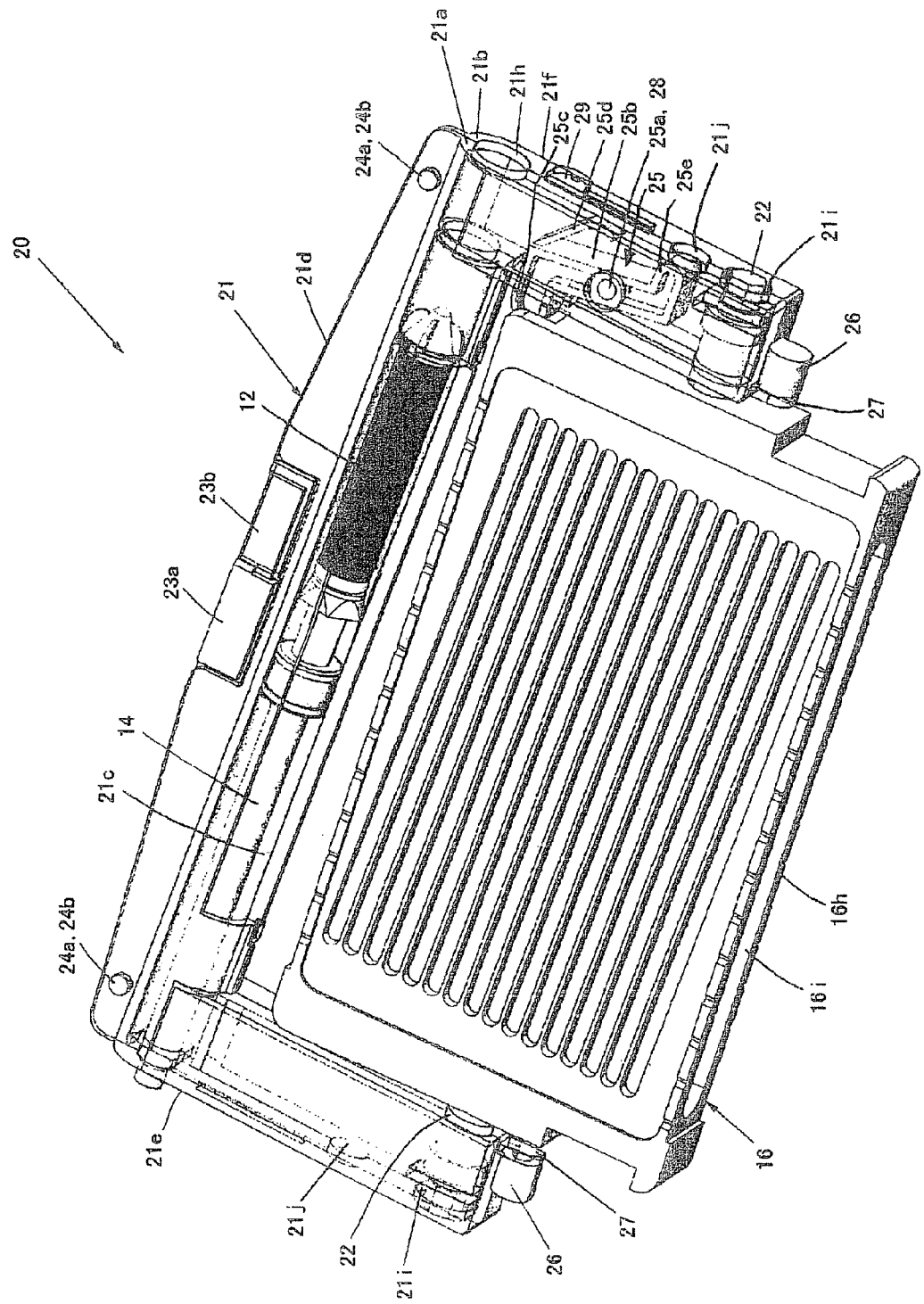
FIG. 10 is a perspective view showing a sample integration cassette according to the first embodiment of this invention.
Figure 11:
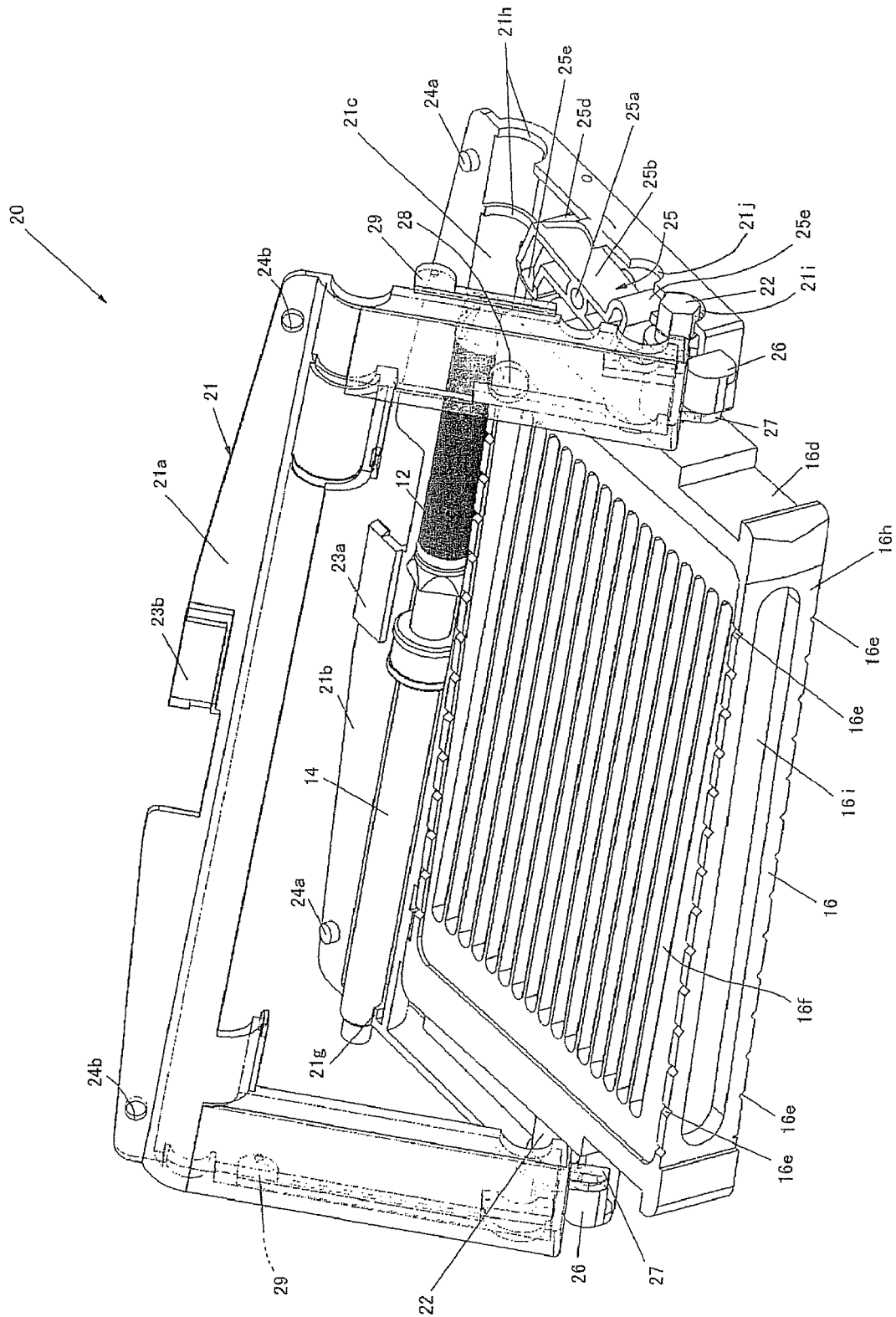
FIG. 11 is a perspective view showing the sample integration cassette being assembled.
Figure 12:
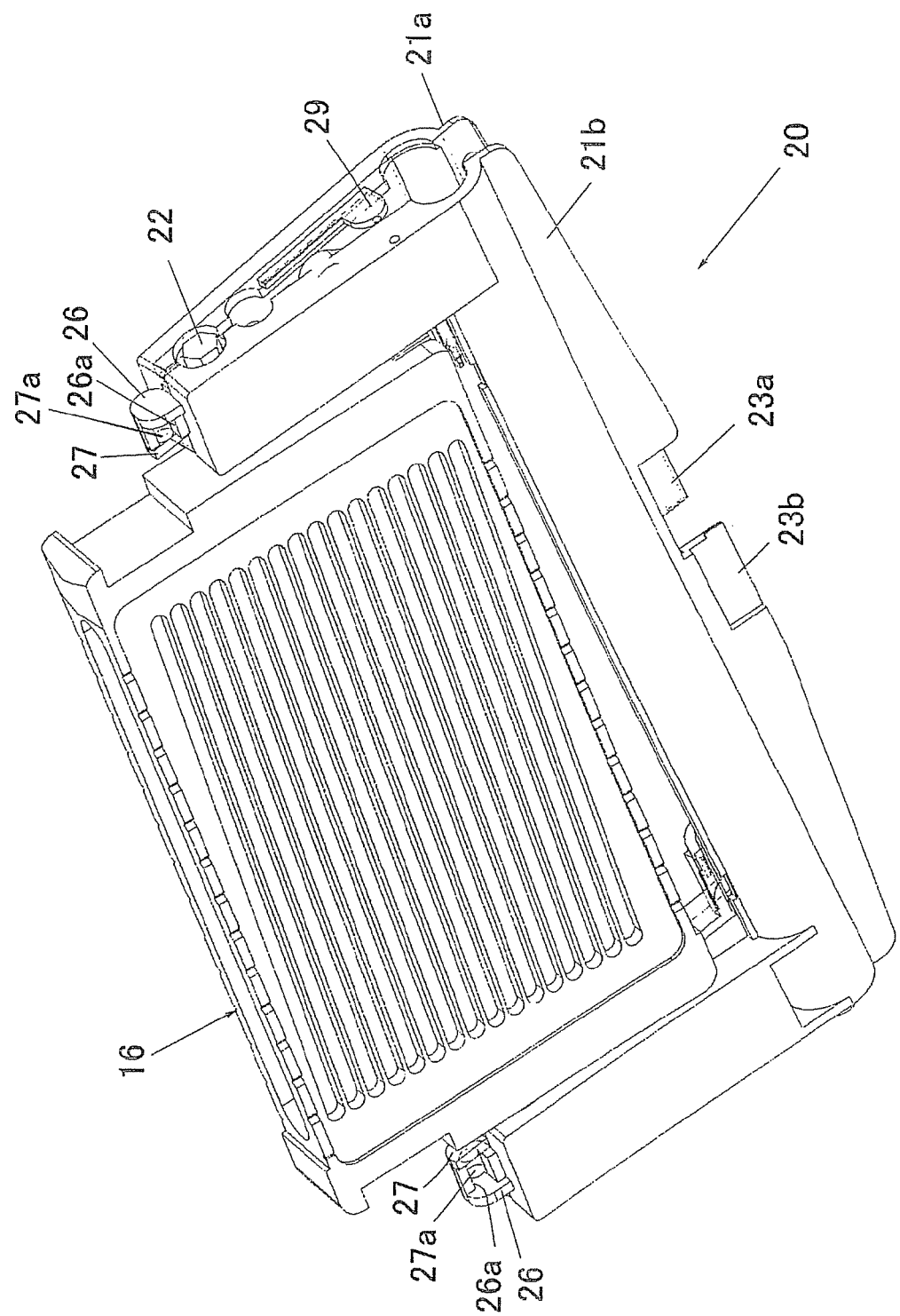
FIG. 12 is a perspective view showing the sample integration cassette just before the completion of its assembly as seen from below.

The delivery member 17 used to apply reagent suspending liquids to the sample support 10a, which is wound around the sample support carrier 16 through the V grooves 16e, . . . , 16e formed in the edges of the long sides of the sample support carrier 16, has rodlike protruding members 17b, . . . , 17b vertically extending downward from the underside of its body 17a, as shown in FIG. 8 and FIG. 9. The protruding members 17b, . . . , 17b have their front end formed to be able to hold a small amount of sample suspending liquids. On the upper surface (opposite the surface where the protruding members are arranged), a platelike grip member 17c to be held by hand is erected. Along the side peripheral surface of the body 17a is formed a steplike flange 17d.

The protruding members 17b, . . . , 17b, as shown in FIG. 9, are arrayed at specified intervals in two directions, row and column directions, and extend vertically downward. The front end of each protruding member is formed with a combination groove 18 which comprises a V-shaped groove opening toward the front end side and a U-shaped groove of a smaller width that is engraved into the deepest part of the V-shaped groove, making it possible for the combination groove 18 to hold the liquid.

The configuration of the end of each protruding member 17 is not limited to the combination groove 18. A groove or recess extending along the sample support to increase a contact area with the liquid may be provided at the front end. It is also preferable to form a slit or hole in the front end like a pen point or to form the front end into an almost J-shaped or V-shaped configuration or a pointed configuration, to enhance a liquid holding capability. Further, the front end may have, at its tip or in the entire end portion, a liquid soaking material with pores, roughened surface or foams. The front end may also be formed into a cylinder, tube or donut shape with a hollow interior.

The array of the protruding members 17b, . . . , 17b in the predetermined row and column matrix represents a state in which the protruding members 17b, . . . , 17b are arranged at predetermined intervals of the wells in the microplatelike vessel so that they can be inserted into the arrayed wells. The array preferably conforms to global standards of, for example, a 48-hole microplate (6 rows×8 columns), a 96-hole microplate (8 rows×12 columns), a 384-hole microplate (16 rows×24 columns) and 1536-hole microplate (32 rows×48 columns).

Further, when they are in the predetermined row/column matrix, all the protruding members 17b, . . . , 17b vertically extending downward from the underside of the body 17a are shifted to one side by half a pitch so that, by reversing the left and right side of the delivery member 17, liquids can be applied to intermediate positions between the positions of previously applied sample suspending liquids. This can reduce the liquid application intervals by half when compared with the conventional devices, doubling the distribution density of the sample suspending liquids.

The size of the delivery member 17 is determined so that the number of the protruding members 17b, . . . , 17b is one-fourth that of the wells arrayed in the microplatelike vessel. According to the positions of the protruding members 17b, . . . , 17b and the size of the array, the size of the plate 16a, the positions of the slots 16f, . . . , 16f and the positions of the V grooves 16e, . . . , 16e in the sample support carrier 16 are set so that the protruding members 17b, . . . , 17b can apply, four times in all, the sample suspending liquids to the sample support 10a on the front and back of the sample support carrier 16.

The delivery member 17 may be formed as a disposable component or as a component that can be washed for reuse.

The end of the protruding members 17b, . . . , 17b may be formed of plastics, such as polycarbonate, polyvinyl acetate, polyethylene, polypropylene, polysulfone, polyvinylidene 2-fluoride and Teflon (registered trademark), nonmetals such as glass, or metals such as aluminum and titanium.

In other than the end portion, the protruding member 17b is preferably coated with polymer coating, especially Teflon (registered trademark) or silicon, to give the surface a hydrophobicity to prevent the sample suspending liquids from adhering to areas adjoining the end portion. Further, the end portion is preferably formed in a way that allows the delivered sample to contact the entire circumference of the sample support at each sample application position.

The body 17a of the delivery member 17 is formed in such a shape and dimension that it can be fitted into a holder portion 43c formed in a delivery member mounting table 43 of the spotting device (see FIGS. 14 and 15) described later.

The sample assembly cassette 20 comprises a cassette jig 21 formed of a transparent or translucent material in which the sample assembly 12 and the sample support carrier 16 are set, as shown in FIG. 10 to FIG. 13. The cassette jig 21 is divided into an upper cover 21a and a lower cover 21b that together form an outer shell. With the upper cover 21a removed, the sample assembly 12 fitted with the shaft member 14 which has yet to be wound with the sample support and the sample support carrier 16 not yet wound with the sample support 10a are assembled. In this state, the sample support 10a payed out from a bobbin (not shown) is wound around the sample support carrier 16. First, the front end of the sample support 10a is secured to the slit 16j. Then, the sample support 10a is led onto a side surface opposite the one where the slit 16j is formed, and then passed through the nearest V groove 16e. The sample support 10a is further led to the opposite side and passed through the corresponding V groove 16e. It is again wound around the opposite side surface, passed through the next V groove 16e, then led to the opposite side surface and passed through the corresponding V groove 16e. This process is repeated until the sample support 10a is wound and passed through all V grooves 16e formed in the longer sides of the sample support carrier. Then, a part of the sample support 10a near the position where it is to be cut is pushed down between the core 12a of the sample assembly 12 and the head 13. The head 13 is pushed against the front end of the core 12a to strongly clamp the sample support 10a. An excess part of the sample support 10a protruding on the side opposite the sample support carrier 16 is cut off in immediate proximity to the clamped position. Then the upper cover 21a is attached and now the sample assembly cassette 20 is complete.

The cassette jig 21 is formed in a shape of gate, comprised of a center member 21d having an accommodation hole 21c in which to rotatably accommodate the sample assembly 12 and side support members 21e, 21f projecting almost perpendicularly from the ends of the center member 21d. Rotating shafts 22 fitted over the shaft members 16c, 16c of the sample support carrier 16 are rotatably fitted into each of the side support members 21e, 21f. As a result, the sample support carrier 16 can be rotatably mounted to the cassette jig 21.

The cassette jig 21 is formed with a hole 21g at one end of the center member 21d and, at the other end, with holes 21h, 21h. The hole 21g communicates with the accommodation hole 21c and functions as a bearing in which the shaft member 14 connected to the sample assembly 12 is rotatably supported. The holes 21h, 21h are also communicated to the accommodation hole 21c and accepts a tool that drives the head 13 toward the core 12a to hold the end of the sample support 10a between them. Further, on the outside of the accommodation hole 21c, the center member 21d is formed with clampers 23a, 23b that help to assemble or disassemble the upper cover 21a and the lower cover 21b. The center member 21d also has protrusions 24a and holes 24b for the positioning of these covers.

One of the side support members, 21f, pivotally supports a stopper 25 that prevents the rotation of the sample support carrier 16. The stopper 25 has at its center a shaft support portion 25b formed with a shaft hole 25a. At one end the stopper 25 has an engagement end 25c protruding toward the sample support carrier 16 side. On the back of the engagement end 25c a leaf spring 25d is installed to urge the engagement end 25c toward the sample support carrier 16 side. At the other end the stopper 25 has an engagement end 25e formed on the same surface that the leaf spring 25d engages, the engagement end 25e being adapted to be pushed by a rod to disable the rotation prevention function.

The outer surfaces of the side support members 21e, 21f are formed with holes 21i, 21i in which to fit a tool that engages the rotating shafts 22 to rotate the sample support carrier or in which to fit a sample support carrier rotating shaft of the spotting device. The outer surfaces are also formed with holes 21j, 21j in which to insert a tool that engages the engagement end 25e of the stopper 25 to disable the rotation prevention function or to insert a pin of the spotting device.

At the front end of the side support members 21e, 21f on the lower cover 21b side, an hole side protruding member 26 for engagement is provided which has a horizontally extending shaft hole 26a therein that is open in the lower side surface and in the inner side end face. At the front end of the side support members 21e, 21f on the upper cover 21a side, a shaft side protruding member 27 for engagement is provided which has a horizontally extending shaft 27a that engages the hole side protruding member 26 on the lower cover 21b side.

The upper cover 21a has retainer members 29, 29 protruding from the outer side surfaces at a position where a shaft 28 to be inserted into the shaft hole 25a of the stopper 25 projects toward the stopper. The retainer members 29, 29 hold the lower cover 21b from both outer sides, thus determining the positions of the upper and lower covers 21a, 21b.

Figure 13:
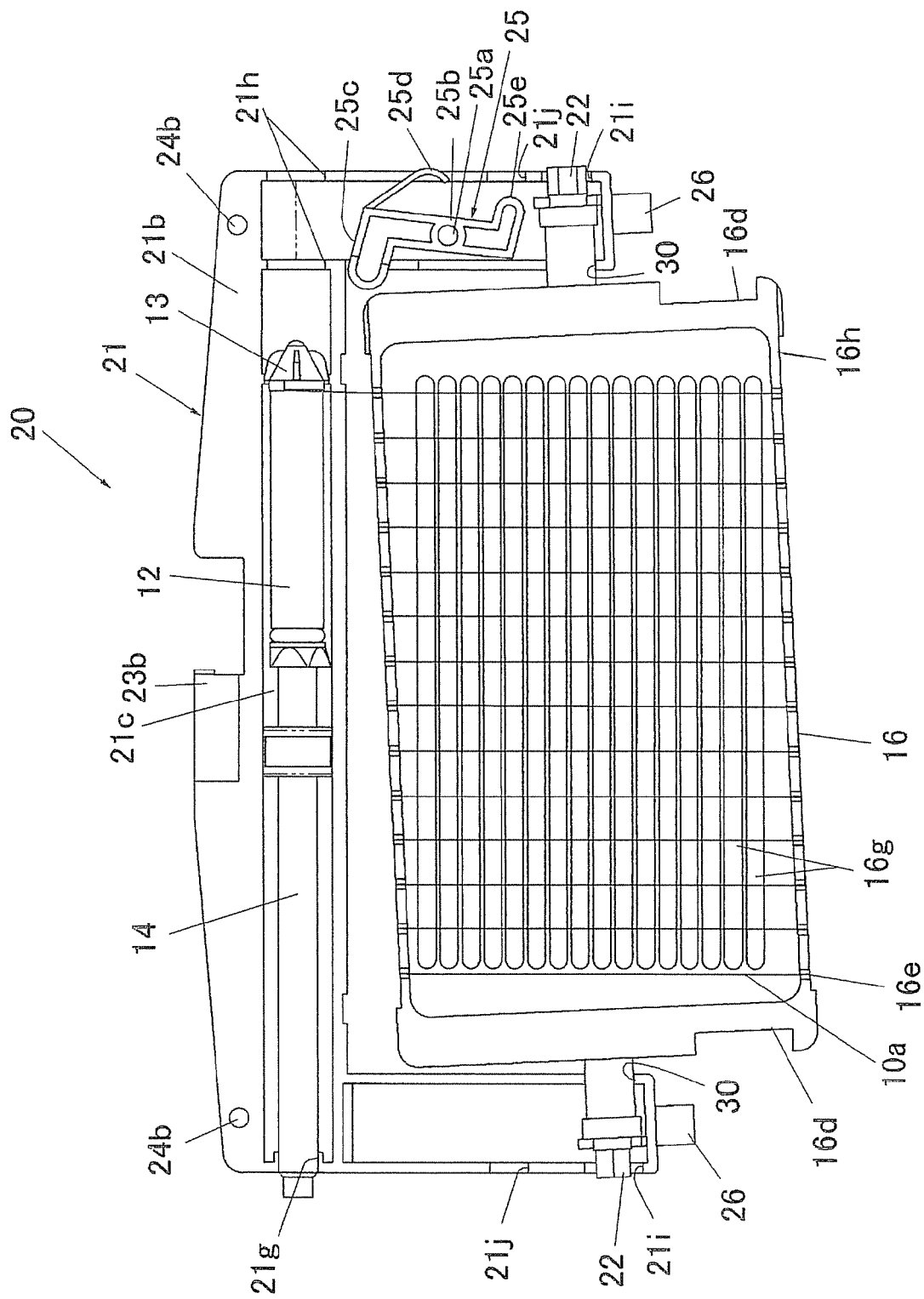
FIG. 13 is a plan view showing a positional relation between the sample assembly and the sample support carrier in the sample integration cassette and a state in which the sample support is wound.

In the sample assembly cassette 20 having its cassette jig 21 fitted with the sample assembly 12, that has yet to be wound with the sample support 10a, and with the sample support carrier 16 already wound with the sample support 10a, as shown in FIG. 13, the side support members 21e, 21f are formed with rotating shaft support holes 30, 30. The rotating shaft support holes 30, 30 allow the sample support carrier 16 to be installed at an inclination angle that matches the inclination angle of the groove 12e of the sample assembly 12 in which to lay the sample support 10a so that the axis of the sample assembly 12 is almost parallel to the slots 16f, . . . , 16f of the sample support carrier 16.

Figure 14:
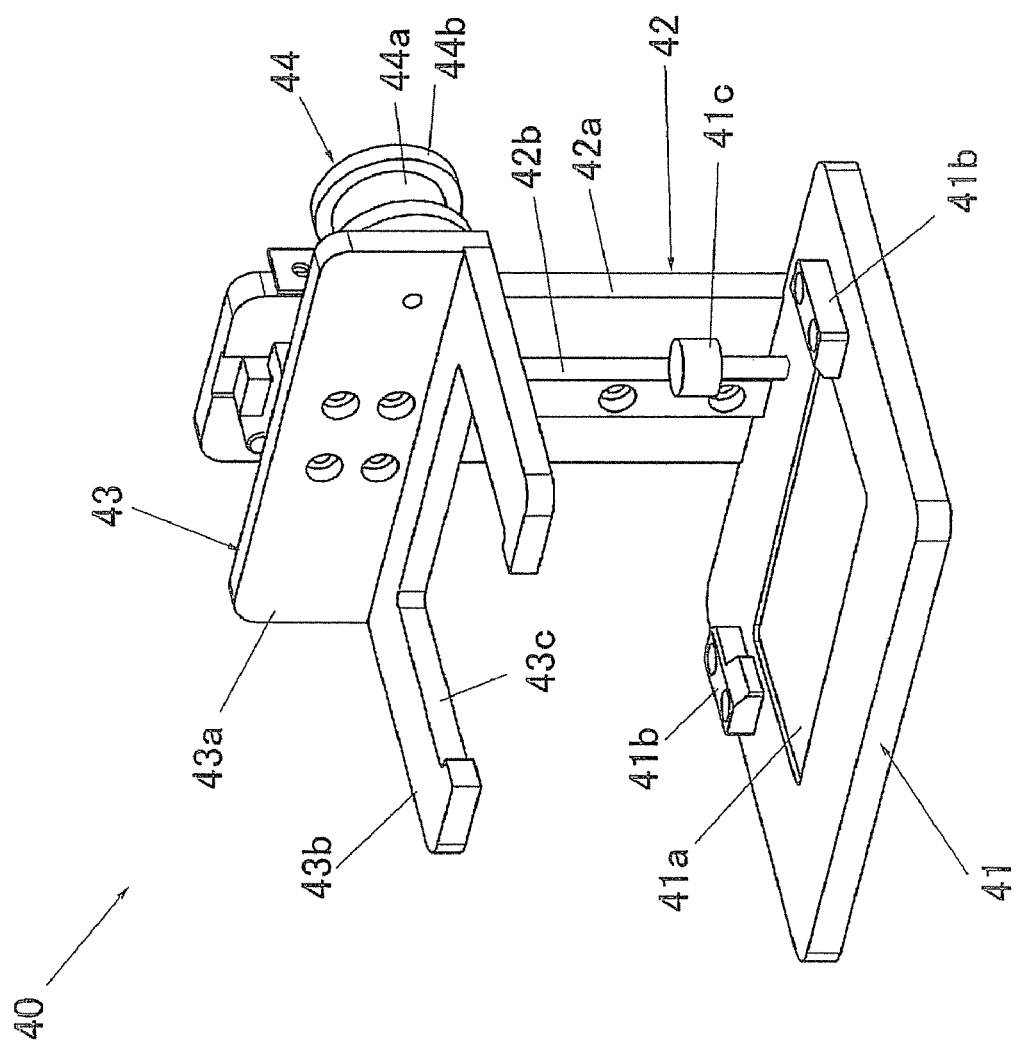
FIG. 14 is a perspective view showing a spotting device according to the first embodiment of this invention.

A spotting device 40 to apply sample suspending liquids, in a predetermined row and column matrix, to the sample support 10a wound on the sample support carrier 16 in the cassette 20 comprises, as shown in FIG. 14, a platelike base 41 rectangular in plan view, a stand 42 erected from a central part of one longer side of the base, a movable table 43 that is vertically moved along the stand 42, and a spring device 44 that applies a spring bias force to the movable table 43 so that the movable table 43 is always urged toward the top of the stand 42.

The base 41 has a cassette mount 41a formed in the upper surface on which to place the cassette and which is a planar portion slightly recessed in the upper surface according to the size of the cassette; a pair of positioning members 41b, 41b situated at both ends of one of longer sides of the cassette mount 41a; and a stopper 41c erected from the base 41 near the lower end of the stand 42 to limit a lowered position of the movable table 43.

The positioning members 41b, 41b have an inclined surface formed on opposing surfaces in order to guide the cassette and other components, such as microplatelike vessels, so that they can easily be set at a predetermined position.

Figure 15:
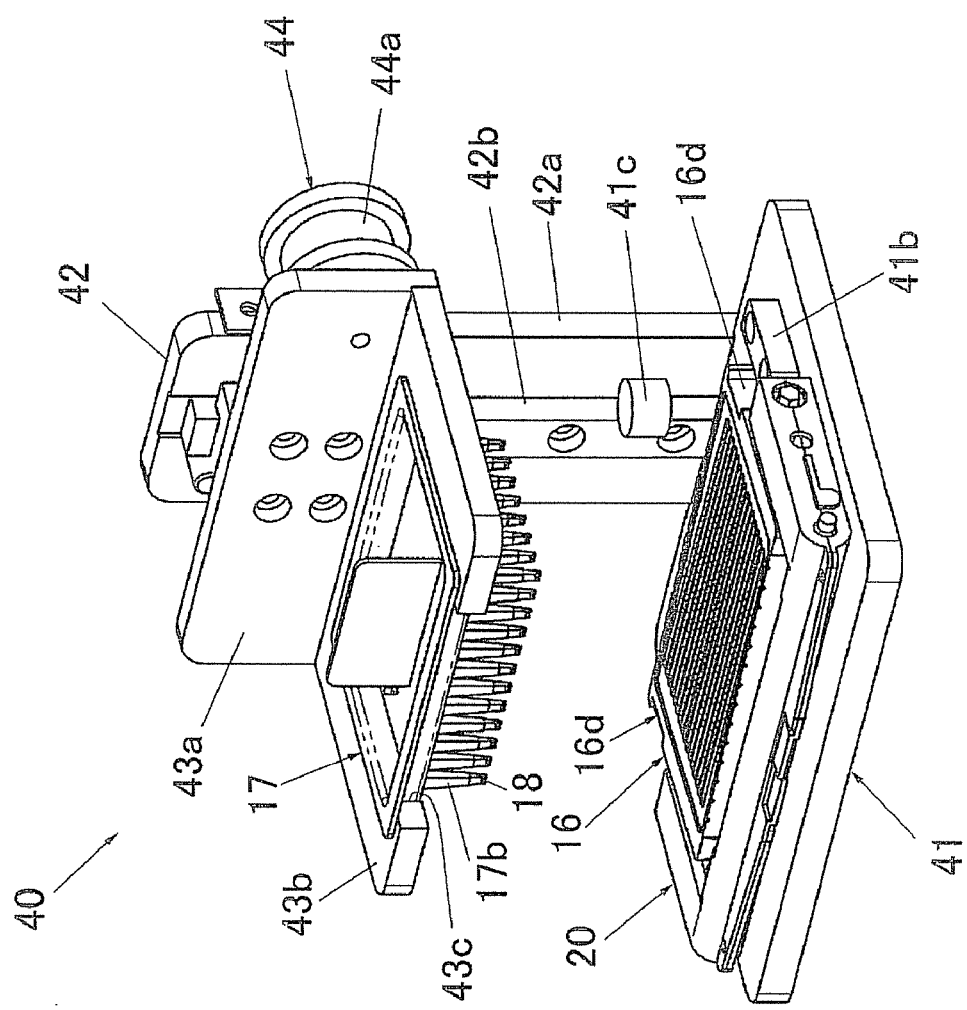
FIG. 15 is a perspective view showing the cassette and the delivery member mounted on the spotting device.

The stand 42, as shown in FIG. 14 and FIG. 15, is provided with a guide rail 42b on its surface facing the base side to guide the movable table 43 in a straight line as it slides vertically. To the side surface of the stand body 42a a front end of a coiled spring 44a of the spring device 44 is secured, so that when the movable table 43 is lowered elongating the coiled spring 44a, the bias force of the coiled spring 44a acts to move the movable table 43 up to the original position.

The movable table 43 has a movable table body 43a that is slidably fitted to the guide rail 42b, a spring bobbin 44b rotatably installed at the back of the movable table body 43a and around which the coiled spring 44a is wound; and a delivery member mounting table 43b shaped like a gate in plan view and projecting horizontally from the front side of the lower end of the movable table body 43a.

The delivery member mounting table 43b has a gate-shaped central space formed in such a size and configuration that it can be used as a holder portion 43c in which to fit the delivery member 17 from above.

As shown in FIG. 15, the stand 42 is used as follows. The cassette 20 is put on the cassette mount 41a and the delivery member 17 holding the sample suspending liquids at the front ends of the protruding members 17b, . . . , 17b is fitted in the holder portion 43c of the delivery member mounting table 43b. Then, simply lowering the movable table 43 until it engages the stopper 41c can apply the sample suspending liquids, in a predetermined row and column matrix, to the sample support 10a wound on the sample support carrier 16 installed in the cassette. After the movable table 43 has been lifted by the force of the coiled spring 44a, the delivery member 17 is taken out and then the delivery member 17 holding new sample suspending liquids is reversed between its left and right side before being fitted again. The movable table 43 is lowered again until it abuts against the stopper 41c. As a result, the new sample suspending liquids are additionally applied to the sample support 10a—which is already attached with sample suspending liquids in a predetermined row and column matrix—at intermediate positions between the previously applied sample suspending liquids.

After this, the movable table 43 is moved up, the delivery member 17 is taken out, the sample support carrier 16 installed in the cassette 20 is turned upside down and set again in the cassette mount 41a. The above procedure is repeated to apply sample suspending liquids in a predetermined row and column matrix. This is followed by reversing the left and right side of the delivery member 17 in order to apply new sample suspending liquids also at intermediate positions between the previously applied sample suspending liquids. This process allows sample suspending liquids to be applied to the sample support 10a at high density.

Figure 16:
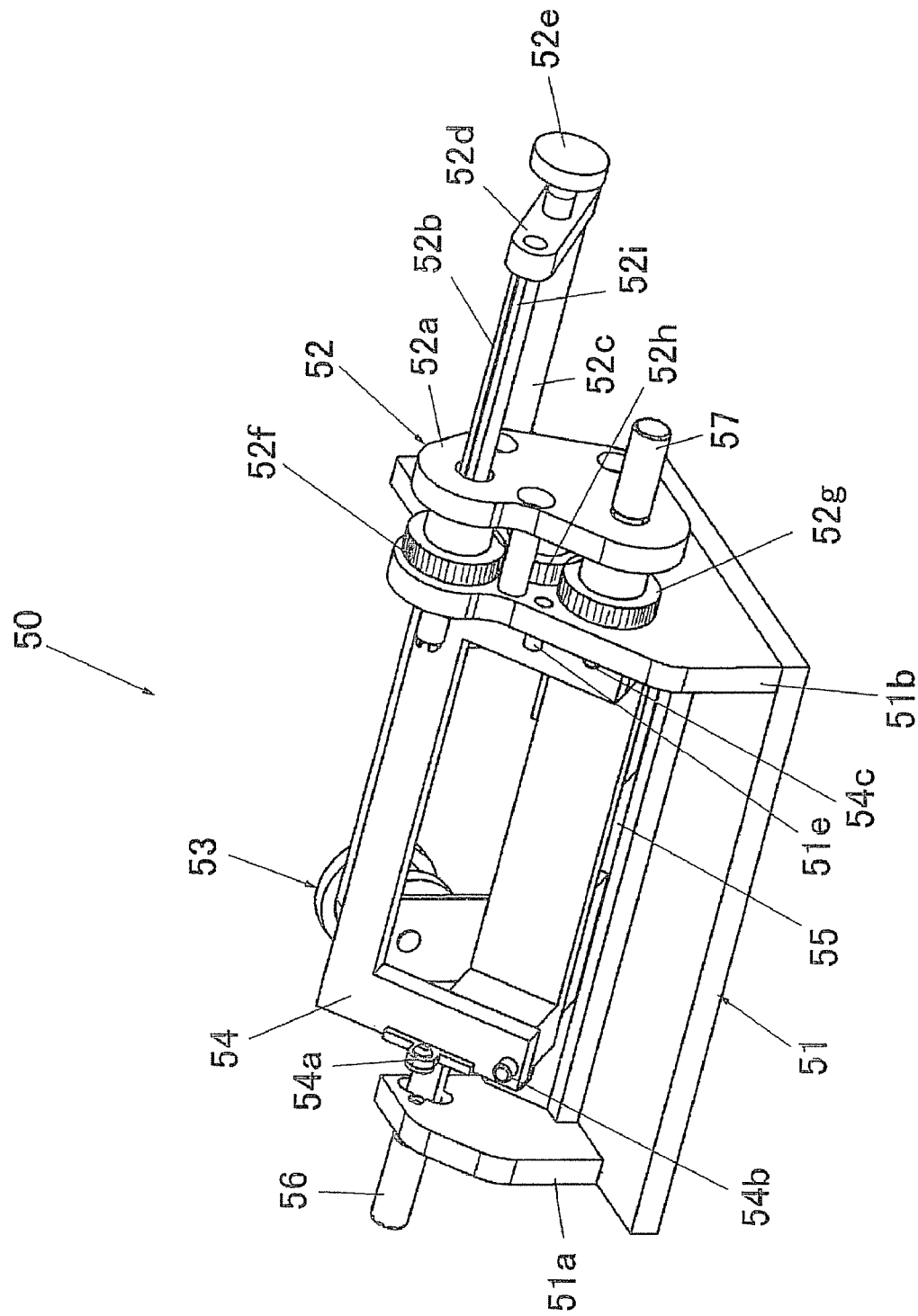
FIG. 16 is a perspective view showing a sample integration device according to the first embodiment of this invention.
Figure 17:
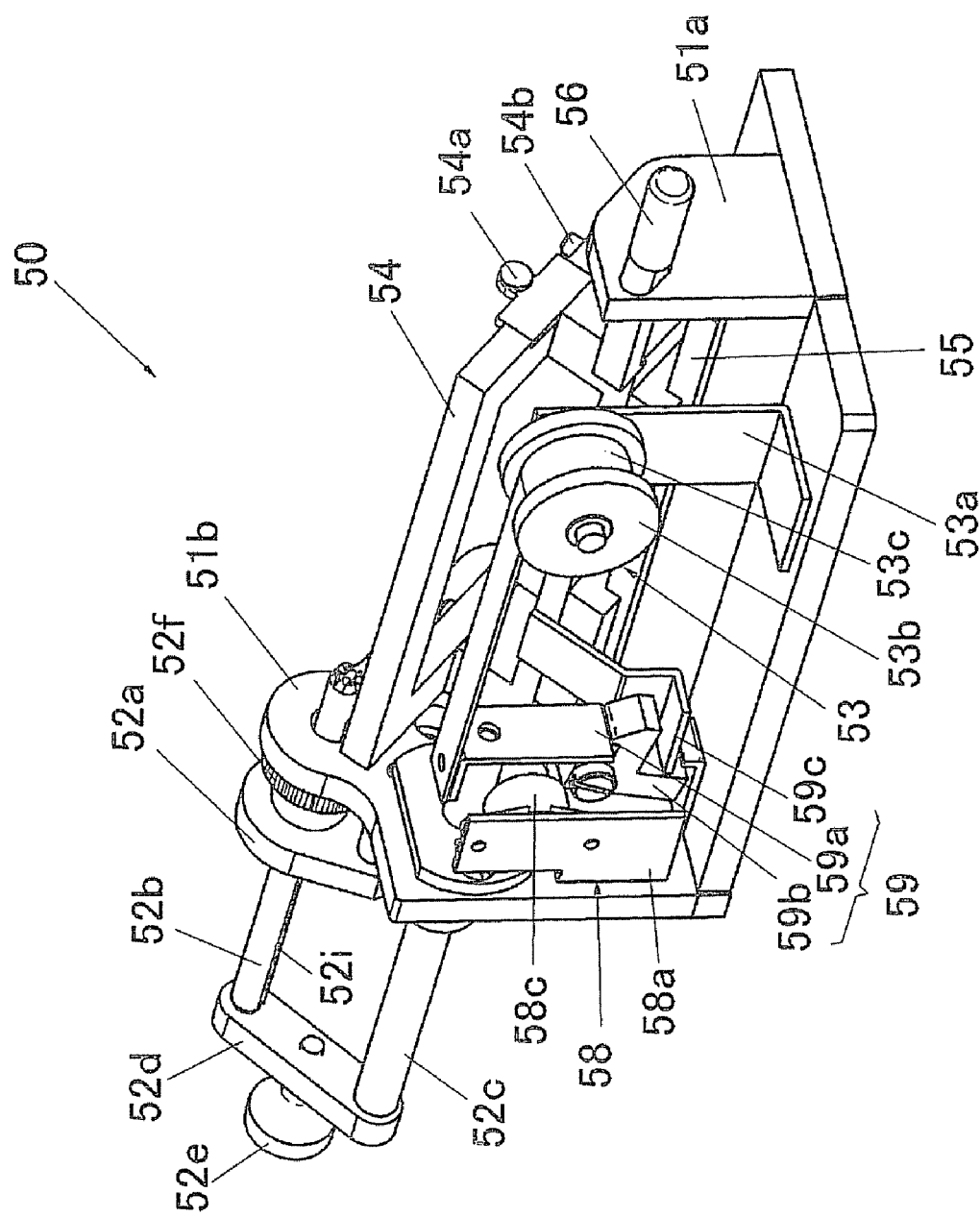
FIG. 17 is a perspective view of the sample integration device as seen from the back.

The sample integration device 50, as shown in FIG. 16 and FIG. 17, comprises: a base 51 having side walls 51a, 51b erected at both sides so that it is U-shaped when viewed from the front; a drive unit 52 mounted on the right side wall 51b to rotate the sample assembly 12 and the sample support carrier 16 in an interlocked manner and to move the sample assembly 12 in the axial direction; a spring device 53 to facilitate the linear, axial movement of the sample assembly 12 by applying a bias force to the sample assembly 12; a cassette mount 54 accommodating the cassette 20 at an angle and adapted to be moved linearly from one of the side walls 51a, 51b to the other; a support table 55 having a direct motion bearing to support the cassette mount 54 linearly movable; and a cassette mount locking member 56 mounted on the left side wall 51a, when viewed from the front, to axially lock the cassette mount 54 when the cassette 20 is installed or removed.

On the inner side of the side wall 51b, a cassette mounting pin 51e protrudes horizontally above a central part of the cassette mount 54. On the outer side of the side wall 51b, a drive unit cover 52a is supported a predetermined distance from the outer surface of the side wall by a plurality of rod members, with the drive unit 52 installed between the side wall 51b and the cover 52a.

The drive unit 52 comprises: an axially movable rotating shaft 52b with its front end adapted to engage the head 13 of the sample assembly 12 installed in the cassette 20; a guide shaft 52c to prevent a rotation of the rotating shaft 52b as the rotating shaft 52b, after having completed its axial movement, returns to its home position and to pull the rotating shaft 52b in the return direction against a spring force; a connecting member 52d to connect the rotating shaft 52b and the guide shaft 52c at their ends protruding outside the cover 52a; a pull knob 52e provided on the outer surface of the connecting member 52d to pull the rotating shaft 52b and the guide shaft 52c simultaneously to their original positions; a shaft side gear member 52f adapted to give a rotating force to the rotating shaft 52b and to function as a bearing to support the axial movement of the rotating shaft 52b; a drive side gear member 52g having a one-way clutch to manually transmit a rotating force to the rotating shaft 52b; and an intermediate gear member 52h to interlockingly connect the shaft side gear member 52f and the drive side gear member 52g.

The rotating shaft 52b has formed in its circumferential surface two grooves 52i, which are parallel to the center axis and arranged at circumferentially equidistant positions. A pin (not shown) to transform the rotating force of the shaft side gear member 52f into a linear thrusting force for the rotating shaft 52b projects from the inner circumferential surface of the shaft side gear member 52f toward the center. The pin is so formed in length and diameter that its front end can be inserted axially movable into the grooves 52i.

A manually operated handle 57 is fitted over an end of the drive side gear member 52g which outwardly protrudes from the cover 52a. Turning the handle 57 with fingers to rotate the drive side gear member 52g transmits the rotating force from the drive side gear member 52g through the intermediate gear member 52h to the shaft side gear member 52f, from which the drive force is further transmitted to the rotating shaft 52b.

Instead of the handle 57, a motor (not shown) may be directly connected to the drive side gear member 52g to construct the rotary drive unit 52.

The cassette mount 54 has erected on its upper surface at the edge of a central part of the left side portion thereof a protruding support shaft member 54a whose front end is inserted into the hole 21j of the side support member 21e. On its upper surface the cassette mount 54 also has a positioning member 54b at a lower end corner on the left side to block the cassette 20 from falling.

Further, at a lower end corner on the right side of the cassette mount 54, a positioning member 54c is erected to prevent the cassette 20 from sliding down.

The cassette mount locking member 56 is oscillatable about a rotating shaft (not shown) supported on the side wall 51a. The cassette mount locking member 56 has a grip portion on the outer side of the side wall 51a and, on the inner side, a locking portion projecting toward the cassette mount 54 to engage an end portion of the cassette mount 54. When the cassette mount 54 approaches the side wall 51a, the grip portion is operated to engage the locking portion with a locking projection (not shown) of the cassette mount 54 to securely lock the cassette mount 54 at the position close to the side wall 51a.

On the back side of the cassette mount 54 there are installed a spring device 53, a damper unit 58 and a latch mechanism 59.

The spring device 53 comprises a bracket 53a erected on the back side of the cassette mount 54, a bobbin 53b rotatably mounted on the bracket 53a, and a coiled spring 53c wound on the bobbin 53b with its free end secured to the front end of the guide shaft 52c.

The damper unit 58 comprises a damper bracket 58a and a damper device 58c having a damper gear (not shown) in mesh with a gear (not shown) on the guide shaft 52c. The damper device 58c uses an oil resistance type rotary damper to prevent a sharp movement.

The latch mechanism 59 comprises an engagement member 59a extending vertically downward from the front end of the guide shaft 52c, a lock member 59b mounted to the damper bracket 58a so that it is oscillatable about the axis, and an unlocking member 59c secured at its upper end to the cassette mount 54 so that it is linearly movable, and also adapted to push a non-engaging end of the lock member 59b to the unlocking side.

The front end portion of the guide shaft 52c is securely attached with the coiled spring 53c. When, with the lower end of the engagement member 59a engaged with the engaging end of the lock member 59b, the cassette mount 54 is moved toward the side wall 51b, causing the unlocking member 59c to push the non-engaging end of the lock member 59b to the unlocking side, the engagement member 59a is disengaged from the lock member 59b. As a result, the guide shaft 52c is moved by the bias force of the coiled spring 53c toward the side wall 51a against a resisting force of the damper device 58c.

To engage the front end of the rotating shaft 52b with the head 13 of the sample assembly 12, the pull knob 52e is pulled outwardly of the cover 52a to allow the cassette 20 to be installed in the sample integration device 50. At this time, the latch mechanism 59 is activated to prevent the rotating shaft 52b from returning to its original position. And after installation of the cassette, the latch mechanism 59 is disengaged to allow the rotating shaft 52b to be moved inwardly of the side wall 51b by the bias force of the coiled spring 53c. The damper device 58c gives an appropriate resisting force to the guide shaft 52c to control its speed, preventing it from moving sharply.

Figure 18:
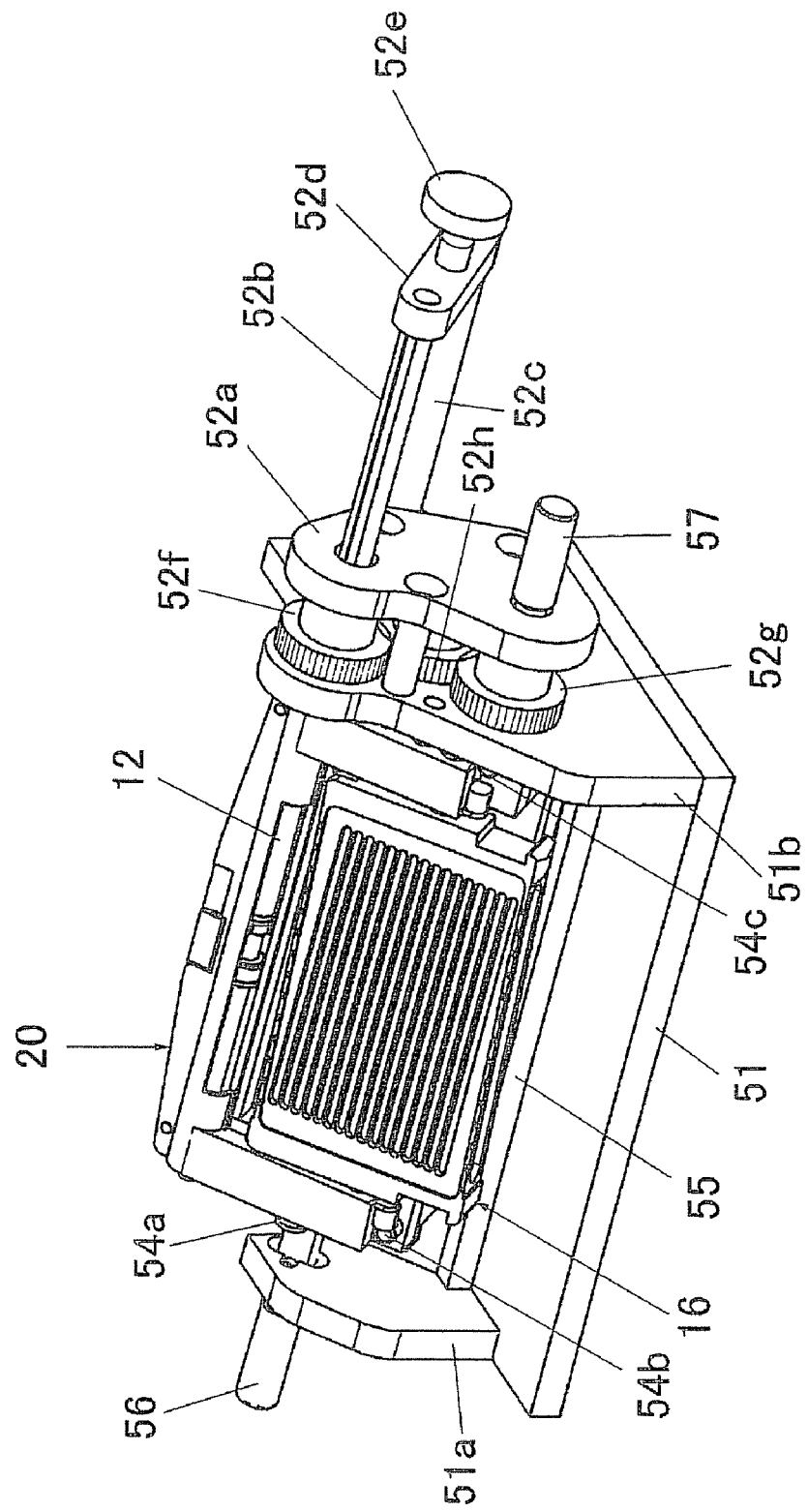
FIG. 18 is a front side perspective view showing the sample integration cassette mounted on the sample integration device.
Figure 19:
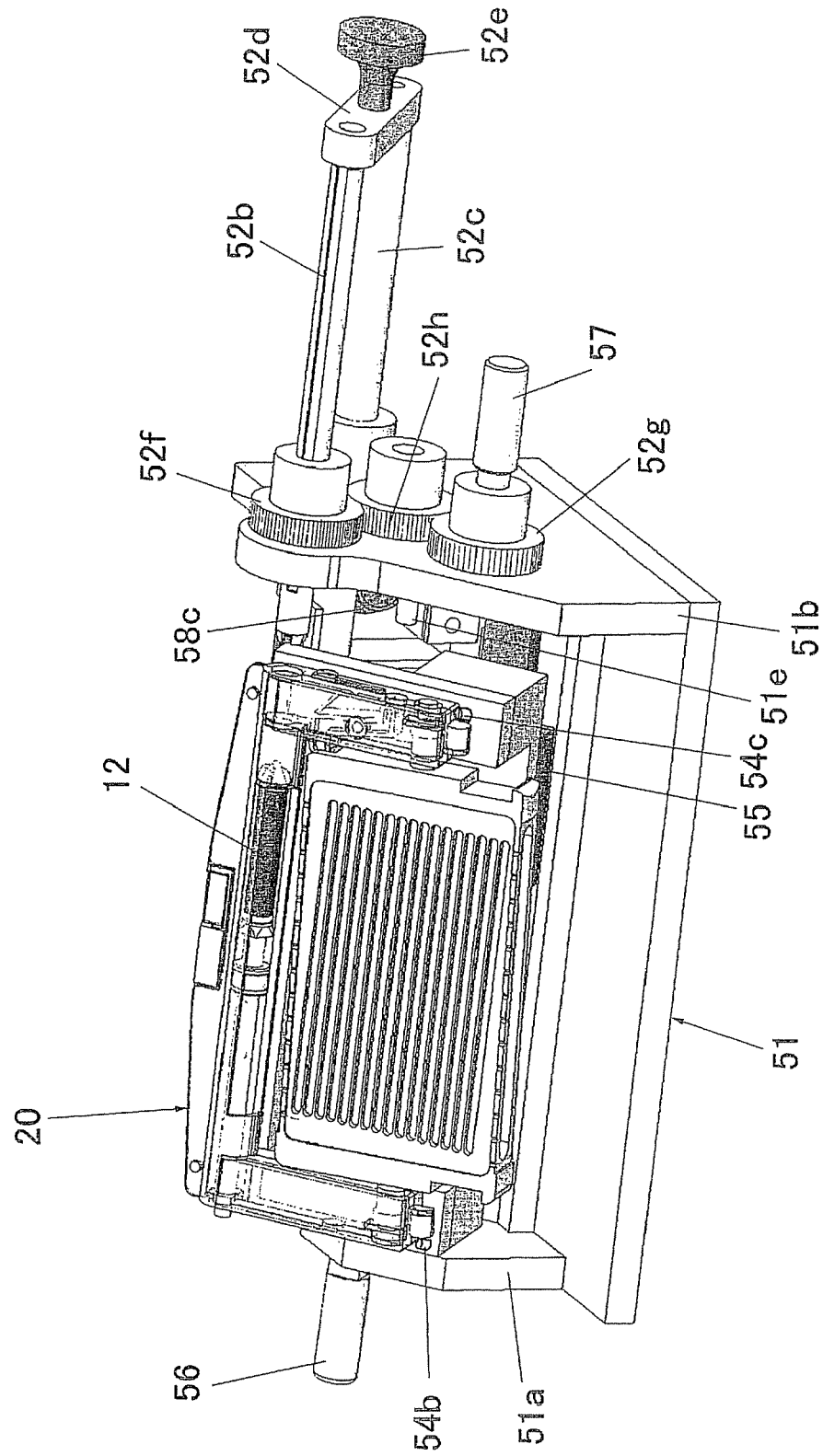
FIG. 19 is a perspective view showing the cassette mounted on the sample integration device with a cover removed.

This sample integration device 50 is used as follows. The cassette 20 is placed on the cassette mount 54; the front end of the support shaft member 54a is inserted into the hole 21j of the cassette 20 to support the cassette, which is also kept from sliding down by the positioning member 54b (FIG. 19); the grip portion of the cassette mount locking member 56 is operated to disengage the locking portion from the locking projection of the cassette mount 54 so that the cassette mount 54 can be moved toward the side wall 51b; and the cassette mount 54 is then moved toward the right side wall 51b until the pin 51e is inserted into the hole 21j (FIG. 18). As a result, the latch mechanism 59 is disengaged and at the same time the pin 51e pushes the engagement end 25e of the stopper 25 of the cassette jig 21, moving the engagement end 25c which is engaged with the sample support carrier 16 toward the unlocking side, disengaging the sample support carrier 16 from the stopper 25. Now, the sample support carrier 16 is freely rotatable about the shaft members 16c, 16c relative to the cassette jig 21.

Then, the rotating shaft 52b is moved toward the sample assembly 12 to engage its front end with the head 13 so that its rotating force can be transmitted to the sample assembly 12.

After the sample support carrier 16 is set free, when the handle 57 connected to the drive side gear member 52g is turned, the drive side gear member 52g is rotated, causing the intermediate gear member 52h and the shaft side gear member 52f to rotate. With the gears rotated in this manner, the head 13 engaged with the front end of the rotating shaft 52b rotates with the sample assembly 12, winding up the sample support 10a from the sample support carrier 16. Since the latch mechanism 59 is disengaged, the rotating shaft 52b and the guide shaft 52c are gradually moved toward the side wall 51a by the bias force of the coiled spring 53c, winding up the sample support 10a along the groove 12e formed on the sample assembly 12.

After the sample support 10a has been wound on the sample assembly 12, the sample assembly 12 attached with the shaft member 14 is taken out of the cassette 20. An ultraviolet light radiation device is used to irradiate the sample support 10a with ultraviolet light to fix the applied samples on the sample support 10a.

Commonly used ultraviolet radiation devices apply ultraviolet light in one direction only, from right to left or from top to bottom. So, an ultraviolet light radiation device is called for which can radiate ultraviolet rays uniformly over the entire circumference of the sample assembly 12.

In the following, a device to radiate ultraviolet light over the entire circumference of the sample assembly 12 will be explained.

Figure 20:
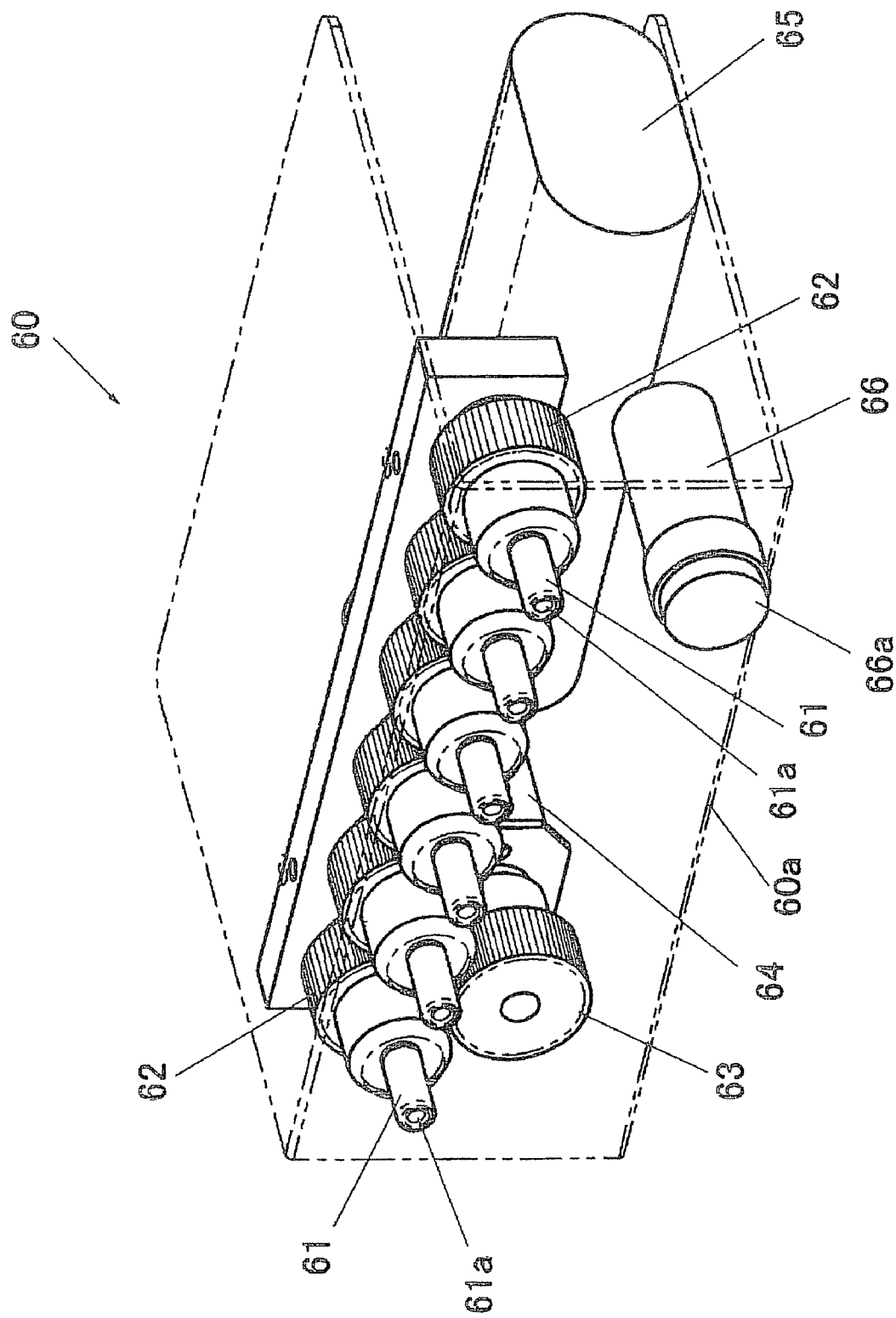
FIG. 20 is a perspective explanatory view showing an outline of a sample assembly rotating device according to the first embodiment of this invention as seen from the right side.
Figure 21:
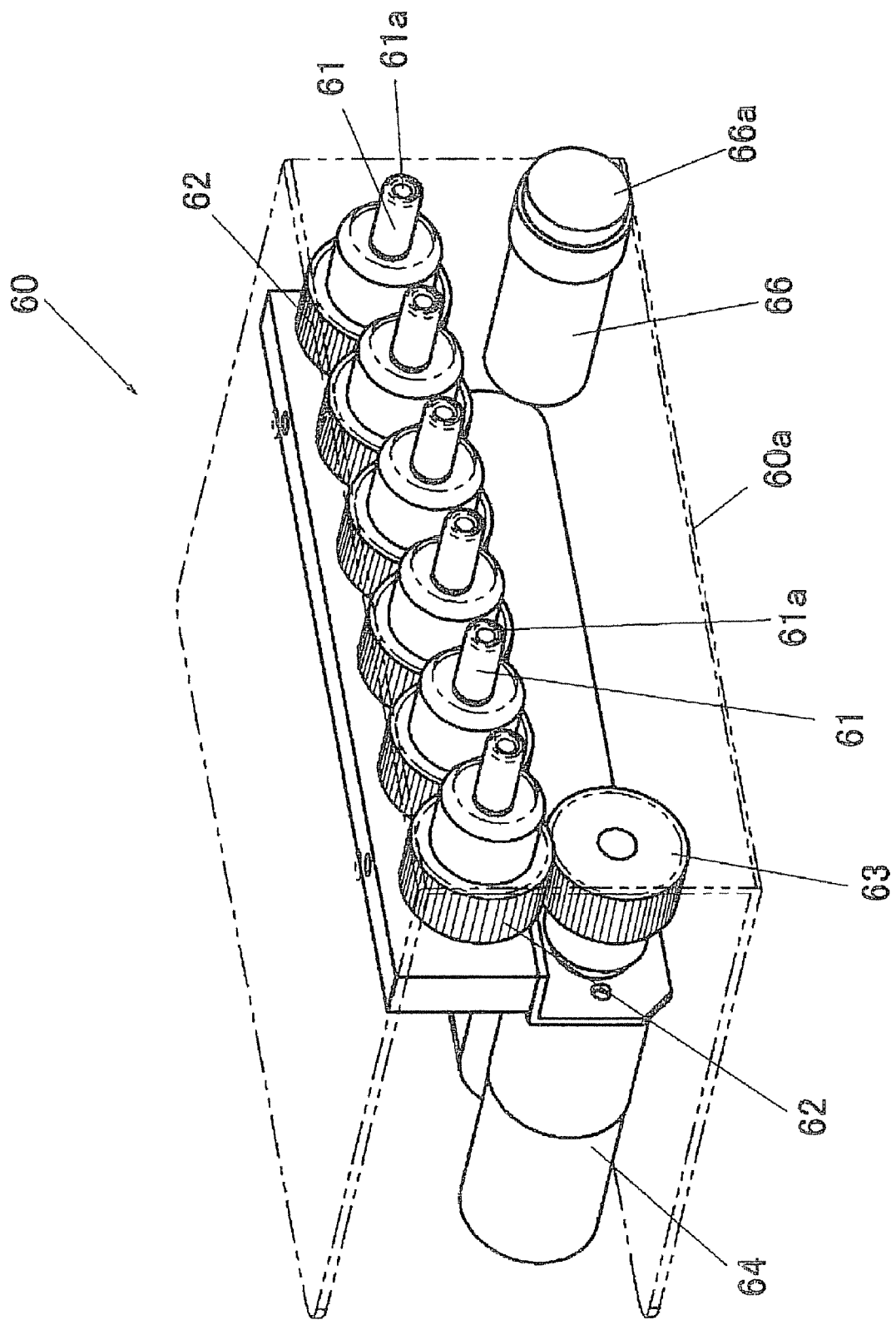
FIG. 21 is a perspective explanatory view showing an outline of the sample assembly rotating device as seen from the left side.
Figure 22:
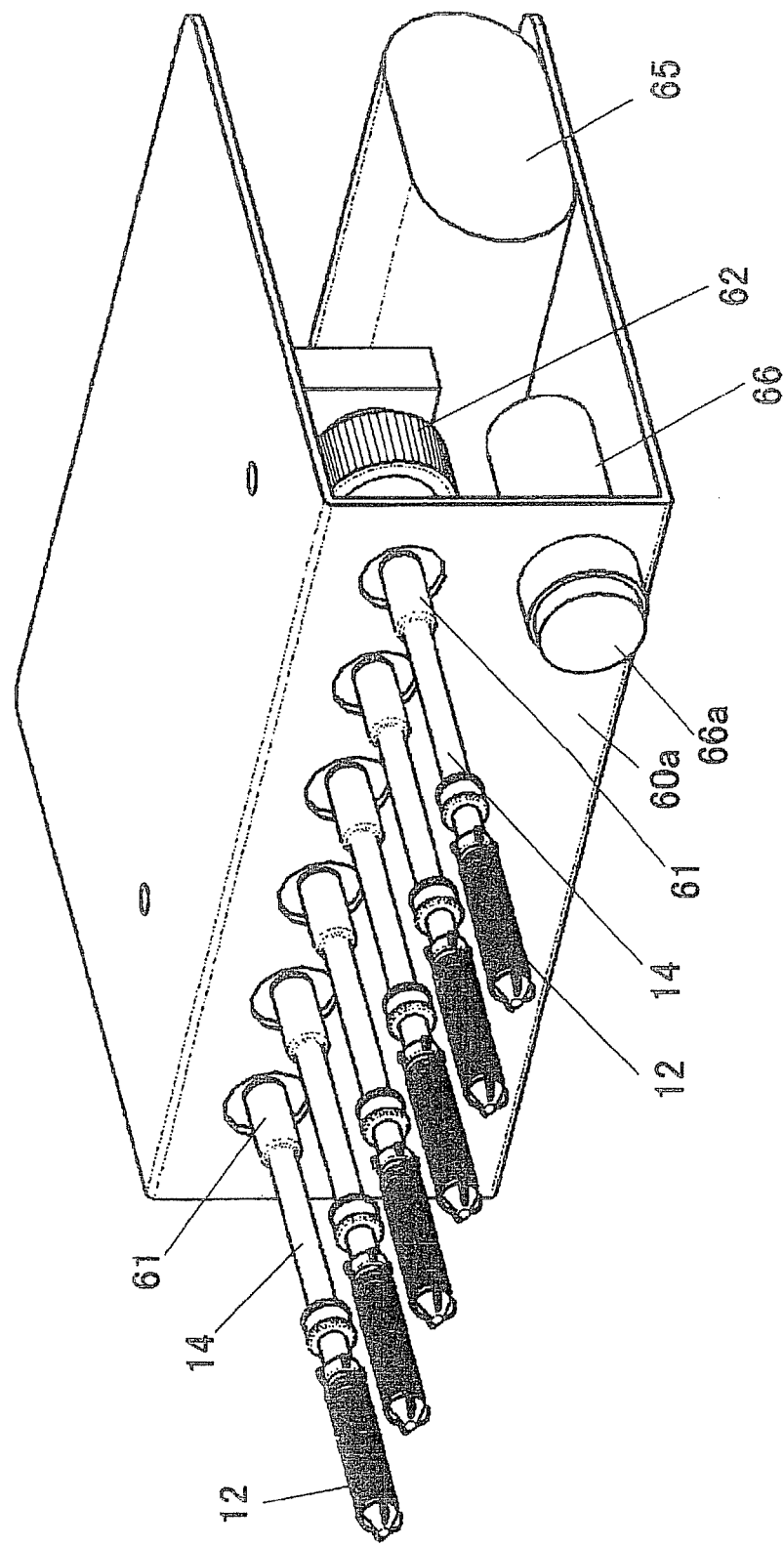
FIG. 22 is a perspective view showing the sample assembly rotating device to which the sample assemblies attached with the shaft members are mounted.
Figure 23:
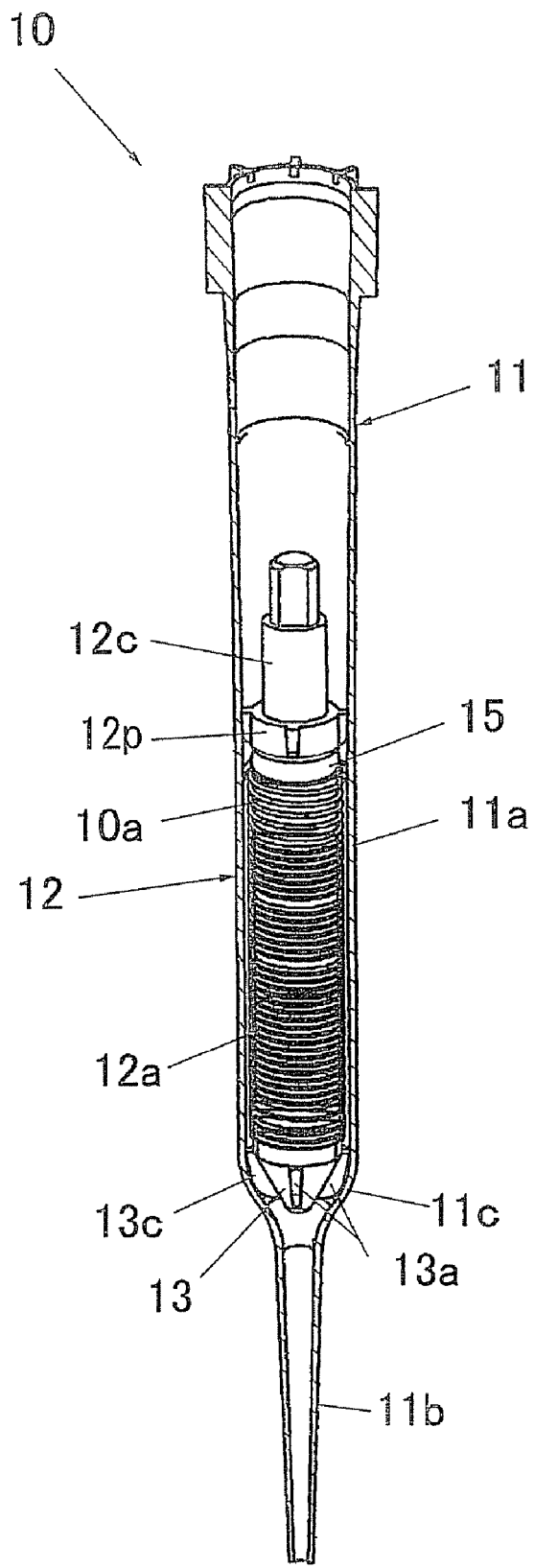
FIG. 23 is a partly cutaway perspective view showing a sample assembly with a spirally wound sample support accommodated in a pipette according to a second embodiment of this invention.
Figure 24:
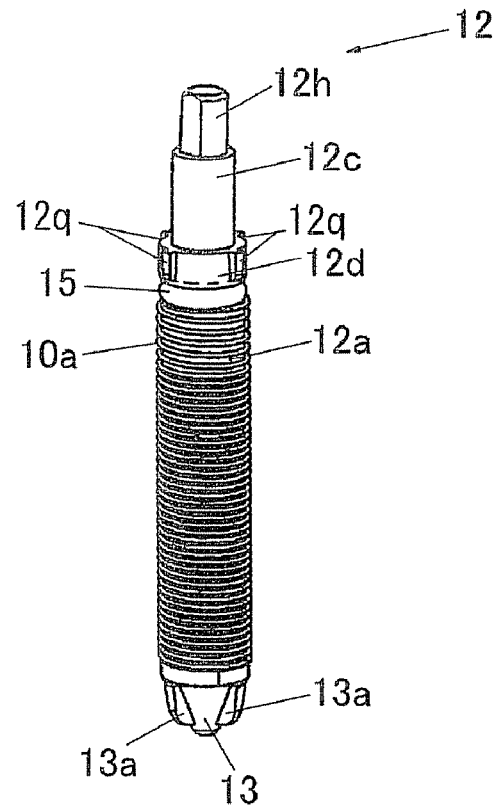
FIG. 24 is a perspective view showing the sample assembly having the sample support spirally wound on it.
Figure 25:
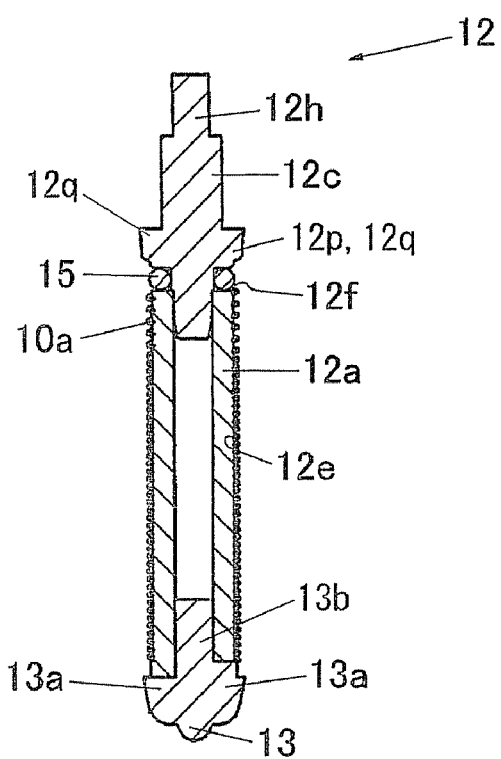
FIG. 25 is a vertical cross-sectional view showing the sample assembly having the sample support spirally wound on it.

A sample assembly rotating device 60, as shown in FIG. 20 through FIG. 22, has multiple sample assemblies 12 (six assemblies in the figure) arranged side by side horizontally to provide a multiple assembly rotating capability by which multiple sample assemblies 12 can be rotated about their axes simultaneously.

On the front side of the device, rotating shafts 61, . . . , 61 having a connecting hole 61a, to which a free end of the shaft member 14 is fitted, are exposed from the front of a case 60a. These rotating shafts 61, . . . , 61 are mounted coaxially with gears 62, . . . , 62 which are in mesh with one another for simultaneous rotation. These are installed inside the case 60a. A drive gear 63 directly coupled with a motor is in mesh with one gear 62 to rotate the remaining gears. A plurality of dry batteries 65 are combined as a power supply to supply electricity to the motor 64 directly coupled to the drive gear 63. The device is also provided with a switch 66, the front end of which protrudes, as a pushbutton, from the front of the device. The switch 66, the battery 65 and the motor 64 are connected by a wire not shown. When the switch 66 is depressed to turn on the power, the motor 64 rotates by the electricity supplied from the battery 65, driving the drive gear 63 to rotate the remaining gears 62, . . . , 62.

As shown in FIG. 22, each of the connecting holes 61a, . . . , 61a receives the shaft member 14 connected with the sample assembly 12, and depressing the pushbutton 66a turns on the motor 64 to rotate the rotating shafts 61, . . . , 61.

After the rotation of the rotating shafts is confirmed, the sample assembly rotating device 60 is placed in the ultraviolet light radiation device (not shown). As the rotating shafts 61, . . . , 61 rotate, the sample assemblies 12 also rotate, exposing the entire circumferences of these assemblies uniformly to ultraviolet light. That is, the use of the sample assembly rotating device 60 enables the entire circumference of each sample assembly 12 to be irradiated with ultraviolet light in the ultraviolet light radiation device, efficiently fixing the applied samples on the sample support 10a.

After the applied samples have been fixed on the sample support 10a by the radiation of ultraviolet light, the sample assemblies 12 are separated from the shaft members 14. Then, as shown in FIG. 1, the sample assembly 12 is accommodated into the pipette 11 by using a sample assembly installation jig not shown.

[Manufacture and Use of Sample Assembly]

If in the first embodiment the sample support 10a, shaft member 14, sample support carrier 16, delivery member 17, cassette 20, spotting device 40, sample integration device 50, sample assembly rotating device 60, etc. are used, the sample assembly 12 is manufactured and used as follows.

The sample assembly 12 and the sample support carrier 16 are set in the cassette jig 21 of the sample assembly cassette 20. That is, with the upper cover 21a of the cassette jig 21 removed, the sample assembly 12 attached with the shaft member 14 and which has yet to be wound with the sample support 10a and the sample support carrier 16 not yet wound with the sample support 10a are assembled. In this state, the sample support 10a fed from a bobbin is wound around the sample support carrier 16.

The winding process is as follows. The front end of the sample support 10a is secured to the slit 16j. Then, the sample support carrier 16 is turned to lead the sample support 10a to a side surface opposite the one where the slit 16j is formed and to pass the sample support through the nearest V groove 16e. The sample support 10a is further led to the opposite side and passed through the corresponding V groove 16e. The sample support carrier 16 is again turned to wind the sample support 10a around the opposite side surface, pass it through the next V groove 16e, then lead it to the opposite side surface and pass it through the corresponding V groove 16e. This process is repeated until the sample support 10a is wound and passed through all V grooves 16e formed in the longer sides of the sample support carrier. Then, the stopper 25 is engaged in the groove 16g to prevent the sample support carrier 16 from being turned. After this, a portion of the sample support 10a near the position where it is to be cut is pushed down between the core 12a of the sample assembly 12 and the head 13. The head 13 is pushed against the front end of the core 12a to strongly clamp the sample support 10a. Then the sample support 10a is cut at a position close to the clamped position between the head 13 and the core 12a to prevent an excess part of the sample support 10a from protruding from the clamped position. Then, the upper cover 21a is attached to the lower cover 21b and now the sample assembly cassette 20 is complete.

The cassette 20 wound with the sample support 10a is placed on the cassette mount 41a of the stand 42 of the spotting device. The delivery member 17, which holds in the front ends of the protruding members 17b, . . . , 17b the sample suspending liquids that were drawn in from ¼ the wells arrayed in the microplatelike vessel, is fitted in the holder portion 43c of the delivery member mounting table 43b. The movable table 43 is lowered until it abuts against the stopper 41c, to apply the sample suspending liquids in a predetermined row and column matrix to the sample support 10a wound on the sample support carrier 16 set in the cassette. Then, the downward force is released from the movable table 43 to allow it to move up by the bias force of the coiled spring 44a. After the movable table 43 has moved up, the delivery member 17 is taken out. The delivery member 17 then draws in new sample suspending liquids from ¼ the wells arrayed in the microplatelike vessel and is reversed between the left and right sides before being fitted again. The movable table 43 is then lowered until it abuts against the stopper 41c, to additionally apply to the sample support 10a, which is already attached with the previously applied sample suspending liquids in a row and column matrix ¼ that of the arrayed wells, the new sample suspending liquids in a matrix ¼ that of the arrayed wells at intermediate positions between the previously applied sample suspending liquids.

After this, the movable table 43 is moved up; the delivery member 17 is taken out; the sample support carrier 16 incorporated in the cassette 20 is turned upside down and set again in the cassette mount 41a; the delivery member 17 that has drawn in new sample suspending liquids from another ¼ of the arrayed wells in the microplatelike vessel is fitted; the movable table 43 is lowered until it abuts against the stopper 41c to apply the sample suspending liquids in a predetermined row and column matrix; then the downward force is released from the movable table 43; after the movable table 43 has been moved up by the bias force of the coiled spring 44a, the delivery member 17 is taken out; the delivery member 17 that has drawn in new sample suspending liquids from the last ¼ of the arrayed wells in the microplatelike vessel is reversed between left and right side before being fitted again; the movable table 43 is again lowered until it abuts against the stopper 41c, to additionally apply to the sample support 10a, which is already attached with the previously applied sample suspending liquids in a row and column matrix ¼ that of the arrayed wells, the new sample suspending liquids in a matrix ¼ that of the arrayed wells at intermediate positions between the previously applied sample suspending liquids. This process allows the sample suspending liquids to be applied to the sample support 10a at high density.

After the sample suspending liquids have been applied to the sample support 10a, they are left to dry naturally (for a few minutes). The cassette 20 is placed on the cassette mount 54 standing by on the left side of the sample integration device 50 when viewed from the front. The front end of the support shaft member 54a is inserted into the hole 21j of the cassette 20 to support it. At the same time, the cassette 20 is kept from sliding down by the positioning member 54b. The grip portion of the cassette mount locking member 56 is operated to disengage the locking portion from the locking projection of the cassette mount 54 so that the cassette mount 54 can be moved toward the side wall 51b. Then the cassette mount 54 is moved toward the right side wall 51b until the pin 51e is inserted into the hole 21j. At this time, the latch mechanism 59 is disengaged and the pin 51e pushes the engagement end 25e of the stopper 25 of the cassette jig 21, moving the engagement end 25c, which is engaged with the sample support carrier 16, toward the unlocking side to disengage the sample support carrier 16 from the stopper 25. As a result, the sample support carrier 16 is set free to rotate about the shaft members 16c, 16c relative to the cassette jig 21.

Then, the rotating shaft 52b is moved toward the sample assembly 12 to engage its front end with the head 13 so that its rotating force can be transmitted to the sample assembly 12.

After the sample support carrier 16 is set free, when the handle 57 connected to the drive side gear member 52g is turned, the drive side gear member 52g is rotated, driving the intermediate gear member 52h and the shaft side gear member 52f. With the gears rotated in this manner, the head 13 engaged with the front end of the rotating shaft 52b rotates with the sample assembly 12, winding up the sample support 10a from the sample support carrier 16. At the same time, the rotating shaft 52b and the guide shaft 52c are gradually moved toward the side wall 51a by the bias force of the coiled spring 53c, winding up the sample support 10a along the groove 12e formed on the sample assembly 12.

After the sample support 10a has been wound on the sample assembly 12, the sample assembly 12 attached with the shaft member 14 is taken out of the cassette 20. The sample assemblies 12, . . . , 12 each wound with the sample support 10a are then mounted to the sample assembly rotating device 60 by fitting the shaft members 14, . . . , 14 into the connecting holes 61a, . . . , 61a of the rotating shafts 61, . . . , 61.

After the shaft members 14, . . . , 14 of the sample assemblies 12, . . . , 12, each wound with the sample support 10a, are fitted into the connecting holes 61a, . . . , 61a of the rotating shafts 61, . . . , 61 of the sample assembly rotating device 60, the pushbutton 66a is pressed to start the motor 64, rotating the rotating shafts 61, . . . , 61. After the rotation of the shafts is confirmed, the sample assembly rotating device 60 is placed in the ultraviolet light radiation device. As the rotating shafts 61, . . . , 61 rotate, the sample assemblies 12 also rotate, exposing the entire circumferences of these assemblies uniformly to ultraviolet light. After the samples adhering to the sample support 10a have been fixed by the radiation of ultraviolet light, the sample assemblies 12 are separated from the shaft members 14. Then, each sample assembly is accommodated into the pipette 11 by using a sample assembly installation jig. Now the assembled product can be used as a probe 10.

In the accommodation-reaction-measurement process using this probe 10, the lower end of the probe 10 is inserted into a container accommodating a liquid suspending a labeled biological substance containing a fluorescent material. The labeled biological substance suspending liquid is drawn into the probe until the liquid soaks an entire core 12a of the sample assembly 12 so as to bring a binding material in the labeled biological substance into contact with the sample support 10a, thereby bonding the detection biological substance adhering to the sample support to a binding material in the labeled biological substance.

After this, the labeled biological substance suspending liquid drawn in from the lower end of the probe 10 is discharged. Then a cleansing liquid is drawn into and discharged from the pipette to clean its interior and wash out a residue of the labeled biological substance suspending liquid.

After cleaning, a measuring liquid is drawn into the pipette 11 which is then set in an accommodation-reaction-measurement device (not shown). A red semiconductor laser beam is radiated from outside the probe 10 toward the sample assembly 12 to cause a fluorescent material to illuminate at a position where the detection biological substance binds with the binding material in the labeled biological substance. The light produced is received by a light receiving portion to measure the illuminating positions on the entire core. From the detected illuminating positions, the binding material in the labeled biological substance is determined. Based on a combination of all the detected binding materials, a target substance is determined.

With the above series of steps of manufacturing the probe 10 that accommodates the sample assembly 12 in the pipette 11, it is possible to fabricate small-size sample assemblies 12 with high precision and efficiency by using the cassette 20, spotting device 40, sample integration device 50 and sample assembly rotating device 60.

With this process, the sample support 10a can be wound uniformly around the core 12a, increasing the sample integration density, reducing the size of the sample assembly and probe and therefore the size of the measuring device as a whole. This in turn reduces the cost of the accommodation-reaction-measurement process. Further, a reduction in the size of the measuring device leads to a reduced consumption of samples. In addition, the sample assembly 12 can be fabricated with ease and high precision, improving the work efficiency and reducing the number of manufacturing steps, which in turn results in a substantial reduction in the probe manufacturing time. Furthermore, this manufacturing method enables the biological substance accommodation-reaction-measurement process requiring a large number of sample assemblies 12 to be performed in a significantly reduced time, resulting in a substantial reduction in an overall time taken from an inspection request to a reporting of inspection result.

The use of the sample assembly 12 small in size and fabricated with high precision and of the red semiconductor laser beam can not only enhance the detection accuracy with which illuminated positions are detected in the accommodation-reaction-measurement process but also reduce cost, thus realizing a highly precise, inexpensive accommodation-reaction-measurement process.

Second Embodiment

In the following a device with some improvements on the sample assembly and on various devices in the first embodiment will be explained. Those components that are not modified but remain the same as in the first embodiment are given the same reference numbers and their detailed explanations are omitted.

As shown in FIG. 23 to FIG. 26, probe 10 comprises a pipette 11 and a sample assembly 12 having a threadlike sample support 10a spirally wound around its circumferential surface. The sample assembly 12 has its body formed cylindrical, which comprises a core 12a and a handle 12c. The core 12a is engraved in its outer circumferential surface with a groove 12e along which the sample support 10a is wound. The handle 12c has a new centering portion 12p which is fitted at one end into the base end side of the core 12a.

The handle 12c comprises a front end side shaft portion fitted into the core 12a; a front end stepped portion that, together with the rear end of the core 12a, forms an O-ring groove 12f; a centering portion 12p having a plurality of ribs 12q (four in the figure) that engage the inner surface of the large-diameter portion 11a of the pipette 11 for centering and positioning; a circular column portion situated at the central part of the handle; and a connecting portion 12h formed at the rear end of the handle for connection with other shaft member. The handle 12c, as described above, is a shaft member with multiple outer diameters.

Between the rib 12q and the rib 12q of the centering portion 12p is formed a passage through which gas and liquid drawn in can flow easily.

By moving the head 13 to separate the rear end face of the head 13 from the front end face of the core 12a, the front end portion of the sample support 10a can be put in a gap formed. The head 13 is then moved to engage its rear end face with the front end face of the core 12a to strongly clamp the front end portion of the sample support 10a between these faces to facilitate the winding operation of the sample support 10a around the core 12a.

Figure 26:
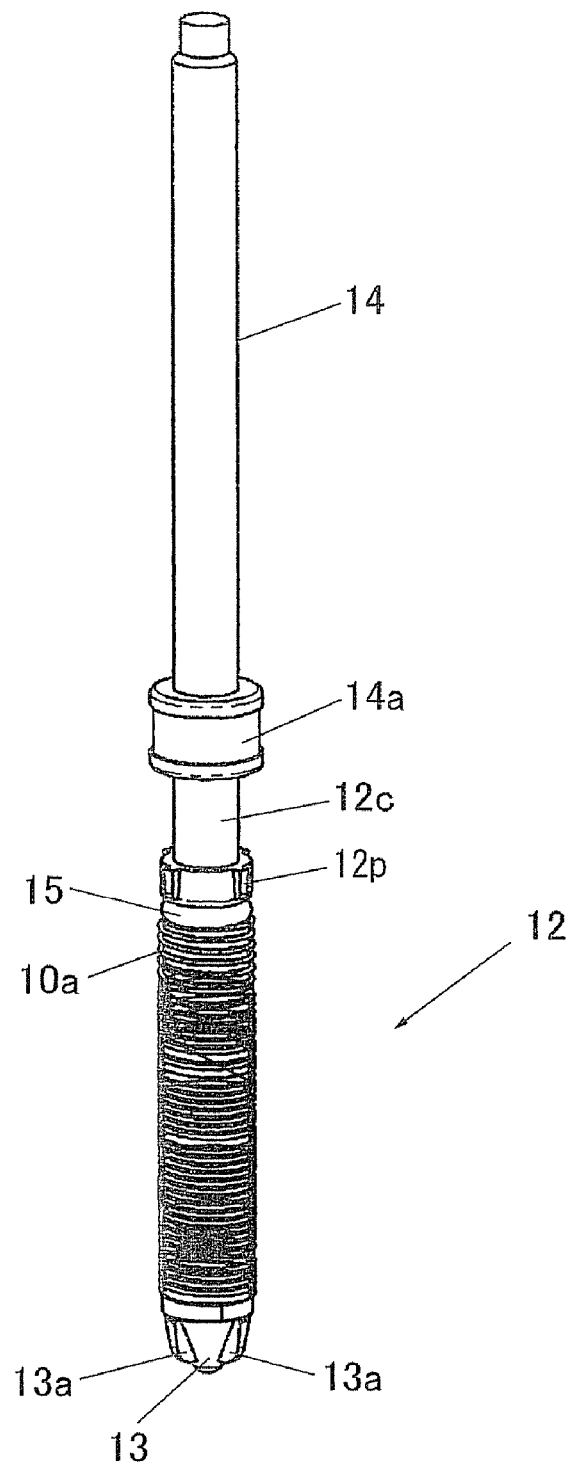
FIG. 26 is a perspective view showing a shaft member fitted to the sample assembly.
Figure 27:
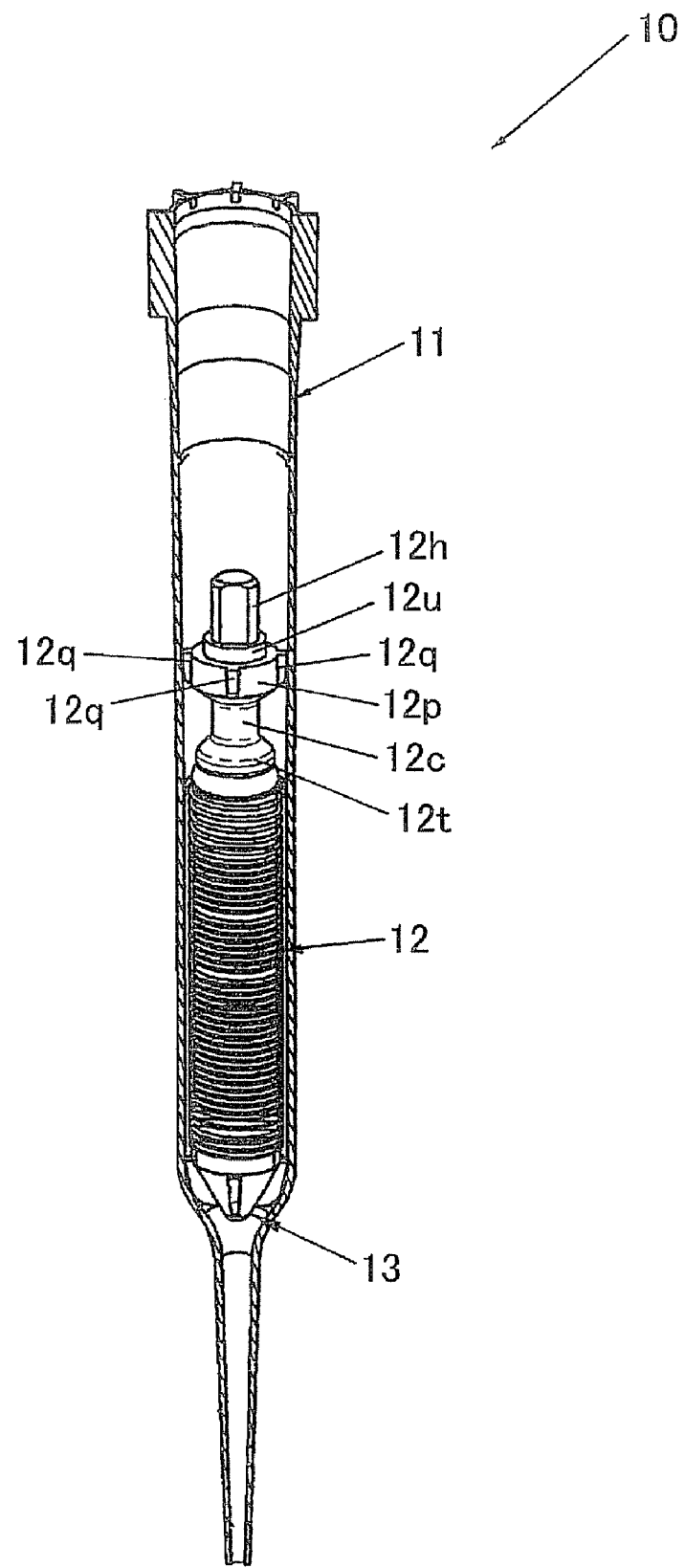
FIG. 27 is a partly cutaway perspective view showing another example of sample assembly with a spirally wound sample support accommodated in a pipette according to the second embodiment of this invention.
Figure 28:
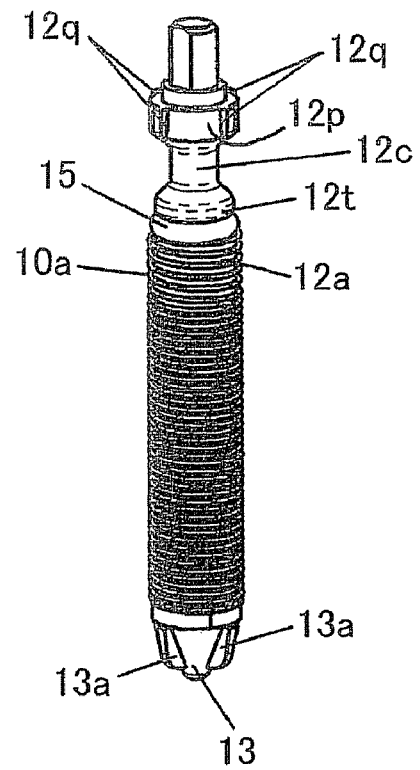
FIG. 28 is a perspective view showing the sample assembly of FIG. 27 wound with the sample support.
Figure 29:
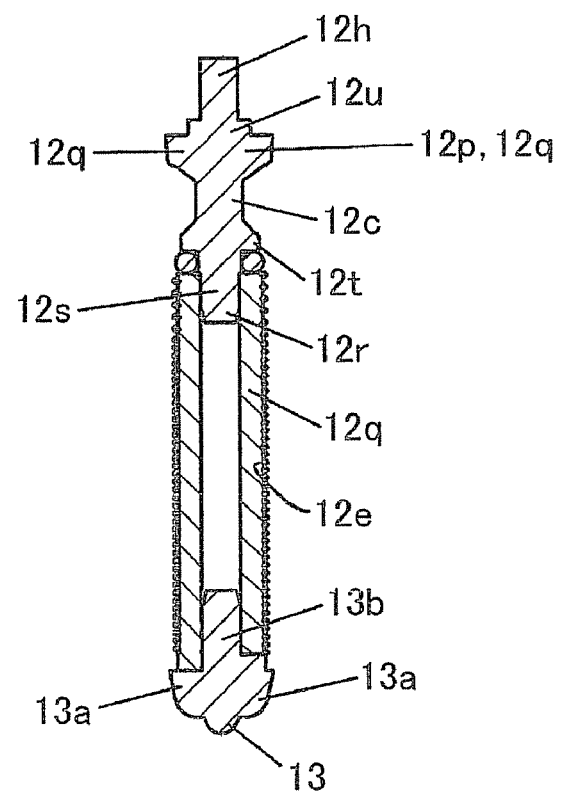
FIG. 29 is a vertical cross-sectional view showing the sample assembly of FIG. 27 wound with the sample support.
Figure 30:
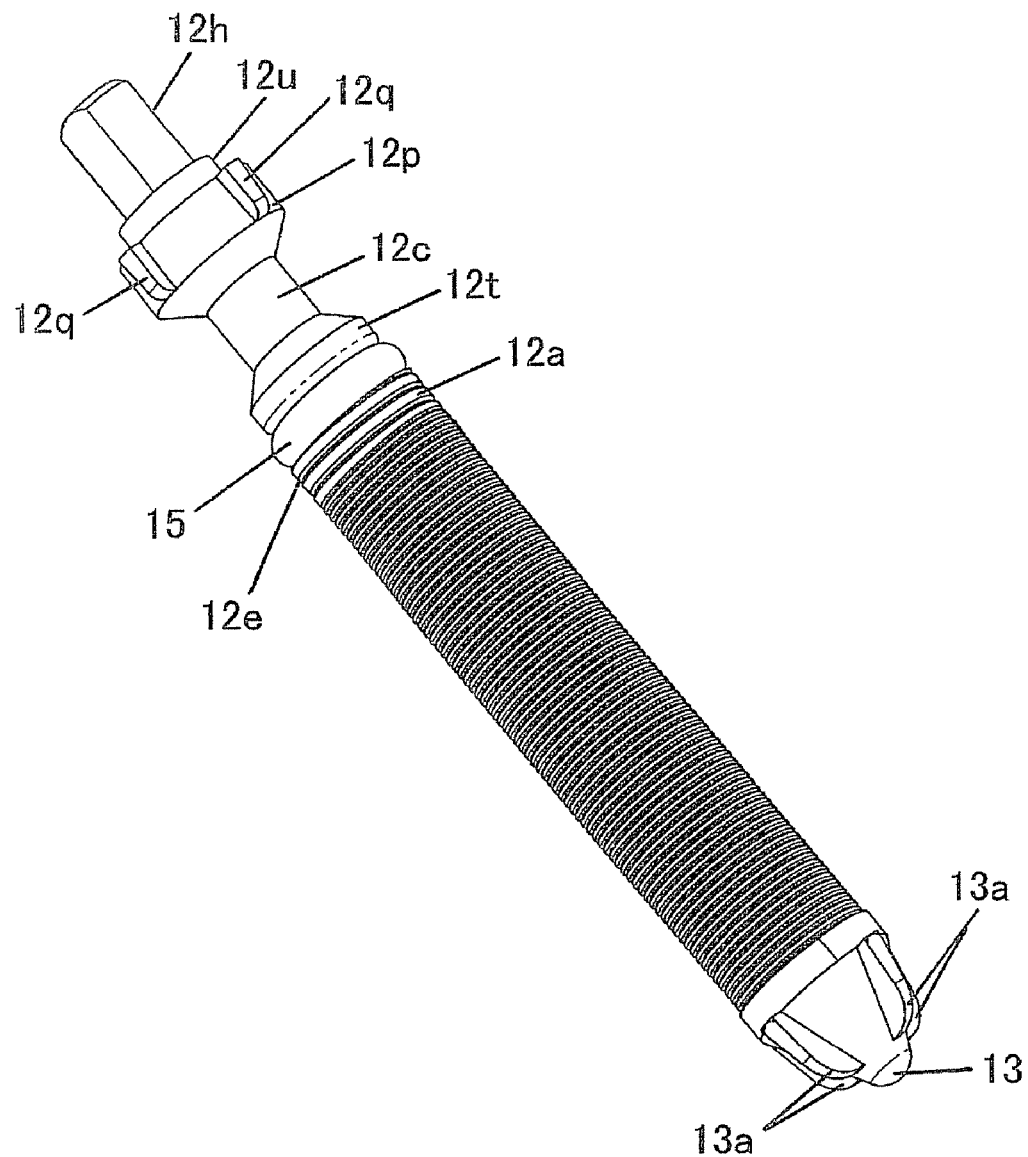
FIG. 30 is an enlarged perspective view of the sample assembly of FIG. 27.
Figure 31:
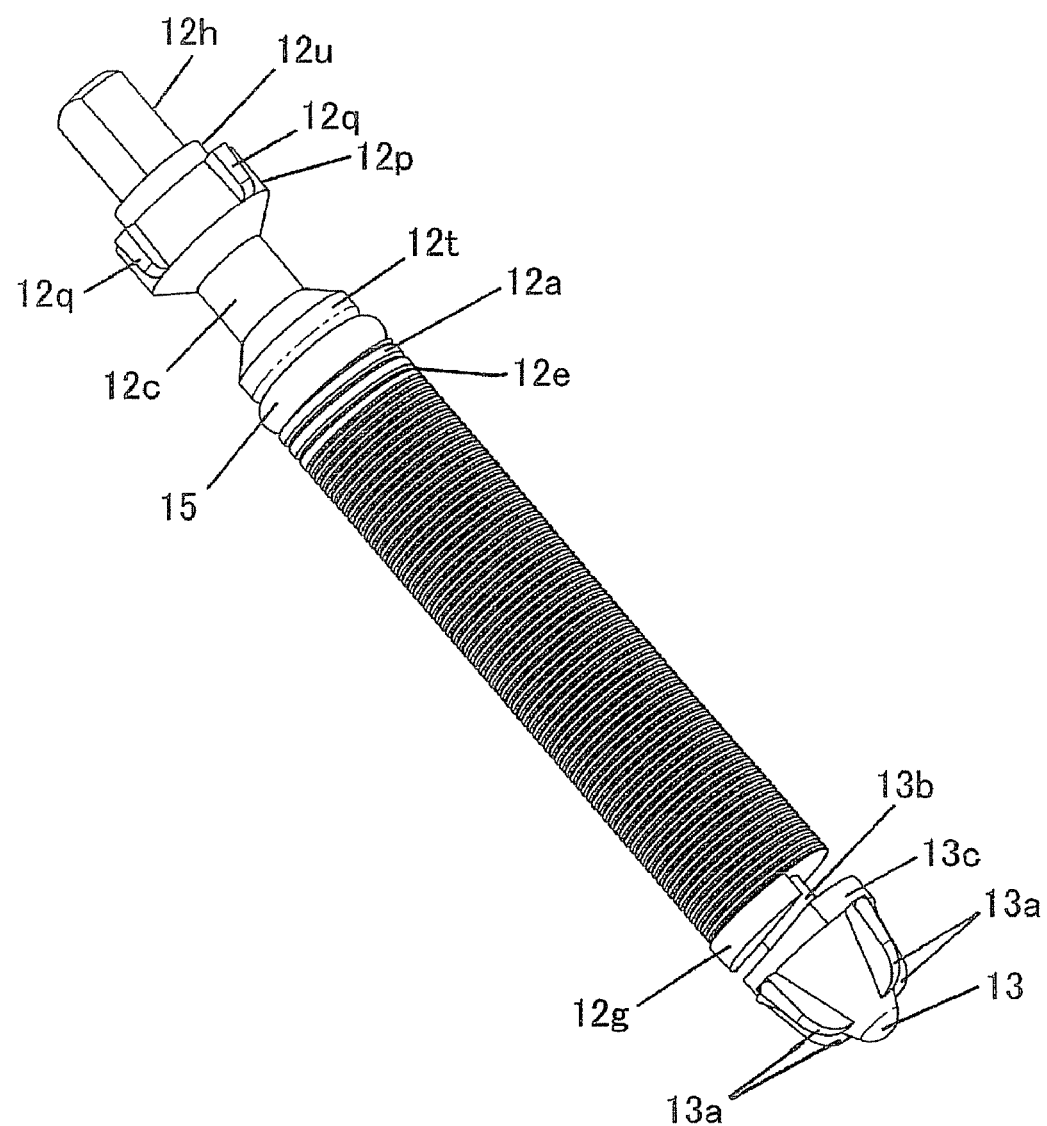
FIG. 31 is an enlarged perspective view showing a core and a head of the sample assembly of FIG. 27 separated from each other.
Figure 32:
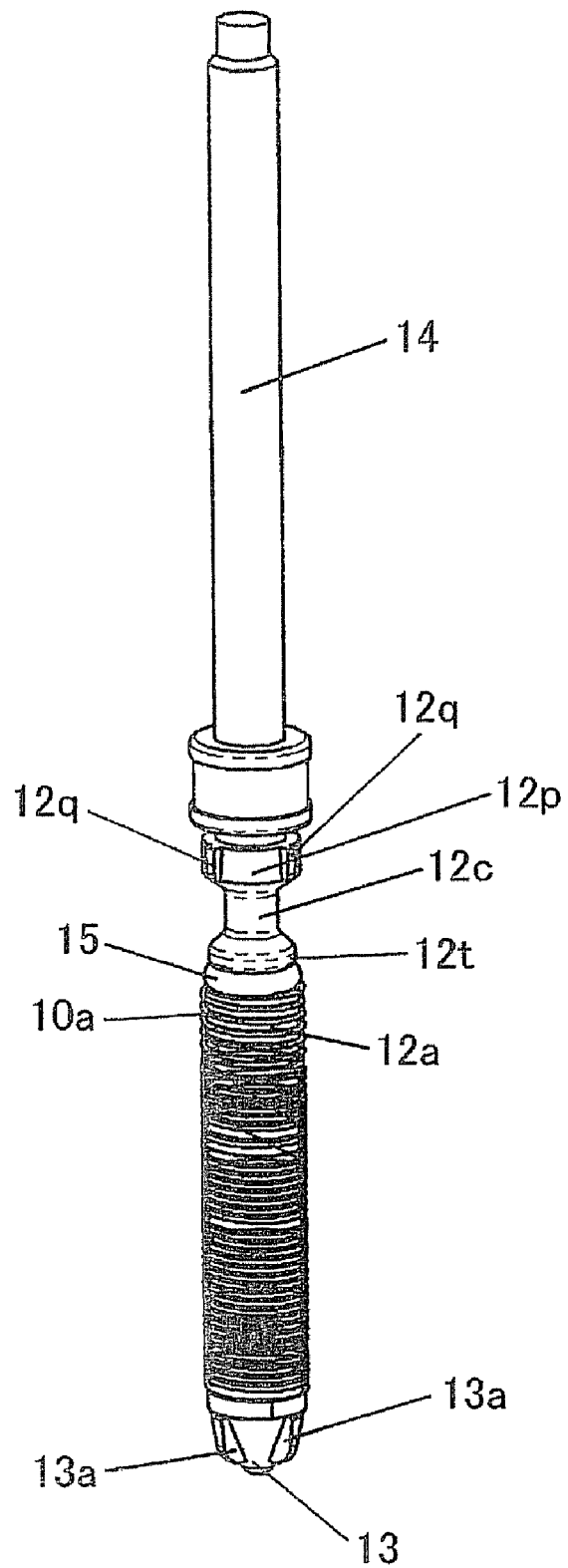
FIG. 32 is a perspective view showing a shaft member fitted to the sample assembly of FIG. 27.

The sample assembly 12 in a state before being put in the pipette 11, as shown in FIG. 26, is not used as is. A shaft member 14 to be mounted on the cassette is coaxially connected to the sample assembly 12 by fitting a hole (not shown)

in the front end of the shaft member 14 over the connecting portion 12h of the handle 12c at the base of the sample assembly 12.

As another construction of the sample assembly 12, it may be formed as shown in FIG. 27 to FIG. 31.

In this construction, the body of the sample assembly 12 is formed cylindrical and comprises a core 12a having a spiral groove 12e engraved in its outer circumferential surface along which the sample support 10a is wound, and handle 12c with its end fitted into the base end side of the core 12a. The handle 12c comprises: a front end side shaft portion 12r fitted into the core 12a; a front end side stepped portion 12s that, together with the rear end of the core 12a, forms an O-ring groove 12f, a flange portion 12t forming an end face of the O-ring groove 12f on the handle side; a centering portion 12p having a plurality of ribs 12q (four in the figure) that engage the inner surface of the large-diameter portion 11a of the pipette 11 for centering and positioning; a circular column handle portion 12c situated between the flange portion 12t and the centering portion 12p and having a smaller outer diameter than that of the flange portion 12t; a stepped portion 12u protruding from the rear end face of the centering portion 12p; and a connecting portion 12h formed at the back of the stepped portion 12u for connection with other shaft member. The handle 12c, as described above, is a shaft member with multiple outer diameters. Between the rib 12q and the rib 12q of the centering portion 12p is formed a passage through which gas and liquid drawn in can flow easily and which separates the engagement portion with the shaft member 14 from the liquid drawn in to prevent possible leakage and facilitate post processing, avoiding unwanted trouble with residual liquid.

Figure 47:
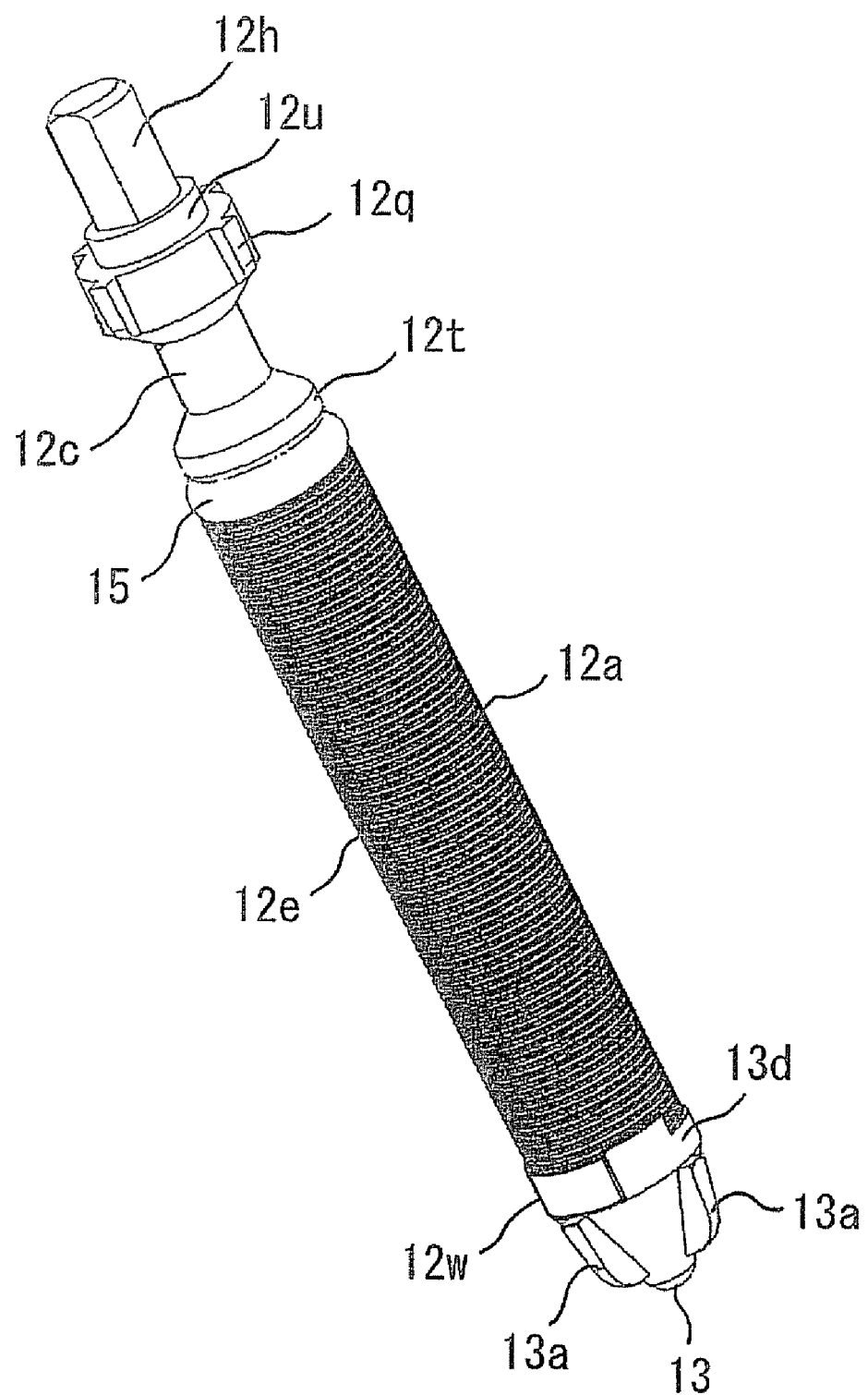
FIG. 47 is a perspective view showing a still another example of the sample assembly according to the second embodiment of this invention.
Figure 48:
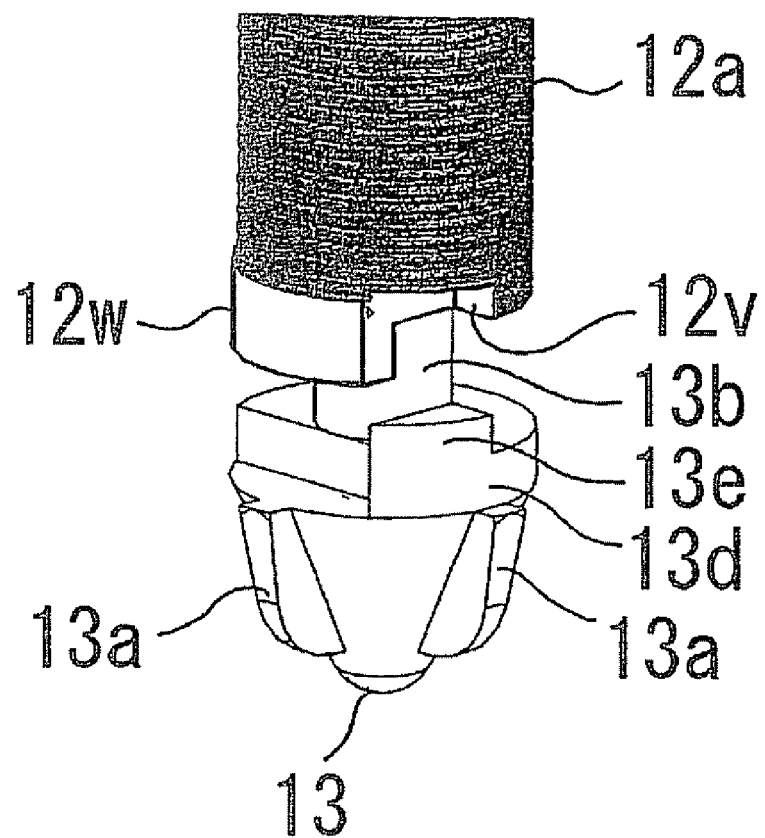
FIG. 48 is an enlarged perspective view showing a core and a head of the sample assembly of FIG. 47 separated from each other.

Still another example of the sample assembly 12 may have a construction of FIG. 47 and FIG. 48. In FIG. 47 and FIG. 48, the same reference numbers as those in the preceding drawings represent identical components and their explanations are omitted.

In this construction, the head 13 adapted to hold the front end of the sample support 10a has a center shaft member 13b that is axially movable and coaxially fits into the core 12a, as in the previous construction. But unlike the previous construction, the core 12a has a protrusion 12w protruding axially forwardly from the front end thereof and having a transverse cross section of almost right triangle with an arc hypotenuse. In a part of the front end of the core 12a adjoining the protrusion 12w is formed a recess 12v extending axially rearward which is enclosed by three surfaces, i.e., a front end face having an almost right triangle shape with an arc hypotenuse and transversely crossing the axial direction and two orthogonal side surfaces perpendicularly crossing the front end face, these three surfaces forming an apex at a right angle point of the triangle of the front end face. One of the two orthogonal side surfaces of the protrusion 12w is a surface commonly used as one side surface enclosing the recess 12v. The two orthogonal side surfaces are almost L-shaped. At the rear end of the head 13 is formed an axially rearwardly extending protrusion 13d which, together with the protrusion 12w, forms a circular pillar. The protrusion 13d is formed with an axially rearwardly extending raised portion 13e having a transverse cross section of almost right triangle with an arc hypotenuse and adapted to fit into the recess 12v.

In this construction, the front end of the groove 12e is connected between the side surface of the recess 12v of the core 12a and the side surface of the raised portion 13e so that the front end of the sample support 10a can easily enter from the clamped position into the groove 12e.

Because the front end of the core 12a and the rear end of the head 13 are formed as described above, when the head 13 is moved toward the core 12a, the protrusions 12w, 13d combine together to form a circular pillar having the same outline as the core 12a. That is, the combination of the core 12a and the two protrusions 12w, 13d and the combination of the recess 12v and the raised portion 13e form circular pillar members of the same diameter with the head 13 attached at the front end.

In this construction, since the sample support 10a begins to be wound from the clamped portion between the raised portion 13e and the recess 12v, when the pipette 11 that accommodates the sample assembly wound with the sample support 10a draws in and discharges liquid, it is possible to prevent a trouble in which, because of a fluid force along the axial direction, the sample support 10a may be dislocated from the groove 12e and caught in a gap of the clamped portion between the front end face of the core 12a and the rear end face of the head 13.

Figure 33:
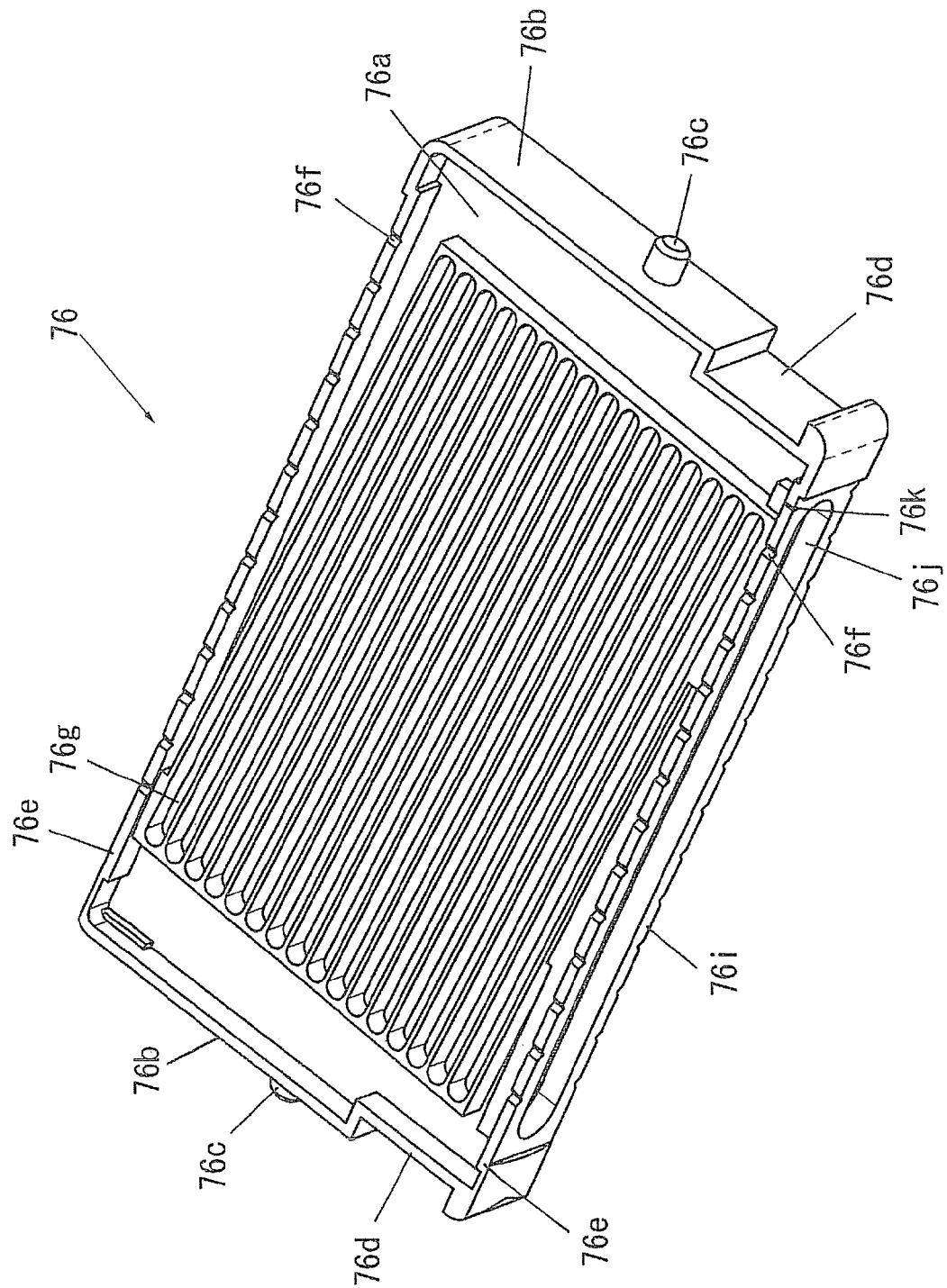
FIG. 33 is a perspective view showing a sample support carrier on which the sample support is wound according to the second embodiment of this invention.

A sample support carrier 76 has platelike outer circumferential walls along a circumference of its thin plate 76a as its central body, as shown in FIG. 33. From a central part of each platelike outer circumferential wall 76b, 76b on each short side, shaft member 76c, 76c is projected. A rectangular recess 76d, 76d is formed in an end portion of each platelike outer circumferential wall 76b, 76b on one side of the shaft member 76c, 76c. Platelike outer circumferential walls 76e, 76e on longer sides have V grooves 76f, . . . , 76f formed in their upper and lower edges at equal intervals and staggered by half-pitch between the two long sides.

Further, in the upper and lower surfaces of the plate 76a, a plurality of narrow slots 76g, . . . , 76g (16 slots in the figure) piercing from each surface into a hollow portion are parallelly formed at an angle to the center line of the shaft members 76c, 76c. The inclination angle of the slots 76g, . . . , 76g is preferably set almost perpendicular to the inclination angle of the groove 12e of the sample assembly 12. Particularly, the inclination angle of the slots 76g, . . . , 76g may be represented by an angle to the platelike outer circumferential walls 76e, 76e on the longer sides that are formed with the V grooves 76f, . . . , 76f. In that case, the inclination angle of the slots 76g, . . . , 76g should be such that the sample support wound on the V grooves 76f, . . . , 76f formed in the longer side platelike outer circumferential walls 76e, 76e crosses the slots 76g, . . . , 76g at right angles.

The size of the sample support carrier 76 is determined by setting the size of the plate 76a, the positions of the slots 76g, . . . , 76g and the positions of the V grooves 76f, . . . , 76f according to the positions of the arrayed protruding members 17b, 17b of the delivery member 17 and to the size of the array.

Figure 34:
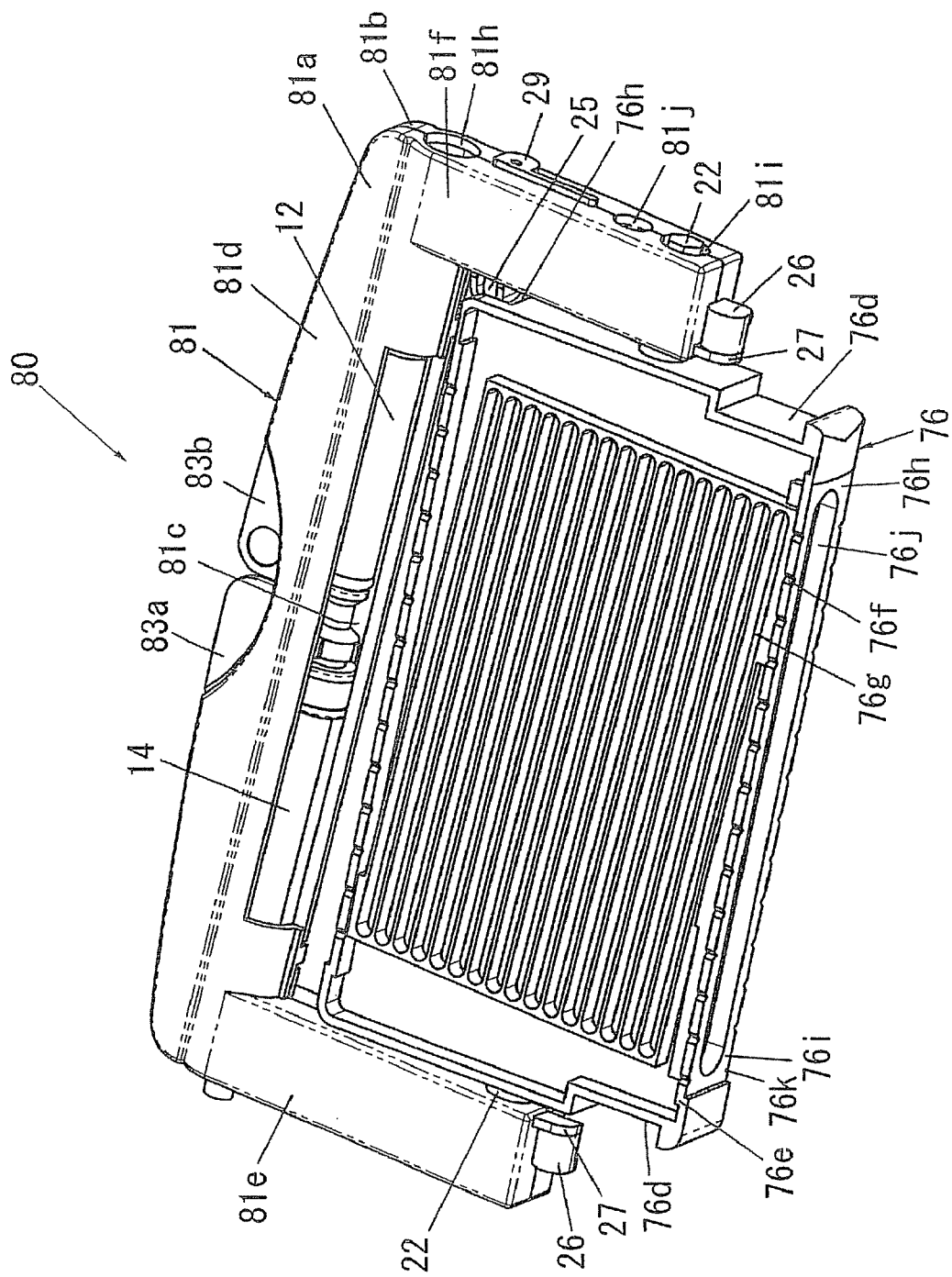
FIG. 34 is a perspective view showing a sample integration cassette according to the second embodiment of this invention.
Figure 35:
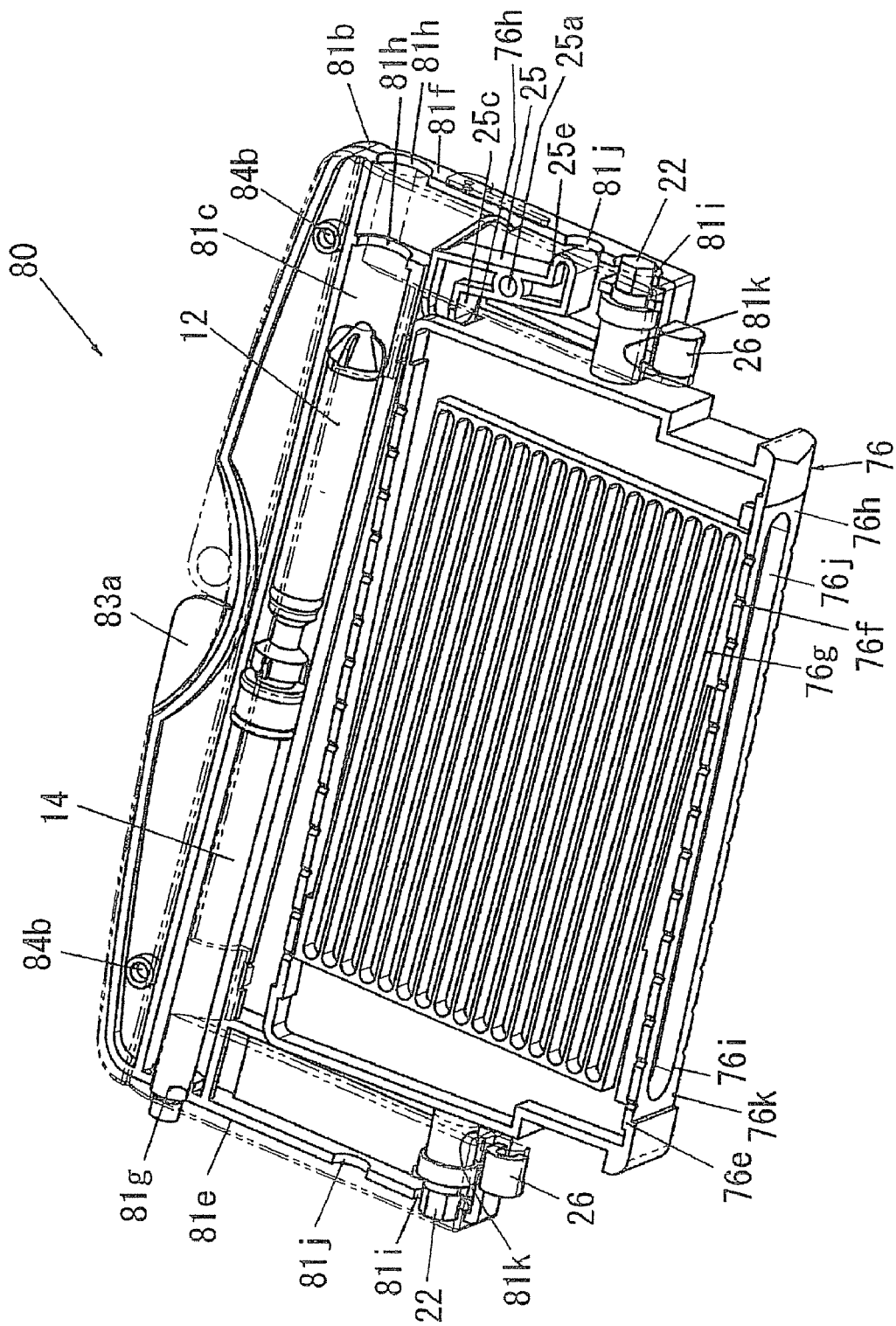
FIG. 35 is a perspective view showing the sample integration cassette being assembled, with an upper cover removed.
Figure 36:
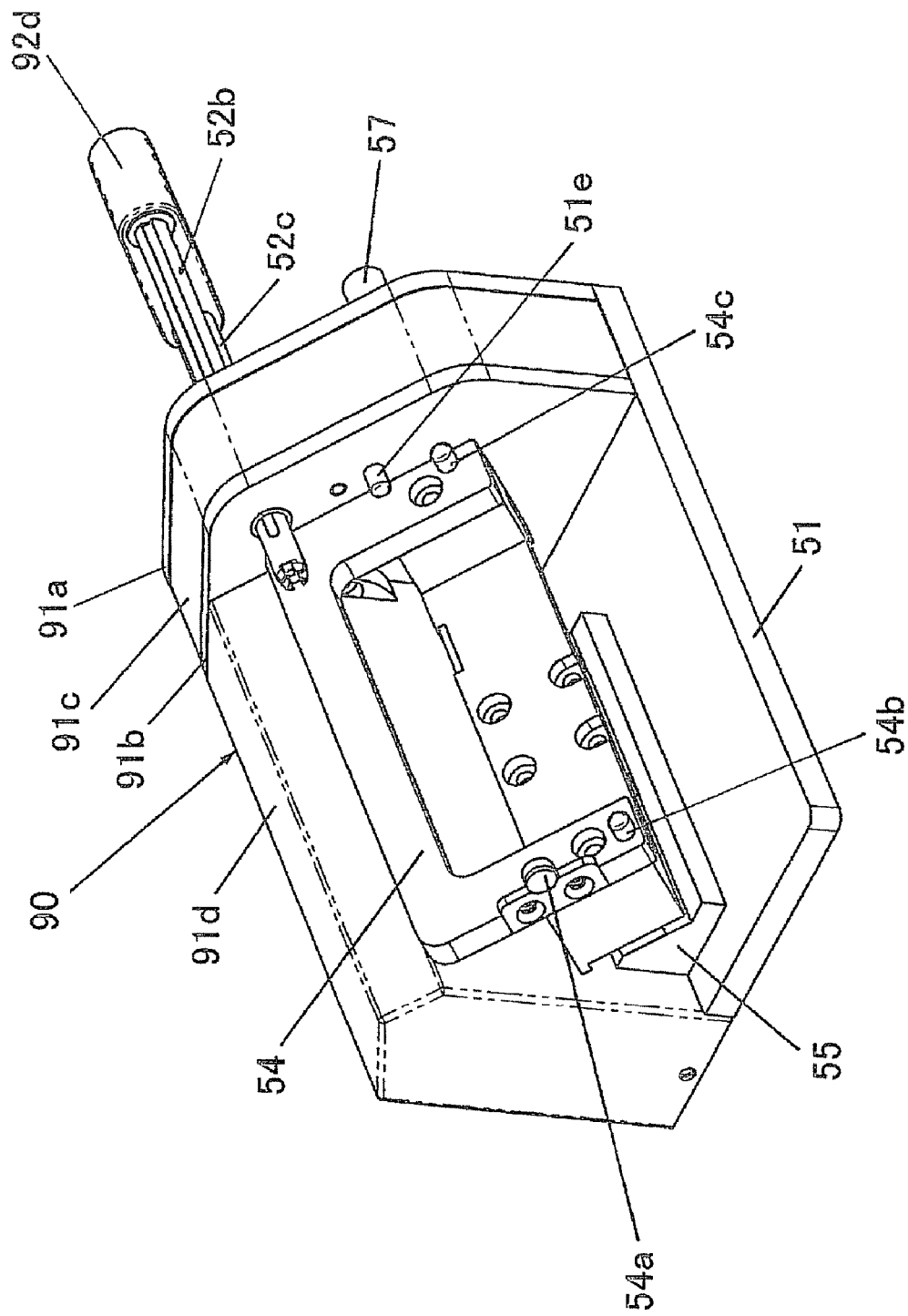
FIG. 36 is a perspective view showing a sample integration device according to the second embodiment of this invention.
Figure 37:
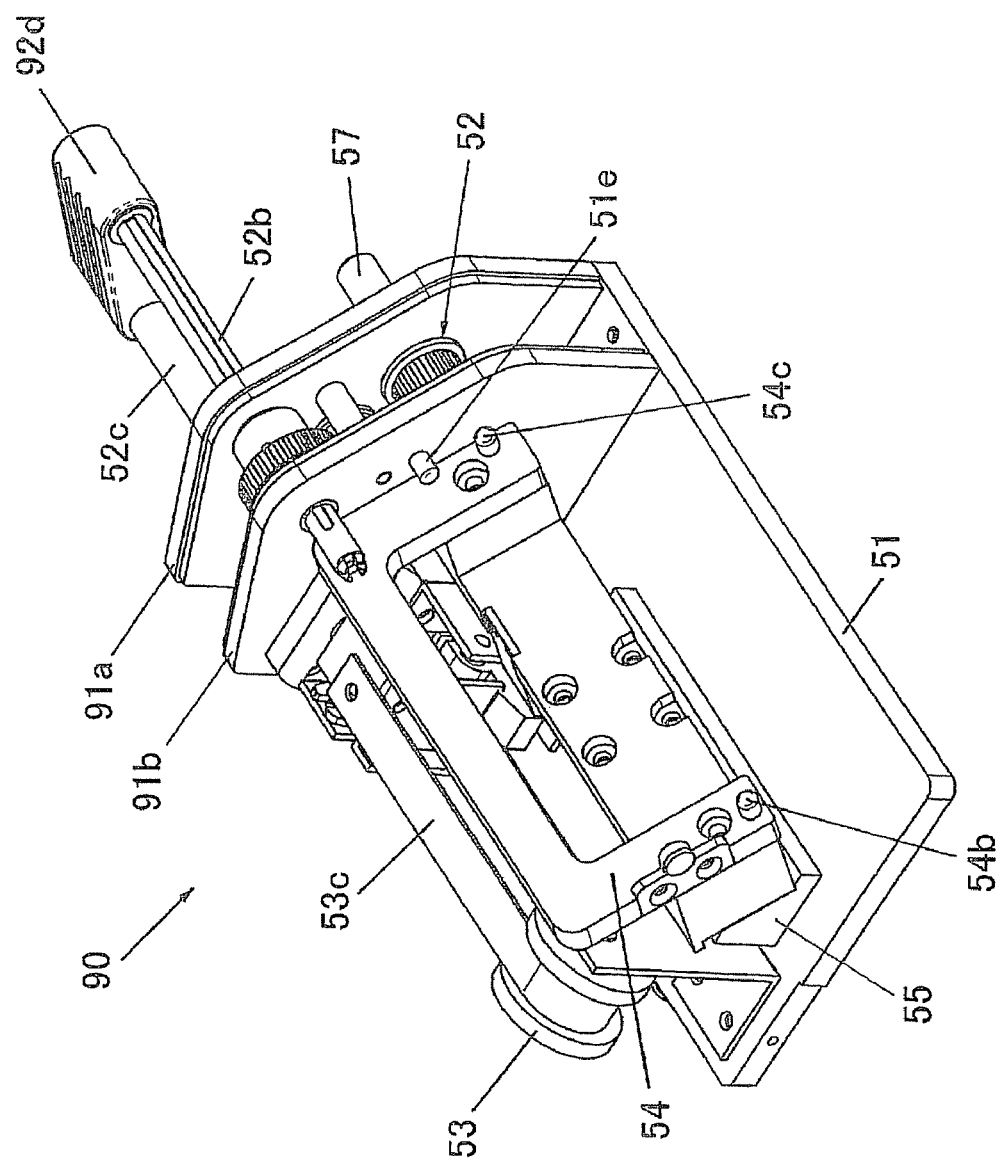
FIG. 37 is a perspective view showing the sample integration device of FIG. 36 with a cover removed.
Figure 38:
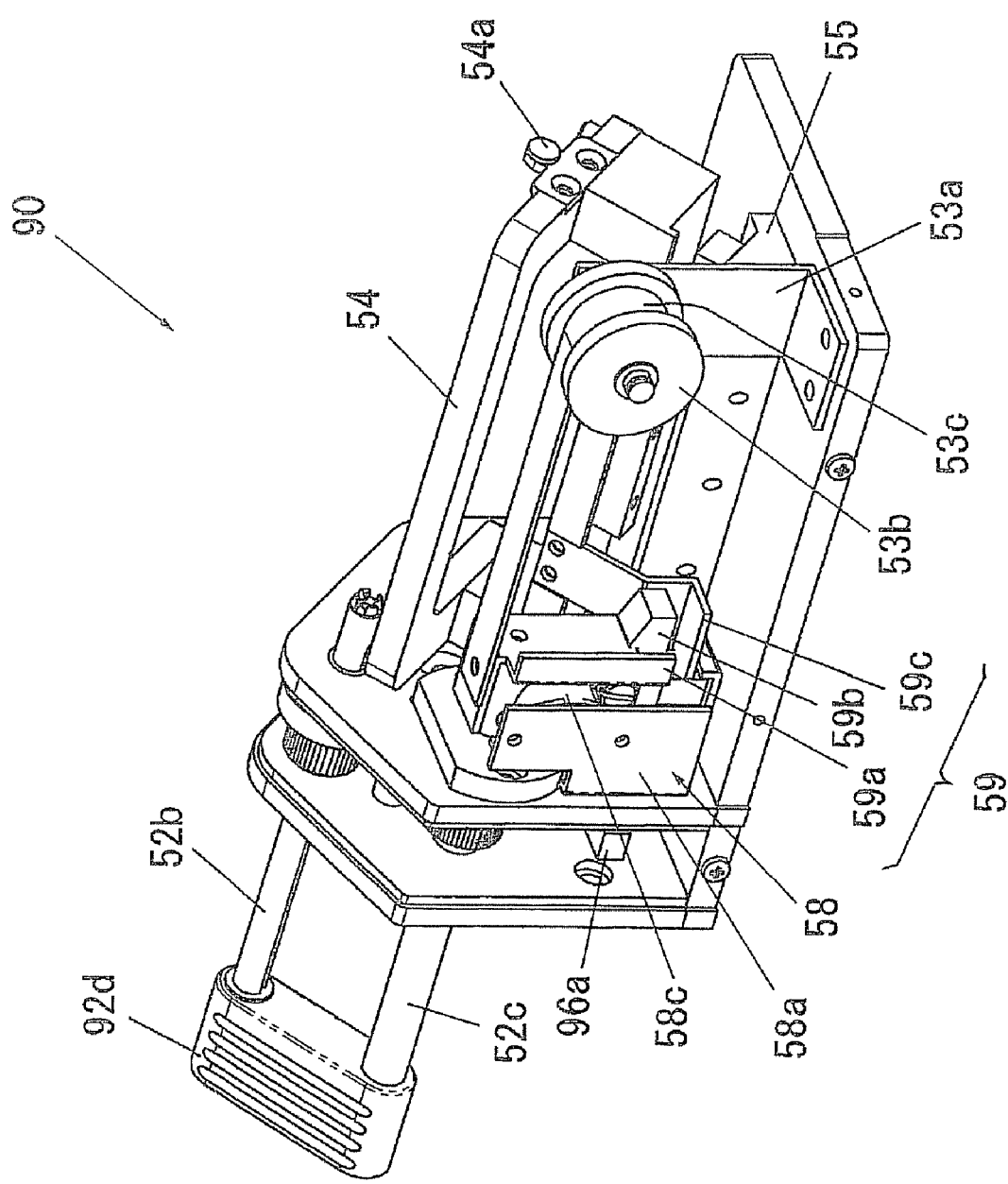
FIG. 38 is a perspective view of the sample integration device of FIG. 36 with the cover removed, as seen from the back.
Figure 39:
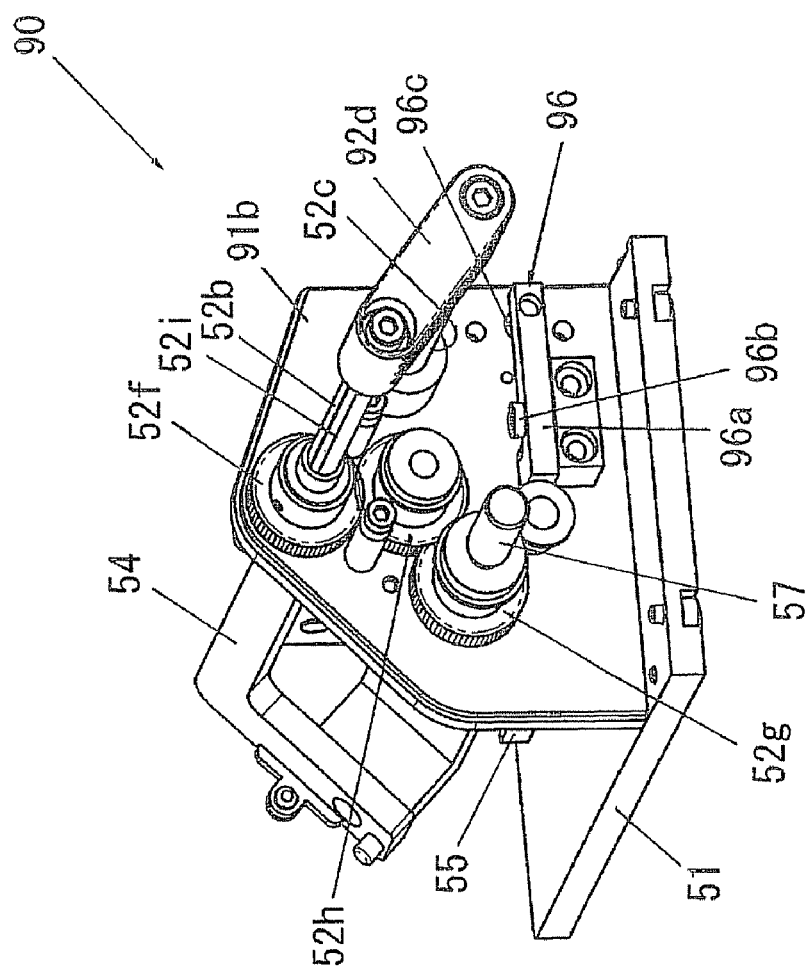
FIG. 39 is a perspective view showing the sample integration device of FIG. 36 with the cover and a right side wall removed, as seen from the right side.
Figure 40:
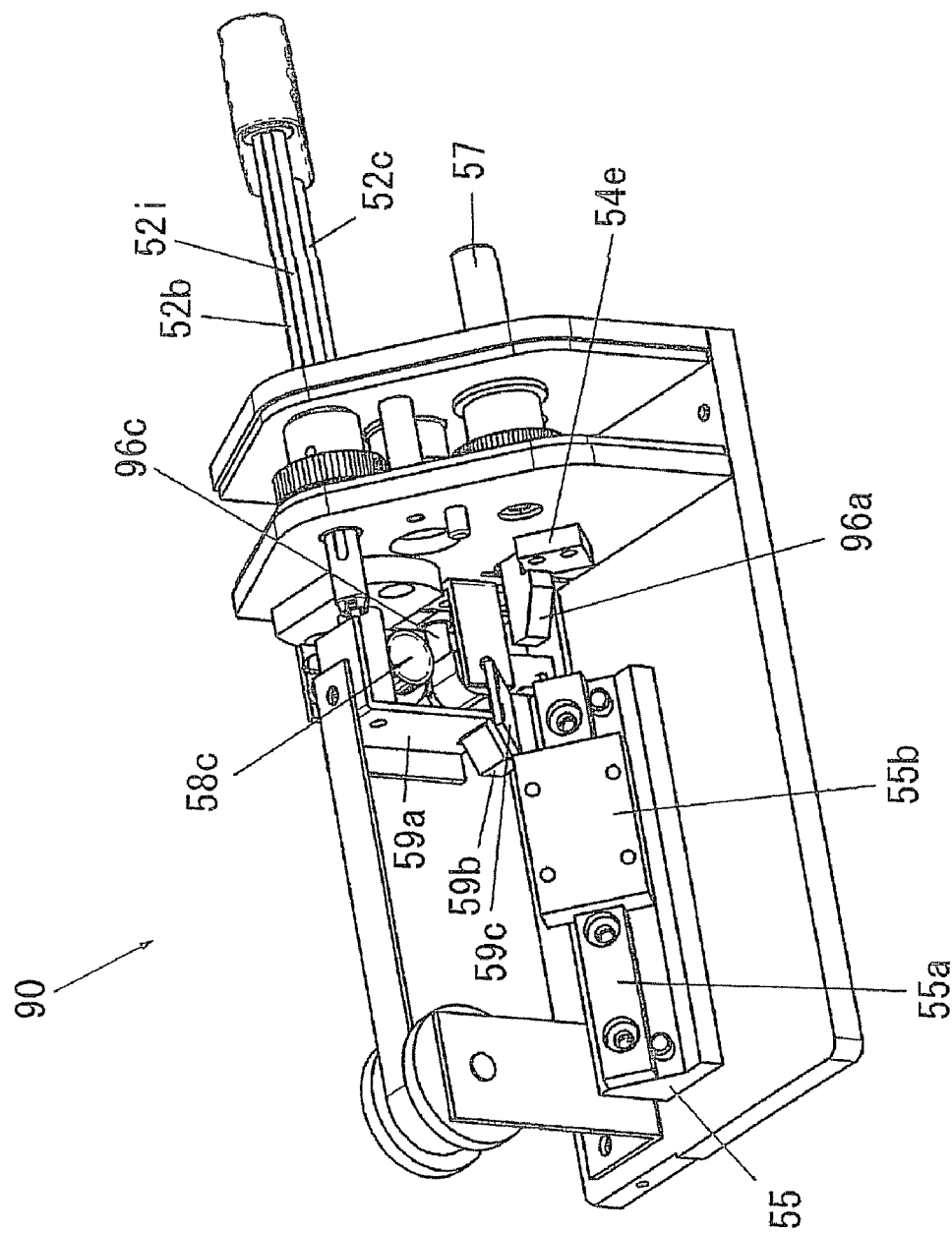
FIG. 40 is a perspective view showing the sample integration device with a sample integration cassette removed.

At a corner on that side of each platelike outer circumferential wall 76b, 76b which is opposite the side where the recess 76d, 76d is formed, the sample support carrier 76 is formed with a groove 76h that engages a rotation prevention means (see FIG. 34 and FIG. 35).

Further, in at least one of outer side surfaces 76i of the longer side platelike outer circumferential walls 76e, 76e connecting almost at right angles to the platelike outer circumferential walls 76b, 76b which is closer to the recesses 76d, 76d, the sample support carrier 16 is formed with a narrow slot 76j. The slot 76j provides a spotting position where a liquid suspending a reagent as a marker is applied to the sample support 10a that is wound on the sample support carrier 76 through the V grooves 76f, . . . , 76f.

At a corner of the sample support carrier 76 is formed a slit 76k in which to hold the front end of the sample support 10a.

To wind the sample support 10a around the sample support carrier 76, the front end of the sample support 10a is knotted.

With the knot caught in the slit 76k, the sample support 10a is passed through one V groove 76f, then the next V groove and so on in a predetermined winding order.

Next, the sample integration cassette 80, which accommodates protruding members in the cover to keep its entire outer surface as smooth and rounded as possible, is assembled as follows. As shown in FIG. 34 and FIG. 35, the sample assembly 12 and the sample support carrier 76 are set in a cassette jig 81. The cassette jig 81 is divided into an upper cover 81a and a lower cover 81b that together form an outer shell. With the upper cover 81a removed, the sample assembly 12 that has yet to be wound with the sample support 10a and the sample support carrier 76 not yet wound with the sample support 10a are assembled. In this state, the sample support 10a is wound around the sample support carrier 76. When it is installed in the jig, the sample assembly 12 is already attached with the shaft member 14.

First, the front end of the sample support 10a is secured to the slit 76k. Then, the sample support 10a is led onto a side surface opposite the one where the slit 76k is formed and then passed through the nearest V groove 76f not yet wound with the sample support 10a. The sample support 10a is further led to the opposite side and passed through the corresponding V groove 76f. It is again wound around the opposite side surface, passed through the next empty V groove 76e, then led to the opposite side surface and passed through the corresponding V groove 76f. This process is repeated until the sample support 10a is wound and passed through all V grooves 76f formed in the longer sides. Then a part of the sample support 10a near the position where it is to be cut is pushed down between the core 12a of the sample assembly 12 and the head 13. The head 13 is pressed against the front end of the core 12a to strongly clamp the sample support 10a. An excess part of the sample support 10a protruding on the side opposite the sample support carrier 76 is cut off in immediate proximity to the clamped position. Then, the upper cover 21a is attached and now the cassette 80 is complete.

The cassette jig 81 is formed in a shape of gate, comprised of a center member 81d having an accommodation hole 81c in which to rotatably accommodate the sample assembly 12 and side support members 81e, 81f projecting almost perpendicularly from the ends of the center member 81d. Rotating shafts 22 fitted over the shaft member 76c, 76c of the sample support carrier 76 are rotatably fitted into each of the side support members 81e, 81f. As a result, the sample support carrier 76 can be rotatably mounted to the cassette jig 81.

The cassette jig 81 is formed with a hole 81g at one end of the center member 81d and, at the other end, with holes 81h, 81h. The hole 81g communicates with the accommodation hole 81c and functions as a bearing in which the shaft member 14 connected to the sample assembly 12 is rotatably supported. The holes 81h, 81h are also communicated to the accommodation hole 81c and accepts a tool that drives the head 13 toward the core 12a to hold the end of the sample support 10a between them. Further, on the outside of the accommodation hole 81c, the center member 81d is formed with dampers 83a, 83b that help to assemble or disassemble the upper cover 81a and the lower cover 81b and which have their edges rounded so that they feel soft for fingers. Near the side support members 81e, 81f, the center member 81d also has protrusions (not shown) for positioning of these covers.

One of the side support members, 81f, pivotally supports a stopper 25 that prevents the rotation of the sample support carrier 76. The stopper 25 has at its center a shaft support portion formed with a shaft hole 25a. At one end the stopper 25 has an engagement end 25c protruding toward the sample support carrier 76 side. On the back of the engagement end 25c a leaf spring 25d is installed to urge the engagement end 25c toward the sample support carrier 76 side. At the other end the stopper 25 has an engagement end 25e formed on the same surface that the leaf spring 25d engages, the engagement end 25e being adapted to be pushed by a rod to disable the rotation prevention function.

The outer surfaces of the side support members 81e, 81f are formed with holes 81i, 81i in which to fit a tool that engages the rotating shafts 22 to rotate the sample support carrier or in which to fit a sample support carrier rotating shaft of the spotting device. The outer surfaces are also formed with holes 81j, 81j in which to insert a tool that engages the engagement end 25e of the stopper 25 to disable the rotation prevention function or to insert a pin of the spotting device.

At the front end of the side support members 81e, 81f on the lower cover 81b side, an hole side protruding member 26 for engagement is provided. At the front end of the side support members 81e, 81f on the upper cover 81a side, a shaft side protruding member 27 is provided for engagement with the hole side protruding member 26 on the lower cover 21b side.

In the sample assembly cassette 80 having its cassette jig 81 fitted with the sample assembly 12, that has yet to be wound with the sample support 10a, and with the sample support carrier 76 already wound with the sample support 10a, the side support members 81e, 81f are formed with rotating shaft support holes 81k, 81k. The rotating shaft support holes 81k, 81k allow the sample support carrier 76 to be installed at an inclination angle that matches the inclination angle of the groove 12e of the sample assembly 12 in which to lay the sample support 10a so that the axis of the sample assembly 12 is almost parallel to the slots 76g, ..., 76g of the sample support carrier 76.

Further, a sample integration device 90, as shown in FIG. 36 to FIG. 40, has a drive unit and a cassette mount locking member installed in a right side area of a base. These members as well as a spring device, a damper unit and a latch mechanism are enclosed by a cover. More specifically, the sample integration device 90 comprises: a base 51 having two side walls 91a, 91b erected separate from each other at a right-side end portion thereof so that they provide a U-shaped structure when viewed from the front; a drive unit 52 installed between the side walls 91a, 91b to rotate the sample assembly 12 and the sample support carrier 76 in an interlocked manner and to move the sample assembly 12 in the axial direction; a cover 91c provided on peripheries of the two side walls 91a, 91b to enclose and conceal the drive unit 52; a a spring device 53 to facilitate the linear, axial movement of the sample assembly 12 by applying a bias force to the sample assembly 12; a cassette mount 54 accommodating the cassette 80 at an angle and adapted to be moved linearly toward and away from the side walls 91a, 91b; a support table 55 having a direct motion bearing to support the cassette mount 54 linearly movable; and a cassette mount locking member 56 mounted on the left side wall 91a, when viewed from the front, to axially lock the cassette mount 54 when the cassette 80 is installed or removed.

On the left side wall 91b, a cassette mounting pin 51e protrudes horizontally above and toward a central part of side end portion of the cassette mount 54.

The drive unit 52 comprises: an axially movable rotating shaft 52b with its front end adapted to engage the head 13 of the sample assembly 12 installed in the cassette 80; a guide shaft 52c to prevent a rotation of the rotating shaft 52b as the rotating shaft 52b, after having completed its axial movement, returns to its home position and to pull the rotating shaft 52b in the return direction against a spring force; a connecting member 92d to connect the rotating shaft 52b and the guide shaft 52c at their ends protruding outside the cover 52a, and also to serve as a pull knob; a shaft side gear member 52f adapted to give a rotating force to the rotating shaft 52b and to function as a bearing to support the axial movement of the rotating shaft 52b; a drive side gear member 52g having a one-way clutch to manually transmit a rotating force to the rotating shaft 52b; and an intermediate gear member 52h to interlockingly connect the shaft side gear member 52f and the drive side gear member 52g.

The rotating shaft 52b has formed in its circumferential surface two grooves 52i, which are parallel to the center axis and arranged circumferentially equidistant positions. A pin (not shown) to transform the rotating force of the shaft side gear member 52f into a linear thrusting force for the rotating shaft 52b projects from the inner circumferential surface of the shaft side gear member 52f toward the center. The pin is so formed in length and diameter that its front end can be inserted axially movable into the grooves 52i. A manually operated handle 57 outwardly protruding from the side wall 91a is fitted over an end of the drive side gear member 52g. Turning the handle 57 with fingers to rotate the drive side gear member 52g transmits the rotating force from the drive side gear member 52g through the intermediate gear member 52h to the shaft side gear member 52f, from which the drive force is further transmitted to the rotating shaft 52b.

The cassette mount 54 has erected on its upper surface at the edge of a central part of the left side portion thereof a protruding support shaft member 54a whose front end is inserted into the hole 21j of the side support member 81e of the cassette 80. On its upper surface the cassette mount 54 also has a positioning member 54b at a lower end corner on the left side to block the cassette 20 from falling. Further, at a lower end corner on the right side of the cassette mount 54, a positioning member 54c is erected to prevent the cassette 80 from sliding down.

The cassette mount locking member 96 has arranged on the drive unit side of the side wall 91b an angled elongate member 96a oscillatable about a pivot shaft 96b. The cassette mount locking member 96 also has an unlocking member 96c that passes through the side wall 91b and pushes, in a manner interlocked with the operation of the guide shaft 52c, an end of the angled elongate member 96a situated on the side opposite its engagement end. When the cassette mount 54 approaches the side wall 91b, the angled elongate member 96a is operated to the locking side to engage a locking member 54e protruding toward the side end portion of the cassette mount 54 on its back side (lower side) to fix the cassette mount 54 at a position close to the side wall 91b.

On the back side of the cassette mount 54, there are installed a spring device 53, a damper unit 58 and a latch mechanism 59, all enclosed by a cover 96d.

The spring device 53 comprises a bracket 53a erected on the back side of the cassette mount 54, a bobbin 53b rotatably mounted on the bracket 53a, and a coiled spring 53c wound on the bobbin 53b with its free end secured to the front end of the guide shaft 52c.

The damper unit 58 comprises a damper bracket 58a and a damper device 58c having a damper gear (not shown) in mesh with a gear (not shown) on the guide shaft 52c. The damper device 58c uses an oil resistance type rotary damper to prevent a sharp movement.

The latch mechanism 59 comprises an engagement member 59a extending vertically downward from the front end of the guide shaft 52c, a lock member 59b mounted to the damper bracket 58a so that it is oscillatable about the axis, and an unlocking member 59c secured at its upper end to the cassette mount 54 so that it is linearly movable, and also adapted to push a non-engaging end of the lock member 59b to the unlocking side.

The front end portion of the guide shaft 52c is securely attached with the coiled spring 53c. When, with the lower end of the engagement member 59a engaged with the engaging end of the lock member 59b, the cassette mount 54 is moved toward the side wall 91b, causing the unlocking member 59c to push the non-engaging end of the lock member 59b to the unlocking side, the engagement member 59a is disengaged from the lock member 59b. As a result, the guide shaft 52c is moved by the bias force of the coiled spring 53c toward the side wall 91a against a resisting force of the damper device 58c.

To engage the front end of the rotating shaft 52b with the head 13 of the sample assembly 12, the connecting member 92d is pulled outwardly of the side wall 91a to allow the sample integration device 90 to operate on the cassette 80. At this time, the latch mechanism 59 is activated to prevent the rotating shaft 52b from returning to its original position. And after installation of the cassette, the latch mechanism 59 is disengaged to allow the rotating shaft 52b to be moved inwardly of the side wall 91b by the bias force of the coiled spring 53c. The damper device 58c gives an appropriate resisting force to the guide shaft 52c to control its speed, preventing it from moving sharply.

Figure 41:
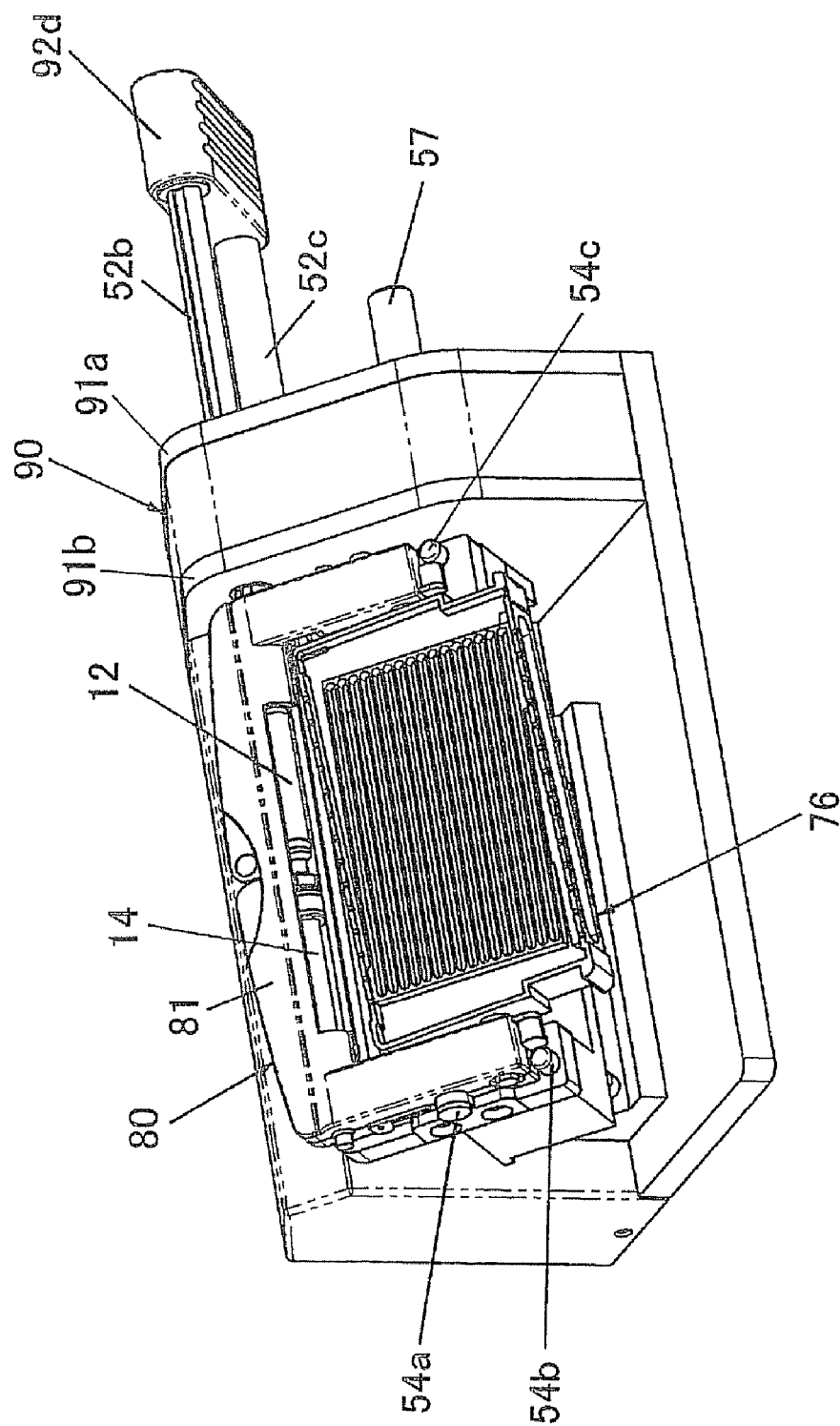
FIG. 41 is a perspective view showing the sample integration device mounted with the sample integration cassette.
Figure 42:
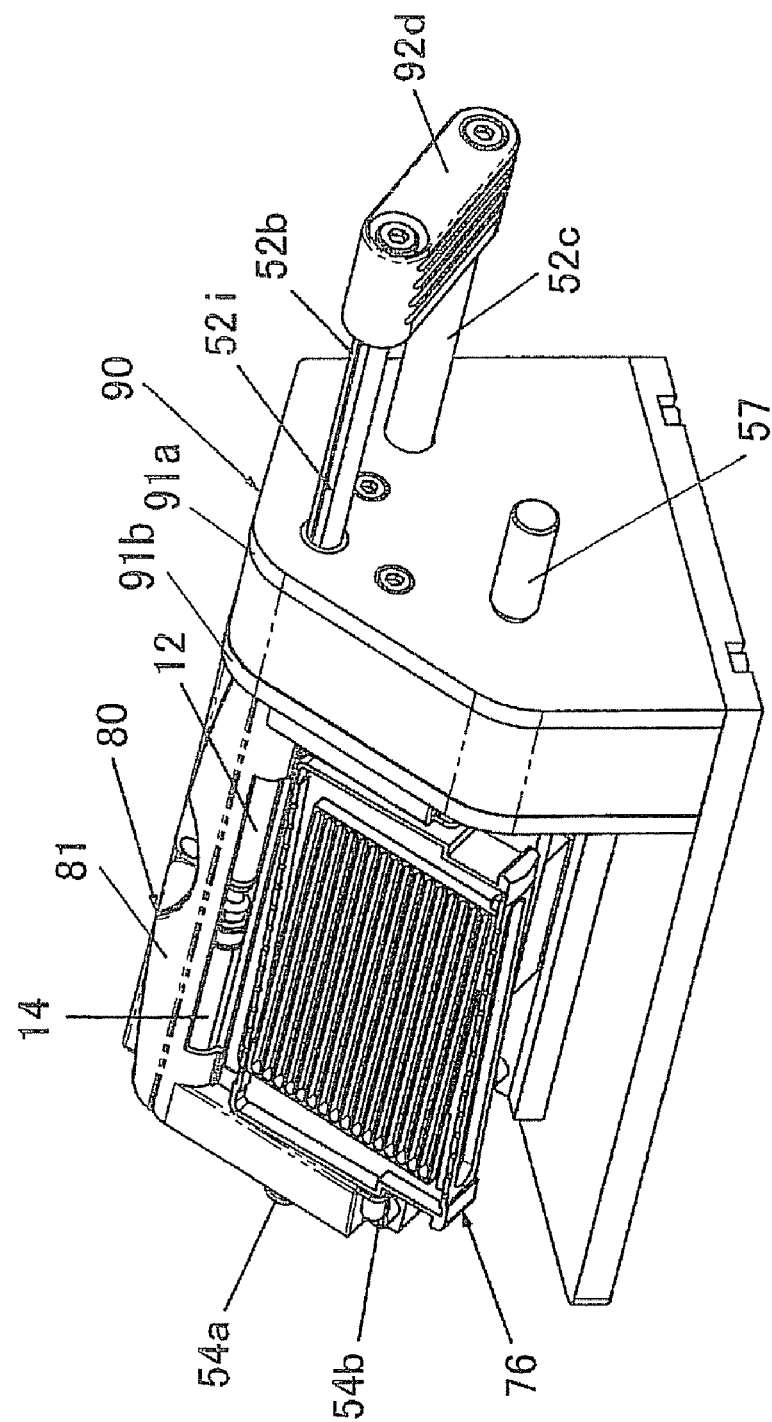
FIG. 42 is a right side perspective view showing the cassette mounted on the sample integration device and shifted to the right.

This sample integration device 90 is used as follows. As shown in FIG. 41 and FIG. 42, the cassette 80 is placed on the cassette mount 54; the front end of the support shaft member 54a is inserted into the hole 81j of the cassette 80 to support the cassette; with the protruding portions of the hole side protruding member 26 and the shaft side protruding member 27 used as the guide, the cassette 80 is roughly positioned and prevented from sliding down by the positioning members 54b, 54c; and then the cassette mount 54 is moved toward the right side wall 91b, when viewed from the front, until the pin 51e is inserted into the hole 81j. As a result, the latch mechanism 59 is disengaged and at the same time the pin 51e pushes the engagement end 25e of the stopper 25 of the cassette jig 81, moving the engagement end 25c which is engaged with the sample support carrier 76 toward the unlocking side, disengaging the sample support carrier 76 from the stopper 25. Now, the sample support carrier 76 is freely rotatable about the shaft members 76c, 76c relative to the cassette jig 81.

In this process, by the time the pin 51e is inserted into the hole 81j, the unlocking member 96c of the cassette mount locking member 96 moves to the unlocking side pushing the end of the angled elongate member 96a which is opposite the engagement end, thus disengaging the engagement end of the angled elongate member 96a from the locking member 54e provided on the back side of the cassette mount 54.

Then, the rotating shaft 52b is moved toward the sample assembly 12 to engage its front end with the head 13 so that its rotating force can be transmitted to the sample assembly 12. At the same time, as the guide shaft 52c moves, the unlocking member 96c of the cassette mount locking member 96 is moved toward the locking side, engaging the engagement end of the angled elongate member 96a with the locking member 54e provided on the back side of the cassette mount 54. As a result, the cassette mount 54 is fixed at a predetermined position.

After the sample support carrier 16 is set free, when the handle 57 connected to the drive side gear member 52g is turned, the drive side gear member 52g is rotated, causing the intermediate gear member 52h and the shaft side gear member 52f to rotate. With the gears rotated in this manner, the head 13 engaged with the front end of the rotating shaft 52b rotates with the sample assembly 12, winding up the sample support 10a from the sample support carrier 76. Since the latch mechanism 59 is disengaged, the rotating shaft 52b and the guide shaft 52c are gradually moved away from the side wall 91b by the bias force of the coiled spring 53c, winding up the sample support 10a along the groove 12e formed on the sample assembly 12.

As for the manufacture of the sample assembly according to the second embodiment, the process up to the step of applying sample suspending liquids to the sample support carrier 76 in the cassette 80 can be executed in the same procedure as the first embodiment. In the step of winding up the sample support from the sample support carrier 76 onto the sample assembly 12, the second embodiment only differs from the first embodiment in that the cassette mount locking member 96 is locked and unlocked in a manner interlocked with the operation of the rotating shaft 52b and the guide shaft 52c. But other steps can be performed in the same procedure as the first embodiment, so their explanations are omitted. As for the use of the sample assembly manufactured by the second embodiment, since the sample assembly is similar to that manufactured in the first embodiment, its use (e.g., accommodation-reaction-measurement process) is also similar to that described in the first embodiment. Thus, its explanation is omitted.

As described above, the sample assembly 12 can be manufactured with high precision and efficiency even by modifying devices and it is possible to manufacture the sample assembly 12 more effectively with higher precision and greater ease of use than in the first embodiment.

Third Embodiment

A simple device that functions as the spotting device 40 and the sample integration device 50 will be described as a third embodiment.

Figure 43:
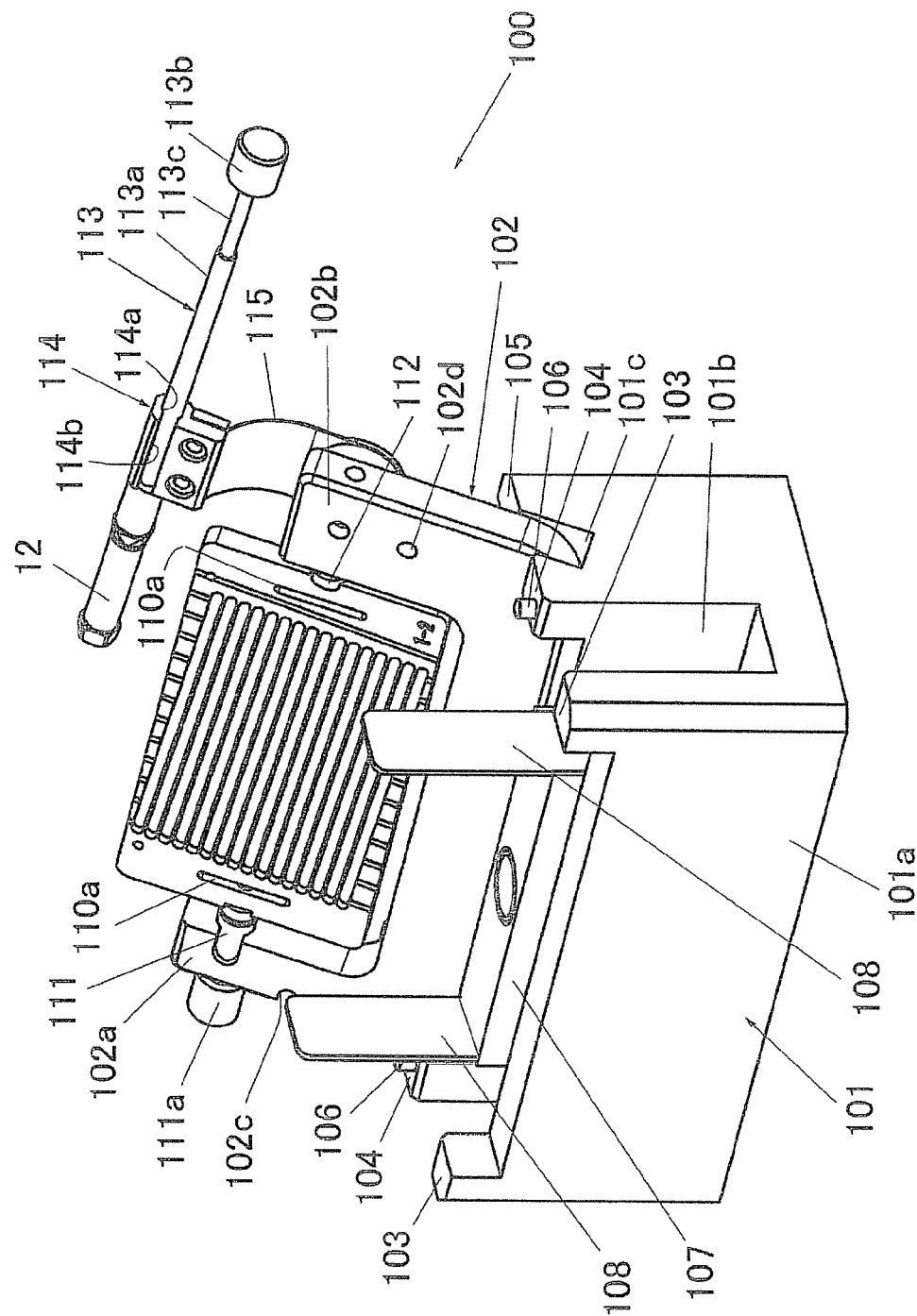
FIG. 43 is a perspective view showing a spotting and sample integration device being used in a sample integrating process according to a third embodiment of this invention.
Figure 44:
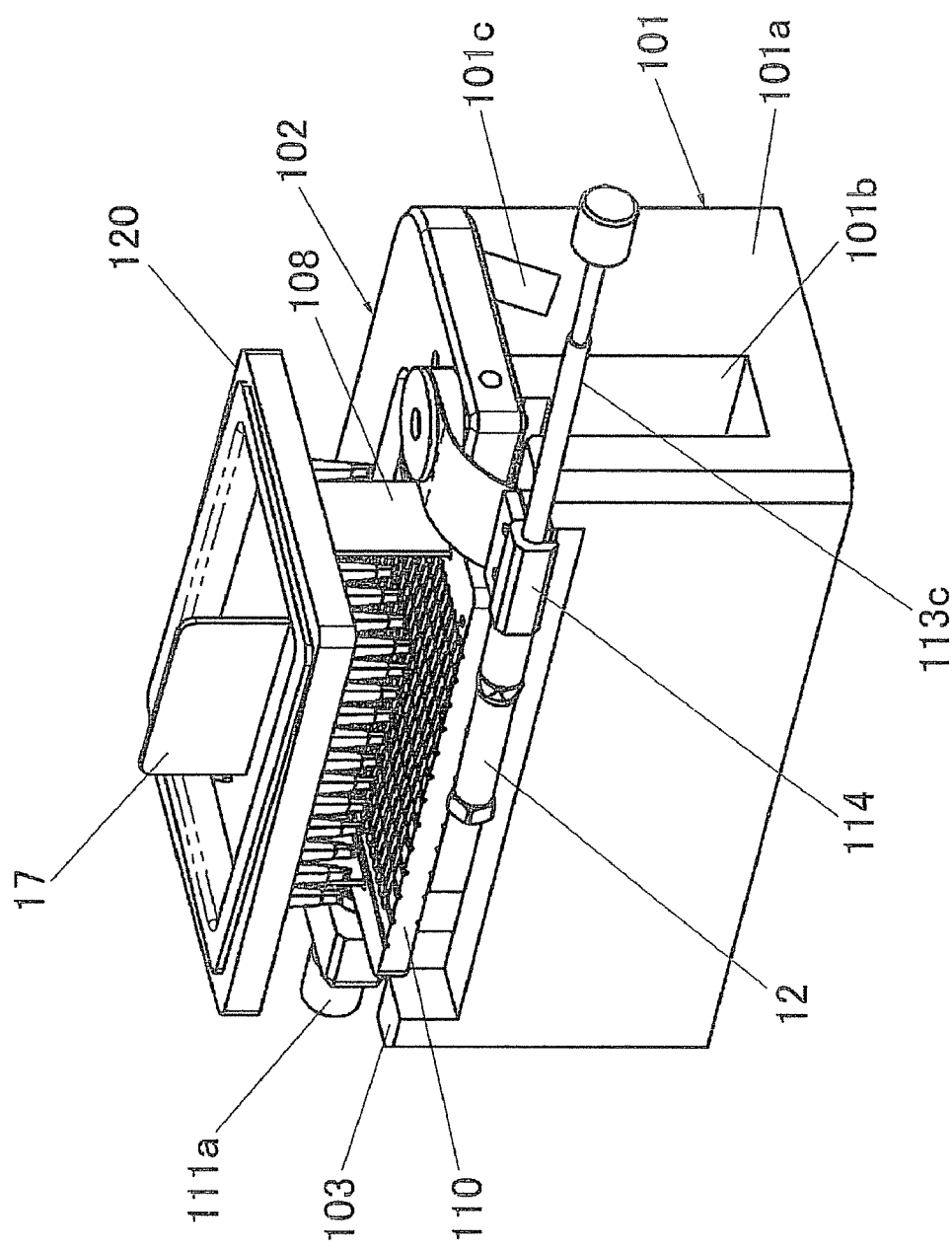
FIG. 44 is a perspective view showing the spotting and sample integration device of FIG. 43 being used in a spotting process.
Figure 45:
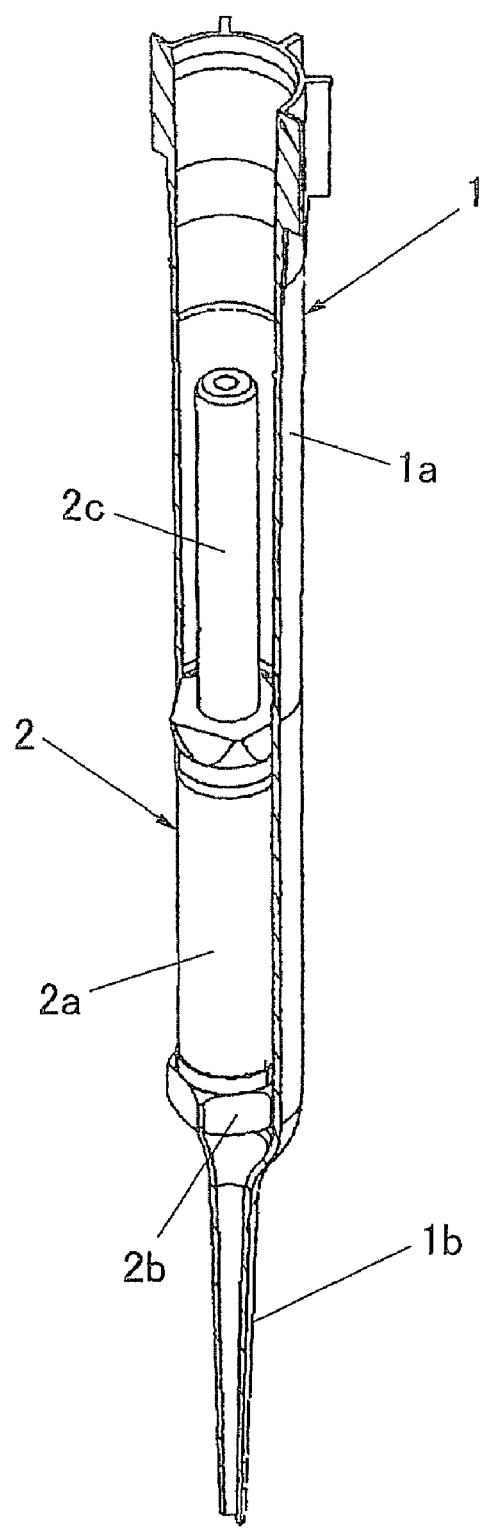
FIG. 45 is a partly cutaway perspective view showing a conventional pipette accommodating a sample assembly.
Figure 46:
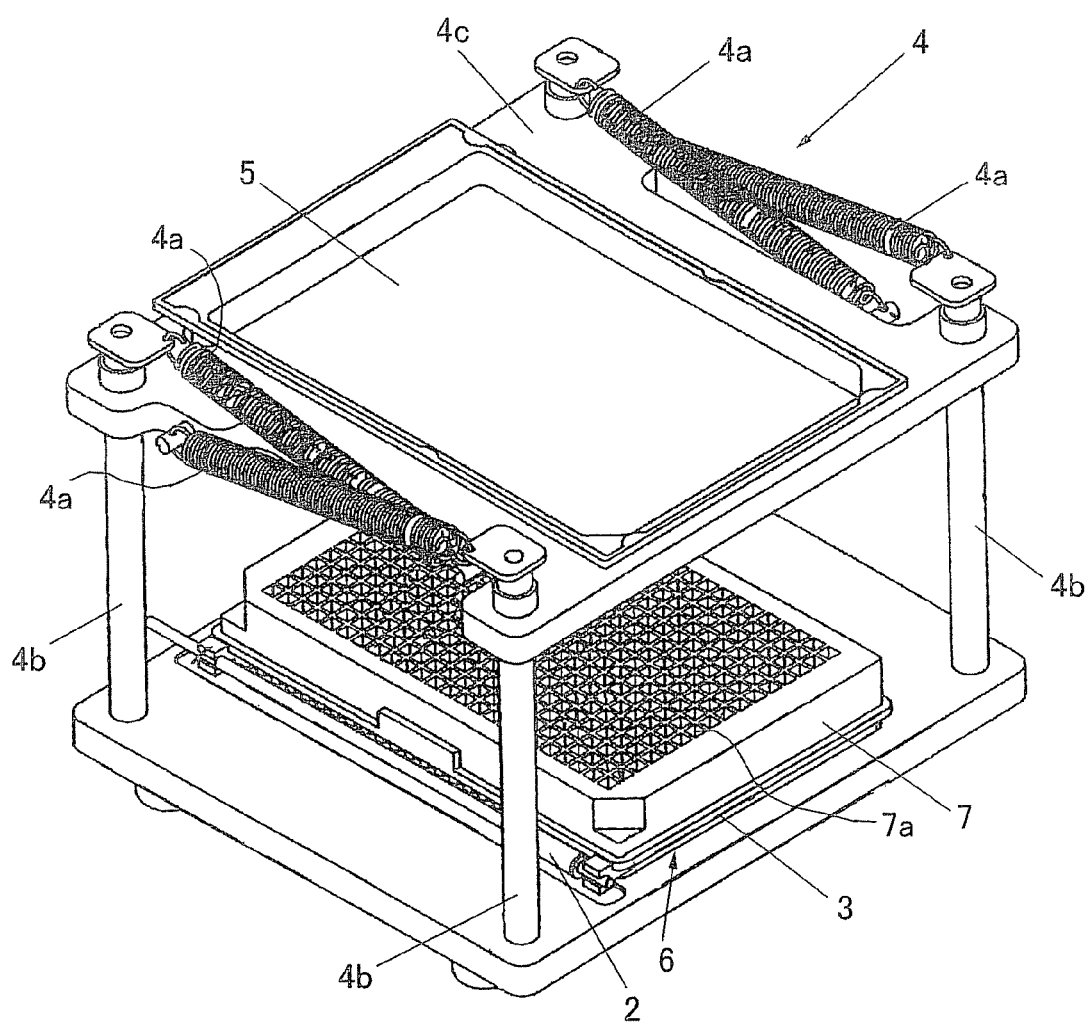
FIG. 46 is a perspective view showing a conventional spotting device.

A spotting and sample integration device 100, as shown in FIG. 43 and FIG. 44, comprises a base 101 functioning as the spotting device, and a holding member 102 that holds the sample assembly 12 and the sample support carrier 16 and functions as a sample integration device.

The base 101 has a rectangular parallelepiped body 101a with its longer side disposed horizontally. The body 101a has formed in its top surface a wide, vertically deep groove 101b longitudinally extending over its entire length at a position about one-third of the body width from the front of the body. At a position about one-third of the body width from the back, the body 101a is formed at its top surface with an inclined groove 101c that extends slantwise from the top surface downwardly forwardly and also longitudinally over the entire length of the body. The inclined groove 101c is slightly wider than the holding member 102 and deep enough so that the holding member 102, when inserted there, can maintain its upwardly rearwardly inclined attitude.

On the upper surface of the body of the base 101, there are formed pairs of left and right planar portions 103, 103, 104, 104, 105, 105 of the same height on which the holding member 102 lies almost horizontally flat. Intermediate portions of the members formed with the planar portions 103, 103, 104, 104, 105, 105 are set lower than these planar portions to stabilize the holding member 102 and to prevent the surface of a sample support carrier 110 mounted to the holding member 102 from contacting the intermediate portions between the planar portions 103, 103, 104, 104, 105, 105. On the center planar portions 104, 104 are erected pins 106, 106 that engage the holding member 102.

In a central part of the wide, deep groove 101b a sample support carrier mount 107 is installed vertically movable. The sample support carrier mount 107 is formed in a shape of almost rectangular parallelepiped and has vertically extending, platelike sample support carrier support members 108, 108 attached to both ends thereof. At an intermediate position between the sample support carrier support members 108, 108 a shaft member is erected for supporting the sample support carrier mount 107 vertically movably.

The holding member 102 is formed into a U-shaped member so that it can accommodate the sample support carrier 110 in a central part thereof. Both side portions 102a, 102b of the U-shaped member rotatably support, at their inner opposing surfaces, support shafts 111, 112 to which shaft members (not shown) of the sample support carrier 110 are fitted. Of these mounting shafts, the support shaft 111 is also axially movable so that the sample support carrier 110 can be mounted or dismounted by pulling outwardly a knob 111a that protrudes outwardly from the side portion 102a. In those surfaces (undersides) of the side portions 102a, 102b that contact the base when the holding member 102 is laid flat, positioning holes 102c, 102d are formed to receive the pins 106, 106 erected on the planar portions 104, 104 of the base.

On a surface of the side portion 102b (upper surface) opposite the surface that contacts the base, a sample assembly holding member 114 that rotatably holds a shaft member 113 connected to the base of the sample assembly 12 is so arranged that it can be deflected through a curved leaf spring 115 in a direction perpendicular to an axis of the shaft member 113. A surface of the shaft member 113 ranging from one end on the sample assembly connection side to near the opposite end is formed with a male thread 113a having a feed pitch of the sample assembly 12 determined by the pitch of the sample support winding spiral groove engraved on the sample assembly 12 and the pitch of the sample support wound on the sample support carrier 110. Then, the holding end of the sample assembly holding member 114 is formed with a female thread portion 114a that engages with the male thread 113a of the shaft member 113. At its end opposite the sample assembly connection side the shaft member 113 is provided with a knob 113b. Turning the knob 113b can wind up the sample support from the sample support carrier 110 onto the sample assembly 12 at a predetermined feed pitch. Between the portion of the shaft member 113 where the male thread 113a is formed and the knob 113b, a round bar portion 113c is formed which is smaller in diameter than the root of the male thread 113a. This arrangement enables the shaft member 113 to be inserted into the female thread portion 114a from an opening 114b formed at the side of the holding end of the sample assembly holding member 114.

At its both end portions of the central part close to where its shaft members to be fitted into the support shafts 111, 112 are provided, the sample support carrier 110 is formed with slots 110a, 110a piercing through the front and back surfaces of the carrier, through which the sample support carrier support members 108, 108 can be inserted. V grooves 116e, ..., 116e, slots 116f, ..., 116 and shaft members of the sample support carrier 110 are formed in the same way as in the first embodiment.

A mounting jig 120 to mount the delivery member 17 is formed into a square ring frame, which has a mounting portion (not shown) at its central part into which the delivery member 17 is inserted from above. The mounting jig 120 also has formed in one surface of its both side portions slots (not shown) that do not pierce through the side portions and which engage the front ends of the sample support carrier support members 108, 108 and stably support them.

As shown in FIG. 44, by attaching the sample support carrier 110 to the holding member 102, inserting the sample support carrier support members 108, 108 into the slots 110a, 110a of the sample support carrier 110 and fitting the positioning holes 102c, 102d of the holding member 102 over the pins 106, 106 of the base 101, the holding member 102 is held almost horizontally on the base 101.

After the holding member 102 is mounted, the mounting jig 120 is placed over the holding device by fitting its slots 110a, 110a over the ends of the sample support carrier support members 108, 108. Further, the delivery member 17 is set in the mounting portion of the mounting jig 120. Then, the delivery member 17 is pushed down from above to apply sample containing liquids to the sample support wound on the sample support carrier 110 in a predetermined row and column matrix. Then, the left and right sides of the delivery member 17 are reversed before putting it in the mounting portion again. The delivery member 17 is pushed down to apply new liquids to the sample support at intermediate positions between the previously applied liquids.

As shown in FIG. 43, after the liquids have been applied to both surfaces of the sample support carrier 110, the delivery member 17 and the mounting jig 120 are removed. Then the positioning holes 102c, 102d of the holding member 102 are disengaged from the pins 106, 106 and the sample support carrier 110 is pulled out from the sample support carrier support members 108, 108. An end portion of the holding member 102, opposite the end portion from which the sample assembly holding member 114 is projected, is inserted into the inclined groove 101c so that the holding member 102 which holds the sample support carrier 110 with the sample support applied with liquids is held inclined rearwardly upwardly.

The knob 113b of the shaft member 113 is turned to wind up the sample support from the sample support carrier 110 onto the core 12a of the sample assembly 12 at a predetermined pitch. At this time, the sample support carrier 110 rotates as the sample support is wound up, paying out the sample support wound on the sample support carrier 110 to the sample assembly side.

The leaf spring 115 deflects by the tension of the sample support produced during its feeding operation, minimizing changes in the sample support tension.

DESCRIPTION OF REFERENCE NUMBERS

10: Probe
10a: Sample support
11: Pipette
12: Sample assembly
12a: Core
12c: Handle
12e: Groove
12q, 13a: Rib
12p: Centering portion
12r: Front end side shaft portion
12s: Front end side stepped portion
12t: Flange portion
12u: Stepped portion
13: Head
14: Shaft member
15: O-ring
16, 76: Sample support carrier
16c, 76c: Shaft member
16d, 76d: Notch
16e, 116e: V groove
16f, 16i, 76g, 76j, 116f (elongate) slot
16g, 76f: groove (for stopper engagement)
16j, 76k: Slit
17: Delivery member
17b: Protruding member
18: Combination groove
20, 80: Cassette
21a, 81a: Upper cover
21b, 81b: Lower cover
21, 81: Cassette jig
21d, 81d: Center member
21e, 21f, 81e, 81f: Side support member
21c, 81c: Accommodation hole
21h, 21i, 81h, 81i, 81j: Hole (opening)
22, 96: Rotating shaft
25: Stopper
26: Hole side protruding member
26a: Shaft hole
27: Shaft side protruding member
27a: Shaft
40: Spotting device
41: Base
41a: Cassette mount
41b: Positioning member
41c: Stopper
42: Stand
42b: Guide rail
43: Movable table
43b: Delivery member mounting table
43c: Holder portion
44, 53: Spring device
44a, 53b: Coiled spring
44b, 53a: Bobbin
50, 90: Sample integration device
51: Base
51e: Pin
52: Drive unit
52a, 91c, 91d: Cover
52b: Rotating shaft
52c: Guide shaft
52d: Connecting member
52i, 76f: Groove
53: Spring device
54: Cassette mount
55: Support table
56: Cassette mount locking member
57: Handle
58: Damper unit
59: Latch mechanism
60: Sample assembly rotating device
61: Rotating shaft
63: Gear
63: Drive gear
64: Motor
65: Dry battery
66: Switch
76b, 76e: Platelike outer circumferential wall
91a, 91b: Side wall
96: Cassette mount locking member
96a: Angled elongate member
96b: Rotating shaft
96c: Unlocking member
100: Spotting and sample integration device
101: Base
101a: Body
101b (Deep) groove
101c: Inclined groove
102: Holding member 103, 104, 105: planar portion
106: Pin
107: Sample support carrier mount
108: Sample support carrier support members
111, 112: Support shaft
113a: Male thread
113b: Knob
113c: Round bar portion
114: Sample assembly holding member
114a: Female thread portion
114b: Opening
115: Leaf spring

The invention claimed is:

1. A sample integration cassette comprising:
a sample support carrier having a sample support wound thereon;
a sample assembly to which the sample support can be fed from the sample support carrier and wound around the sample assembly, wherein the sample assembly and the sample support carrier are arranged so that the sample support can be fed from the sample support carrier to the sample assembly at a constant angle at all times, wherein the sample assembly is rotatable about, and linearly movable along, an axis; and
a drive unit connectable to the sample assembly and the sample support carrier to give a drive force interlockingly and synchronously to the sample assembly and the sample support carrier;
wherein the sample assembly integrally has a core and a head;
wherein the core is formed with a spiral groove at a predetermined pitch and has the sample support wound in the spiral groove; and
wherein the head is connected to a front end of the core such that it is movable toward and away from the front end of the core to hold a front end portion of the sample support.

2. The sample integration cassette according to claim 1, wherein the sample assembly is formed with an O-ring groove at a rear end of the core so that a rear end portion of the sample support can be held by an O-ring fitted in the O-ring groove.

3. The sample integration cassette according to claim 1, comprising:
a central body portion to axially accommodate the sample assembly such that it is rotatable about the axis; and
a pair of side support portions to rotatably support the sample support carrier such that the spiral groove formed in the sample assembly for winding the sample support is almost parallel to the sample support wound on the sample support carrier;
wherein the pair of side support portions and the central body portion having the side support portions at both ends thereof combine to form a gatelike structure to wind the sample support onto the sample assembly from the sample support carrier.

4. The sample integration cassette according to claim 3, wherein the central body portion has formed in a side surface of a sample assembly accommodation portion thereof an opening that allows the sample assembly to be connected with a drive shaft;
wherein the side support portion has formed in a side surface of a carrier shaft support portion thereof an opening that allows the sample support carrier to be connected with a drive shaft that rotates in synchronism with the rotation of the sample assembly, so that the sample assembly and the sample support carrier can be interlocked with each other.

5. The sample integration cassette according to claim 1, further comprising a handle, the handle comprising a front end side shaft portion fitted into the core; a front end stepped portion that, together with the rear end of the core, forms an O-ring groove; a centering portion having a plurality of ribs that engage the inner surface of a large-diameter portion of a pipette for centering and positioning; a circular column portion situated at the central part of the handle; and a connecting portion formed at the rear end of the handle for connection with a shaft member.

6. A sample integration cassette comprising:
a sample support carrier having a sample support wound thereon;
a sample assembly to which the sample support can be fed from the sample support carrier and wound around the sample assembly, wherein the sample assembly includes a core, wherein the sample assembly and the sample support carrier are arranged so that the sample support can be fed from the sample support carrier to the sample assembly at a constant angle at all times, wherein the sample assembly is rotatable about, and linearly movable along, an axis; and
a drive unit connectable to the sample assembly and the sample support carrier to give a drive force interlockingly and synchronously to the sample assembly and the sample support carrier;
wherein the sample assembly is formed with an O-ring groove at a rear end of the core so that a rear end portion of the sample support can be held by an O-ring fitted in the O-ring groove.

7. A sample integration cassette comprising:
a sample support carrier having a sample support wound thereon;
a sample assembly to which the sample support can be fed from the sample support carrier and wound around the sample assembly, wherein the sample assembly and the sample support carrier are arranged so that the sample support can be fed from the sample support carrier to the sample assembly at a constant angle at all times, wherein the sample assembly is rotatable about, and linearly movable along, an axis; and
a drive unit connectable to the sample assembly and the sample support carrier to give a drive force interlockingly and synchronously to the sample assembly and the sample support carrier;
a central body portion to axially accommodate the sample assembly such that it is rotatable about the first axis; and
a pair of side support portions to rotatably support the sample support carrier such that the spiral groove formed in the sample assembly for winding the sample support is almost parallel to the sample support wound on the sample support carrier;
wherein the pair of side support portions and the central body portion having the side support portions at both ends thereof combine to form a gatelike structure to wind the sample support onto the sample assembly from the sample support carrier.

8. The sample integration cassette according to claim 7, wherein the central body portion has formed in a side surface of a sample assembly accommodation portion thereof an opening that allows the sample assembly to be connected with a drive shaft;

wherein the side support portion has formed in a side surface of a carrier shaft support portion thereof an opening that allows the sample support carrier to be connected with a drive shaft that rotates in synchronism with the rotation of the sample assembly, so that the sample assembly and the sample support carrier can be interlocked with each other.

* * * * *

UNITED STATES PATENT AND TRADEMARK OFFICE
CERTIFICATE OF CORRECTION

| | |
|---|---|
| PATENT NO. | : 8,168,142 B2 |
| APPLICATION NO. | : 11/568112 |
| DATED | : May 1, 2012 |
| INVENTOR(S) | : Hideji Tajima et al. |

It is certified that error appears in the above-identified patent and that said Letters Patent is hereby corrected as shown below:

Column 5, Line 20, change "mauler" to -- manner --

Column 10, Line 66, change "pipette 111" to -- pipette 11 --

Column 25, Line 57, change "dampers" to -- clampers --

Claim 7, Column 34, Line 59, delete the word "first"

Signed and Sealed this
Twenty-sixth Day of June, 2012

David J. Kappos
*Director of the United States Patent and Trademark Office*